(12) United States Patent
Haugen et al.

(10) Patent No.: US 11,560,582 B2
(45) Date of Patent: Jan. 24, 2023

US011560582B2

(54) FUSION MOIETIES AND MICROBIAL HOSTS FOR PROTEIN PRODUCTION

(71) Applicant: UNIVERSITETET I TROMSØ—NORGES ARKTISKE UNIVERSITET, Tromsø (NO)

(72) Inventors: Peik Haugen, Kvaløysletta (NO); Miriam Grgic, Tromsø (NO); Jenny Johansson Söderberg, Tromsø (NO)

(73) Assignee: UNIVERSITETET I TROMSØ—NORGES ARKTISKE UNIVERSITET, Tromsø (NO)

( * ) Notice: Subject to any disclaimer, the term of this patent is extended or adjusted under 35 U.S.C. 154(b) by 0 days.

(21) Appl. No.: 17/251,899

(22) PCT Filed: Jun. 19, 2019

(86) PCT No.: PCT/EP2019/066291
§ 371 (c)(1),
(2) Date: Dec. 14, 2020

(87) PCT Pub. No.: WO2019/243467
PCT Pub. Date: Dec. 26, 2019

(65) Prior Publication Data
US 2021/0130865 A1    May 6, 2021

(30) Foreign Application Priority Data

Jun. 19, 2018 (GB) .................................... 1810016

(51) Int. Cl.
*C12P 21/02* (2006.01)
*C12N 9/16* (2006.01)

(52) U.S. Cl.
CPC ................ *C12P 21/02* (2013.01); *C12N 9/16* (2013.01); *C12Y 301/11001* (2013.01); *C07K 2319/00* (2013.01)

(58) Field of Classification Search
CPC ... C12P 21/02; C12Y 301/11001; C12N 9/16; C07K 2319/02; C07K 2319/00
See application file for complete search history.

(56) References Cited

U.S. PATENT DOCUMENTS 8,993,279 B2 * 3/2015 Asakura ................... C12P 13/08
435/7.1
9,446,108 B2 * 9/2016 Sorum ................ A61K 39/0208

FOREIGN PATENT DOCUMENTS

| EP | 2128263 A1 | 12/2009 |
| EP | 2463377 A1 | 6/2012 |
| JP | 2005176826 A | 7/2005 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Fendrihan et al., Psychrophilic Microorganisms as Important Source for Biotechnological Processes. Adaption of Microbial Life to Environmental Extremes, Chapter 7, 2017: 147-199. (Year: 2017).*
Giuliani M., Novel Processes and Products for Recombiinant Productiion of Biiopharmaceutiicals, Ph.D. Thesis, Indirizzo Biotecnologie Industriali Università di Napoli Federico II, Italy, 2009, pp. 1-153. (Year: 2009).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Urbanczyk et al., Int. J. Syst. Evol. Microbiol., 2007, vol. 5: 2823-2829. (Year: 2007).*
Database UniProt [Online], "SubName: Full=Putative exported protein {ECO:0000313 | EMBL: CED70270.1};", Nov. 26, 2014.
Database EMBL [Online], "Aliivibrio wodanis genome assembly, chromosome: 1", Uniprot, Sep. 30, 2014.
H. Urbanczyk et al., "Reclassification of *Vibrio fischeri, Vibrio logei, Vibrio salmonicida* and *Vibrio wodanis* as *Aliivibrio fischeri* gen. nov., comb. nov., *Aliivibrio logei* comb. nov., *Aliivibrio salmonicida* comb. nov. and *Aliivibrio wodanis* comb. nov.", International Journal of Systematic and Evolutionary Microbiology, vol. 57, No. 12, Dec. 1, 2007, pp. 2823-2829.
Giuliani et al., "Recombinant production of a single-chain antibody fragment inPseudoalteromonas haloplanktisTAC125", Applied Microbiology and Biotechnology, Springer Berlin Heidelberg, Berlin/Heidelberg, vol. 98, No. 11, Feb. 18, 2014, pp. 4887-4895.
Sannino F et al., "A novel synthetic medium and expression system for subzero growth and recombinant protein production inPseudoalteromonas haloplanktisTAC125", Applied Microbiology and Biotechnology, Springer Berlin Heidelberg, Berlin/Heidelberg, vol. 101, No. 2, Oct. 27, 2016, pp. 725-734.

(Continued)

*Primary Examiner* — Ganapathirama Raghu
(74) *Attorney, Agent, or Firm* — Fox Rothschild LLP

(57) ABSTRACT

The present invention relates to fusion proteins comprising (i) a fusion moiety based on SEQ ID NO:1 and (ii) a protein. Also provided are nucleic acids encoding such fusion proteins and compositions comprising such fusion proteins. The invention also provides a method for increasing the expression level of a protein in a host cell or increasing the level of secretion of a protein from a host cell, said methods employing a fusion moiety in accordance with the invention. The invention further provides a method of producing a protein, said method comprising culturing an *Aliivibrio wodanis* host cell comprising a heterologous nucleic acid molecule encoding a protein under conditions suitable for the expression of the encoded protein. Certain deposited strains of *Aliivibrio wodanis* are also provided.

14 Claims, 12 Drawing Sheets

Figure 1:
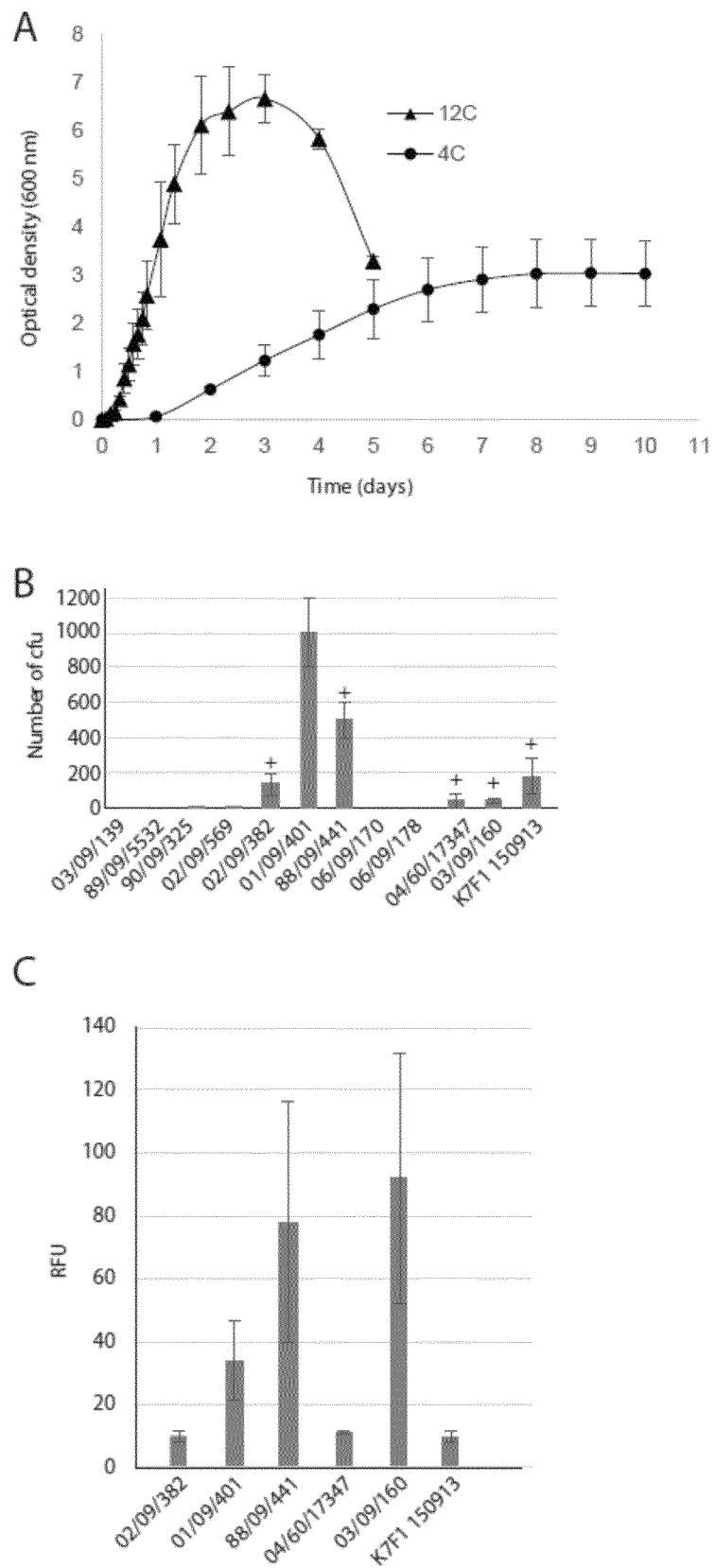

Specification includes a Sequence Listing.

(56) References Cited

OTHER PUBLICATIONS

R Miyake et al., "Construction of a low-temperature protein expression system using a cold adapted bacterium, *Shewanella* sp. strain Ac10, as the host", Applied and Environmental Microbiology, American Society for Microbiology, US, vol. 73, No. 15, May 25, 2007, pp. 4849-4856.
T. Miyashiro et al., The N-acetyl-D-glucosamine repressor NagC of Vibrio fischeri facilitates colonization of Euprymna scolopes. Mol Microbiol 82, 15 894-903 (2011).
A. K. Dunn, D. S. Millikan, D. M. Adin, J. L. Bose, E. V. Stabb, New rfp- and pES213-derived tools for analyzing symbiotic Vibrio fischeri reveal patterns of infection and lux expression in situ. Applied and environmental microbiology 72, 802-810 (2006).
D. L. Milton, R. O'Toole, P. Horstedt, H. Wolf-Watz, Flagellin A is essential for the virulence of Vibrio anguillarum. J Bacteriol 178, 1310-1319 (1996).
Aronson DE, Costantini LM, Snapp EL: Superfolder GFP is fluorescent in oxidizing environments when targeted via the Sec translocon. Traffic 2011, 12.
Zhang Z, Tang R, Zhu D, Wang W, Yi L, Ma L: Non-peptide guided autosecretion of recombinant proteins by super-folder green fluorescent protein in *Escherichia coli*. Sci Rep 2017, 7:6990.
Pedelacq JD, Cabantous S, Tran T, Terwilliger TC, Waldo GS: Engineering and characterization of a superfolder green fluorescent 5 protein. Nat Biotechnol 2006, 24.
E. V. Stabb, E. G. Ruby, in Methods in enzymology. (Elsevier, 2002), vol. 358, pp. 413-426.
Summerer D, (2008) DNA polymerase profiling. Methods Mol Biol.35 429:225-35.
Petersen TN, Brunak S, von Heijne G, Nielsen H: SignalP 4.0: discriminating signal peptides from transmembrane regions. Nature methods 2011, 8:785.
Parrilli, Duilio & Tutino (2008) Text book Chapter 21 from "Pyschrophiles: from Biodiversity to Biotechnology".
Yu Z-C, Tang B-L, Zhao D-L, Pang X, Qin Q-L, Zhou B-C, Zhang X-Y, Chen X-L, Zhang Y-Z: Development of a cold-adapted pseudoalteromonas expression system for the pseudoalteromonas proteins intractable for the *Escherichia coli* system. PloS one (2015), 10:e0137384.
Nelson et al. (2007) Applied and Environmental Microbiology, vol. 73(6), pp. 1825-1833.
Sawabe et al. (2006) Letters in Applied Microbiology, vol. 43, pp. 514-522.
Ondrey and Visick (2014) The Open Microbiology Journal, vol. 8, pp. 122-129.
Klemetsen (2016) UiT Master's thesis.
Hjerde et al. (2015) BMC Genomics, 16:447.
A poster titled "Novel expression system specialized or psychrophilic enzymes". Presented at Norsk Biokjemisk Selslap meeting in Tromsø, Norway (Jan. 21-24, 2016).
A poster titled "Development of a novel expression host for challenging enzymes". Presented at BIOPROSP 2017 event in Tromsø, Norway (Sep. 3, 2017).

\* cited by examiner

SEQUENCE LISTING

<160> NUMBER OF SEQ ID NOS: 52

<210> SEQ ID NO 1
<211> LENGTH: 20
<212> TYPE: PRT
<213> ORGANISM: Artificial Sequence
<220> FEATURE:
<223> OTHER INFORMATION: fusion moiety sequence

<400> SEQUENCE: 1

Met Ser Lys Gln Met Lys Phe Gly Leu Leu Pro Ala Ala Ile Ala Gly
1               5                   10                  15

Ala Leu Leu Ser
            20

<210> SEQ ID NO 2
<211> LENGTH: 60
<212> TYPE: DNA
<213> ORGANISM: Artificial Sequence
<220> FEATURE:
<223> OTHER INFORMATION: fusion moiety sequence

<400> SEQUENCE: 2
atgagtaagc aaatgaagtt tggacttctt ccagcagcga tcgctggtgc attactgagc      60

<210> SEQ ID NO 3
<211> LENGTH: 300
<212> TYPE: DNA
<213> ORGANISM: Artificial Sequence
<220> FEATURE:
<223> OTHER INFORMATION: promoter sequence

<400> SEQUENCE: 3
tttactgata aaatggtcat ttattgtgtg aaatcacttt ttttgtggca cagacccctt      60
tttttaaata aaagccccta agtttaattg actttcatct gacaatagta tgaaattcac     120
actgctatca ctacttgaat aacattgttc tgacatagcg tttatggcat gaaatgttgg     180
acggtggtta agtttgtttt gttatatgtt aaggtttctt acatagacag actacgtgaa     240
gttggctaca agtcgatttg tataaaagat tttataaata tatatttgga gataaaaata     300

<210> SEQ ID NO 4
<211> LENGTH: 25
<212> TYPE: PRT
<213> ORGANISM: Artificial Sequence
<220> FEATURE:
<223> OTHER INFORMATION: fusion moiety sequence

<400> SEQUENCE: 4

Met Ser Lys Gln Met Lys Phe Gly Leu Leu Pro Ala Ala Ile Ala Gly
1               5                   10                  15

Ala Leu Leu Ser Gly Asn Ala Phe Ala
            20                  25

<210> SEQ ID NO 5
<211> LENGTH: 75
<212> TYPE: DNA
<213> ORGANISM: Artificial Sequence
<220> FEATURE:
<223> OTHER INFORMATION: fusion moiety sequence

<400> SEQUENCE: 5
atgagtaagc aaatgaagtt tggacttctt ccagcagcga tcgctggtgc attactgagc      60
ggcaacgcat tcgct                                                       75

<210> SEQ ID NO 6
<211> LENGTH: 18
<212> TYPE: DNA
<213> ORGANISM: Artificial Sequence
<220> FEATURE:
<223> OTHER INFORMATION: oligonucleotide

<400> SEQUENCE: 6
gtcgacctgc aggcatgc                                          18

<210> SEQ ID NO 7
<211> LENGTH: 20
<212> TYPE: DNA
<213> ORGANISM: Artificial Sequence
<220> FEATURE:
<223> OTHER INFORMATION: oligonucleotide

<400> SEQUENCE: 7
ggtgaaggga tcaattccct                                        20

<210> SEQ ID NO 8
<211> LENGTH: 31
<212> TYPE: DNA
<213> ORGANISM: Artificial Sequence
<220> FEATURE:
<223> OTHER INFORMATION: oligonucleotide

<400> SEQUENCE: 8
catgcttaat ttctcctctt taattagatc c                           31

<210> SEQ ID NO 9
<211> LENGTH: 40
<212> TYPE: DNA
<213> ORGANISM: Artificial Sequence
<220> FEATURE:
<223> OTHER INFORMATION: oligonucleotide

<400> SEQUENCE: 9
ggagaaatta agcatgatgc atcatcacca tcaccatggt                  40

<210> SEQ ID NO 10
<211> LENGTH: 40
<212> TYPE: DNA
<213> ORGANISM: Artificial Sequence
<220> FEATURE:
<223> OTHER INFORMATION: oligonucleotide

<400> SEQUENCE: 10
atgcctgcag gtcgactcat gatactaact gttgtacgta                  40

<210> SEQ ID NO 11
<211> LENGTH: 40
<212> TYPE: DNA
<213> ORGANISM: Artificial Sequence
<220> FEATURE:
<223> OTHER INFORMATION: oligonucleotide

<400> SEQUENCE: 11
ggagaaatta agcatgatgc atcatcacca tcaccatggt                  40

<210> SEQ ID NO 12
<211> LENGTH: 40
<212> TYPE: DNA
<213> ORGANISM: Artificial Sequence
<220> FEATURE:

<223> OTHER INFORMATION: oligonucleotide

<400> SEQUENCE: 12
atgcctgcag gtcgacttag aatagaccta attgagaagc                    40

<210> SEQ ID NO 13
<211> LENGTH: 40
<212> TYPE: DNA
<213> ORGANISM: Artificial Sequence
<220> FEATURE:
<223> OTHER INFORMATION: oligonucleotide

<400> SEQUENCE: 13
aattgatccc ttcaccatgg gcaaagtgag caagggcgag                    40

<210> SEQ ID NO 14
<211> LENGTH: 40
<212> TYPE: DNA
<213> ORGANISM: Artificial Sequence
<220> FEATURE:
<223> OTHER INFORMATION: oligonucleotide

<400> SEQUENCE: 14
atgcctgcag gtcgaccttg tacagctcgt ccatgccgag                    40

<210> SEQ ID NO 15
<211> LENGTH: 20
<212> TYPE: DNA
<213> ORGANISM: Artificial Sequence
<220> FEATURE:
<223> OTHER INFORMATION: oligonucleotide

<400> SEQUENCE: 15
gatctctgca gtacctgtga                                          20

<210> SEQ ID NO 16
<211> LENGTH: 22
<212> TYPE: DNA
<213> ORGANISM: Artificial Sequence
<220> FEATURE:
<223> OTHER INFORMATION: oligonucleotide

<400> SEQUENCE: 16
atgcatcatc accatcacca tg                                       22

<210> SEQ ID NO 17
<211> LENGTH: 40
<212> TYPE: DNA
<213> ORGANISM: Artificial Sequence
<220> FEATURE:
<223> OTHER INFORMATION: oligonucleotide

<400> SEQUENCE: 17
aggtactgca gagatcttta ctgataaaat ggtcatttat                    40

<210> SEQ ID NO 18
<211> LENGTH: 40
<212> TYPE: DNA
<213> ORGANISM: Artificial Sequence
<220> FEATURE:
<223> OTHER INFORMATION: oligonucleotide

<400> SEQUENCE: 18
gatggtgatg atgcattatt tttatctcca aatatatatt                    40

```
<210> SEQ ID NO 19
<211> LENGTH: 59
<212> TYPE: DNA
<213> ORGANISM: Artificial Sequence
<220> FEATURE:
<223> OTHER INFORMATION: oligonucleotide

<400> SEQUENCE: 19
gctgctggaa gaagtccaaa cttcatttgc ttactcatgc ttaatttctc ctctttaat      59

<210> SEQ ID NO 20
<211> LENGTH: 62
<212> TYPE: DNA
<213> ORGANISM: Artificial Sequence
<220> FEATURE:
<223> OTHER INFORMATION: oligonucleotide

<400> SEQUENCE: 20
gacttcttcc agcagcgatc gctggtgcat tactgagctt tcagggaatt gatcccttca      60
cc                                                                    62

<210> SEQ ID NO 21
<211> LENGTH: 39
<212> TYPE: DNA
<213> ORGANISM: Artificial Sequence
<220> FEATURE:
<223> OTHER INFORMATION: oligonucleotide

<400> SEQUENCE: 21
atggtgatgg tgatgatgct tgtacagctc gtccatgcc                            39

<210> SEQ ID NO 22
<211> LENGTH: 43
<212> TYPE: DNA
<213> ORGANISM: Artificial Sequence
<220> FEATURE:
<223> OTHER INFORMATION: oligonucleotide

<400> SEQUENCE: 22
catcatcacc atcaccatta acgacctgca ggcatgcaag ctt                       43

<210> SEQ ID NO 23
<211> LENGTH: 24
<212> TYPE: DNA
<213> ORGANISM: Artificial Sequence
<220> FEATURE:
<223> OTHER INFORMATION: oligonucleotide

<400> SEQUENCE: 23
gctcagtaat gcaccagcga tcgc                                            24

<210> SEQ ID NO 24
<211> LENGTH: 24
<212> TYPE: DNA
<213> ORGANISM: Artificial Sequence
<220> FEATURE:
<223> OTHER INFORMATION: oligonucleotide

<400> SEQUENCE: 24
catcatcacc atcaccatta agtc                                            24

<210> SEQ ID NO 25
<211> LENGTH: 40
<212> TYPE: DNA
<213> ORGANISM: Artificial Sequence
<220> FEATURE:
```

<223> OTHER INFORMATION: oligonucleotide

<400> SEQUENCE: 25
tggtgcatta ctgagccagc agaccaccca gaaaacacag                    40

<210> SEQ ID NO 26
<211> LENGTH: 40
<212> TYPE: DNA
<213> ORGANISM: Artificial Sequence
<220> FEATURE:
<223> OTHER INFORMATION: oligonucleotide

<400> SEQUENCE: 26
ggtgatggtg atgatgttag ccgcttgctt taatacgcca                    40

<210> SEQ ID NO 27
<211> LENGTH: 40
<212> TYPE: DNA
<213> ORGANISM: Artificial Sequence
<220> FEATURE:
<223> OTHER INFORMATION: oligonucleotide

<400> SEQUENCE: 27
tggtgcatta ctgagcggtc gtgcagttgt gtttgaagaa                    40

<210> SEQ ID NO 28
<211> LENGTH: 40
<212> TYPE: DNA
<213> ORGANISM: Artificial Sequence
<220> FEATURE:
<223> OTHER INFORMATION: oligonucleotide

<400> SEQUENCE: 28
ggtgatggtg atgatgtgca ccatcaggat gcggacgacg                    40

<210> SEQ ID NO 29
<211> LENGTH: 40
<212> TYPE: DNA
<213> ORGANISM: Artificial Sequence
<220> FEATURE:
<223> OTHER INFORMATION: oligonucleotide

<400> SEQUENCE: 29
tggtgcatta ctgagcgata acaattcgaa caaaacagca                    40

<210> SEQ ID NO 30
<211> LENGTH: 40
<212> TYPE: DNA
<213> ORGANISM: Artificial Sequence
<220> FEATURE:
<223> OTHER INFORMATION: oligonucleotide

<400> SEQUENCE: 30
ggtgatggtg atgatgtgcg ccaattattt tttgaccata                    40

<210> SEQ ID NO 31
<211> LENGTH: 40
<212> TYPE: DNA
<213> ORGANISM: Artificial Sequence
<220> FEATURE:
<223> OTHER INFORMATION: oligonucleotide

<400> SEQUENCE: 31
tggtgcatta ctgagcggtg atagcaccat gcgtgcagca                    40

-continued

<210> SEQ ID NO 32
<211> LENGTH: 40
<212> TYPE: DNA
<213> ORGANISM: Artificial Sequence
<220> FEATURE:
<223> OTHER INFORMATION: oligonucleotide

<400> SEQUENCE: 32
ggtgatggtg atgatgggcc atatccagaa caatacgacc                40

<210> SEQ ID NO 33
<211> LENGTH: 40
<212> TYPE: DNA
<213> ORGANISM: Artificial Sequence
<220> FEATURE:
<223> OTHER INFORMATION: oligonucleotide

<400> SEQUENCE: 33
tggtgcatta ctgagccagt ttagcgttct ggcaggtagc                40

<210> SEQ ID NO 34
<211> LENGTH: 40
<212> TYPE: DNA
<213> ORGANISM: Artificial Sequence
<220> FEATURE:
<223> OTHER INFORMATION: oligonucleotide

<400> SEQUENCE: 34
ggtgatggtg atgatgaaca ccaggctgac catccggcac                40

<210> SEQ ID NO 35
<211> LENGTH: 40
<212> TYPE: DNA
<213> ORGANISM: Artificial Sequence
<220> FEATURE:
<223> OTHER INFORMATION: oligonucleotide

<400> SEQUENCE: 35
aattgatccc ttcaccatgg ataacaattc gaacaaaaca                40

<210> SEQ ID NO 36
<211> LENGTH: 40
<212> TYPE: DNA
<213> ORGANISM: Artificial Sequence
<220> FEATURE:
<223> OTHER INFORMATION: oligonucleotide

<400> SEQUENCE: 36
atgcctgcag gtcgacttat gcgccaatta tttttgacc                 40

<210> SEQ ID NO 37
<211> LENGTH: 474
<212> TYPE: PRT
<213> ORGANISM: Aliivibrio salmonicida

<400> SEQUENCE: 37

Met Pro Gln Asp Asn Ala Pro Ser Phe Phe Phe Asp Tyr Glu Thr
1               5                   10                  15

Trp Gly Thr Ser Pro Ser Leu Asp Arg Pro Cys Gln Phe Ala Gly Val
                20                  25                  30

Arg Thr Asp Glu Asp Phe Asn Ile Ile Gly Glu Pro Leu Val Ile Tyr
            35                  40                  45

Cys Arg Pro Pro Ile Asp Tyr Leu Pro Ser Pro Glu Ala Cys Leu Ile
        50                  55                  60

```
Thr Gly Ile Thr Pro Gln Met Ala Val Ser Lys Gly Leu Ser Glu Pro
 65                  70                  75                  80

Glu Phe Ile Ala Gln Ile His Asn Glu Leu Ser Lys Pro Asn Thr Cys
                 85                  90                  95

Ser Leu Gly Tyr Asn Asn Ile Arg Phe Asp Asp Glu Val Ser Arg Tyr
                100                 105                 110

Thr Leu Tyr Arg Asn Phe Phe Glu Pro Tyr Gly Trp Ser Trp Gln Asn
            115                 120                 125

Gly Asn Ser Arg Trp Asp Leu Leu Asp Val Met Arg Ala Val Tyr Ala
        130                 135                 140

Leu Arg Pro Glu Gly Ile Glu Trp Pro Lys Asp Glu Glu Gly Lys Pro
145                 150                 155                 160

Ser Phe Arg Leu Glu Lys Leu Ser Gln Ala Asn Gly Ile Glu His Glu
                165                 170                 175

Asn Ala His Asp Ala Met Ala Asp Val Ile Ala Thr Ile Glu Leu Ala
            180                 185                 190

Lys Val Val Lys Lys Ala Gln Pro Lys Met Phe Asn Tyr Leu Leu Ser
        195                 200                 205

Met Arg His Lys Lys Lys Ala Ala Thr Leu Ile Asp Ile Ile Glu Met
210                 215                 220

Thr Pro Leu Met His Val Ser Gly Met Phe Gly Val Asp Arg Gly Asn
225                 230                 235                 240

Ile Ser Trp Ile Val Pro Val Ala Trp His Pro Thr Asn Asn Asn Ala
                245                 250                 255

Val Ile Thr Ile Asp Leu Ala Leu Asp Pro Ala Val Phe Leu Glu Leu
            260                 265                 270

Asp Ala Glu Gln Leu His Gln Arg Met Tyr Thr Lys Arg Ser Glu Leu
        275                 280                 285

Gly Pro Asp Glu Leu Pro Val Pro Val Lys Leu Val His Leu Asn Lys
        290                 295                 300

Cys Pro Ile Leu Ala Pro Ala Lys Thr Leu Thr Ala Glu Asn Ala Ile
305                 310                 315                 320

Ala Leu Asn Val Asp Arg Glu Ala Cys Leu Arg Asn Leu Lys Val Ile
                325                 330                 335

Arg Glu Asn Pro Glu Ile Arg Gln Lys Leu Ile Asp Leu Tyr Asn Ile
                340                 345                 350

Glu Pro Gly Tyr Glu Lys Ser Ser Asn Val Asp Thr Leu Leu Tyr Asp
            355                 360                 365

Gly Phe Phe Ser His Ala Asp Lys Thr Ala Ile Asp Met Ile Arg Gln
        370                 375                 380

Ser Thr Pro Glu Gln Leu Ile Asp Phe Glu Pro Asn Val Ser Asp Pro
385                 390                 395                 400

Arg Ile Lys Pro Leu Leu Phe Arg Tyr Arg Ala Arg Asn Phe Pro His
                405                 410                 415

Thr Leu Asn Glu Ser Glu Gln Leu Arg Trp Gln Ala His Leu Gln Asp
            420                 425                 430

Tyr Phe Glu Thr His Met Ser Asp Tyr Glu Thr Arg Phe Glu Ser Leu
        435                 440                 445

Tyr Leu Glu Ser Glu Gly Asn Glu Lys Lys Thr Ala Ile Leu Arg Ala
        450                 455                 460

Val Tyr Asn Tyr Val Gln Gln Leu Val Ser
465                 470
```

<210> SEQ ID NO 38
<211> LENGTH: 789
<212> TYPE: PRT
<213> ORGANISM: Aliivibrio salmonicida

<400> SEQUENCE: 38

```
Leu Asn Ser Pro His Cys Gly Phe Leu Leu Thr Arg Gln Asn Lys Asp
1               5                   10                  15

Ile Arg Asp His Ser Leu Val Asp Leu Trp Val Lys Cys Asp Asp His
            20                  25                  30

Ile Ala His Leu Leu Ile Glu Asn Glu Leu Ala Val Ile Phe Phe Leu
        35                  40                  45

Lys Glu Arg Gln Ala Glu Tyr Glu Ser Ile Leu Thr Asn Ala His Ile
50                  55                  60

His Tyr Ser Ile Lys Ser Thr Ser Leu His Thr Phe Gln His Gln Pro
65                  70                  75                  80

Val Phe Gly Leu Tyr Phe Ser Ser Thr Gln Gln Lys Arg Val Ala Thr
                85                  90                  95

Ala Leu Phe Glu Asp His Gln Leu Pro Thr Phe Glu Gly Asp Ile Arg
            100                 105                 110

Leu Ala Asp Arg Tyr Leu Met Glu Arg Phe Ile Cys Gly Gly Met Ala
        115                 120                 125

Phe Val Gly Thr Pro Arg Gln Arg Lys Gly Tyr Val Glu Tyr Arg Asp
130                 135                 140

Val Lys Ile Lys Ser Ala Glu Met Thr Pro Glu Phe Ser Val Val Ser
145                 150                 155                 160

Leu Asp Val Glu Cys Ser Glu Lys Gly Ile Leu Tyr Ser Val Ala Leu
                165                 170                 175

His Cys Glu Arg Asp Thr Arg Ile Ile Met Val Gly Pro Glu Glu Thr
            180                 185                 190

Ser Asp Leu Pro Ile Glu Trp Val Glu Asn Glu Lys Ala Leu Leu Leu
        195                 200                 205

Ala Leu Glu Ser Trp Phe Gln Thr Phe Asp Pro Asp Ile Ile Ile Gly
210                 215                 220

Trp Asn Val Ile Asn Phe Asp Phe Asn Leu Leu Ile Lys Arg Ala Lys
225                 230                 235                 240

Trp His Asn Leu Ala Phe Arg Leu Gly Arg Gly Asn Ser Ser Leu Tyr
                245                 250                 255

Phe Arg Glu Ser Asn Lys Asn Arg Gln Gln Gly Phe Leu Ser Phe Pro
            260                 265                 270

Gly Arg Val Val Leu Asp Gly Ile Asp Ala Leu Lys Thr Ala Thr Tyr
        275                 280                 285

His Phe Ser Ser Trp Ser Leu Glu Ser Val Ser Gln Glu Leu Leu Asn
290                 295                 300

Glu Gly Lys Ser Ile His Asp Pro Ser Asp Arg Met Gly Glu Ile Asn
305                 310                 315                 320

Arg Met Tyr Arg Glu Asp Lys Cys Ala Leu Ala Lys Tyr Asn Leu Gln
                325                 330                 335

Asp Cys Val Leu Val Thr Arg Ile Phe Glu Leu Thr His Leu Leu Glu
            340                 345                 350

Phe Val Ile Glu Arg Thr Lys Leu Thr Gly Ile Glu Leu Asp Arg Val
        355                 360                 365

Gly Gly Ser Val Ala Ala Phe Thr Asn Leu Tyr Leu Pro Arg Leu His
370                 375                 380
```

```
Arg Ala Gly Tyr Ile Ala Pro Asn Leu Glu Ser Glu Asn Trp Ile Ala
385                 390                 395                 400

Ser Pro Gly Gly Tyr Val Met Ser Ser Lys Pro Gly Leu Tyr Glu Ser
                405                 410                 415

Val Leu Val Leu Asp Phe Lys Ser Leu Tyr Pro Ser Ile Ile Lys Thr
            420                 425                 430

Phe Arg Ile Asp Pro Leu Gly Leu Val Glu Gly Leu Lys Leu Glu Ser
        435                 440                 445

Gly Ile Asp Asp Gly Gln Ala Ile Glu Gly Phe Arg Gly Gly Arg Phe
    450                 455                 460

His Arg Thr Lys His Phe Leu Pro Asn Leu Ile Glu Thr Leu Trp Ser
465                 470                 475                 480

Ala Arg Asp Val Ala Lys Lys Asn Asn Glu Lys Ala Phe Ser Gln Ala
                485                 490                 495

Ile Lys Ile Ile Met Asn Ser Phe Tyr Gly Val Leu Gly Ser Ser Gly
            500                 505                 510

Cys Arg Phe Phe Asp His Arg Leu Ala Ser Ser Ile Thr Met Arg Gly
        515                 520                 525

His Glu Ile Met Lys Thr Thr Arg Glu Leu Ile Glu Ser Gln Gly Tyr
    530                 535                 540

Glu Val Ile Tyr Gly Asp Thr Asp Ser Thr Phe Val Thr Leu Gly Glu
545                 550                 555                 560

Ser Met Pro Ser Asp Glu Ala Asp Lys Ile Gly Lys Gln Leu Val Asp
                565                 570                 575

His Ile Asn Gln Trp Trp Thr Ala His Leu Glu Ser Glu Tyr Ala Ile
            580                 585                 590

Asp Ser Ala Leu Glu Ile Glu Tyr Glu Thr His Tyr Arg Ile Phe Leu
        595                 600                 605

Met Pro Thr Ile Arg Gly Ser Glu Met Gly Ser Lys Lys Arg Tyr Ala
    610                 615                 620

Gly Leu Ile Arg Lys Gly Asp Lys Glu Ile Ile Phe Lys Gly Leu
625                 630                 635                 640

Glu Thr Val Arg Thr Asp Trp Thr Pro Leu Ser Gln Glu Phe Gln Lys
                645                 650                 655

Val Leu Phe Asp Lys Val Phe His Gln Gln Ala Val Glu Glu Tyr Val
            660                 665                 670

Arg Glu Tyr Val Asp Lys Thr Lys Ser Gly Glu Phe Asp Asn Lys Leu
        675                 680                 685

Ile Tyr Arg Lys Arg Leu Arg Arg Gln Leu Asp Glu Tyr Gln Lys Asn
    690                 695                 700

Val Pro Pro His Val Lys Ala Ala Arg Ile Ala Asp Thr Gln Asn Gln
705                 710                 715                 720

Lys Leu Gly Lys Pro Leu Met Tyr Gln Gln Gly Gly Trp Ile Glu Tyr
                725                 730                 735

Ile Ile Thr Thr Ala Gly Pro Glu Pro Ile Glu Tyr Arg Gln Asn Pro
            740                 745                 750

Ile Asp Tyr Asp His Tyr Val Glu Lys Gln Leu Lys Pro Ile Ala Glu
        755                 760                 765

Gly Ile Leu Pro Phe Val Asn Leu Ser Phe Thr Glu Leu Ser Ala Ser
    770                 775                 780

Gln Leu Gly Leu Phe
785
```

```
<210> SEQ ID NO 39
<211> LENGTH: 480
<212> TYPE: PRT
<213> ORGANISM: Moritella viscosa

<400> SEQUENCE: 39
```

| Met | Asp | Asn | Asn | Ser | Asn | Lys | Thr | Ala | Thr | Asp | Leu | Pro | Thr | Phe | Tyr |
|---|---|---|---|---|---|---|---|---|---|---|---|---|---|---|---|
| 1 | | | | 5 | | | | | 10 | | | | | 15 | |

| Trp | His | Asp | Tyr | Glu | Thr | Phe | Gly | Leu | Ser | Pro | Ser | Leu | Asp | Arg | Pro |
|---|---|---|---|---|---|---|---|---|---|---|---|---|---|---|---|
| | | | 20 | | | | | 25 | | | | | 30 | | |

| Ser | Gln | Phe | Ala | Gly | Ile | Arg | Thr | Asp | Met | Asp | Phe | Asn | Val | Ile | Gly |
|---|---|---|---|---|---|---|---|---|---|---|---|---|---|---|---|
| | | | 35 | | | | | 40 | | | | | 45 | | |

| Glu | Pro | Asp | Met | Phe | Tyr | Cys | Arg | Gln | Ser | Asp | Asp | Tyr | Leu | Pro | Ser |
|---|---|---|---|---|---|---|---|---|---|---|---|---|---|---|---|
| | 50 | | | | | 55 | | | | | 60 | | | | |

| Pro | Glu | Ala | Ala | Met | Ile | Thr | Gly | Ile | Thr | Pro | Gln | Lys | Thr | Gln | Ala |
|---|---|---|---|---|---|---|---|---|---|---|---|---|---|---|---|
| 65 | | | | | 70 | | | | | 75 | | | | | 80 |

| Glu | Gly | Val | Ser | Glu | Ala | Glu | Phe | Ser | Lys | Arg | Ile | Glu | Ala | Gln | Phe |
|---|---|---|---|---|---|---|---|---|---|---|---|---|---|---|---|
| | | | | 85 | | | | | 90 | | | | | 95 | |

| Ser | Gln | Lys | Asn | Thr | Cys | Ile | Ile | Gly | Tyr | Asn | Asn | Ile | Arg | Phe | Asp |
|---|---|---|---|---|---|---|---|---|---|---|---|---|---|---|---|
| | | | | 100 | | | | | 105 | | | | | 110 | |

| Asp | Glu | Val | Thr | Arg | Asn | Ile | Phe | Tyr | Arg | Asn | Phe | Tyr | Asp | Pro | Tyr |
|---|---|---|---|---|---|---|---|---|---|---|---|---|---|---|---|
| | | | 115 | | | | | 120 | | | | | 125 | | |

| Ala | His | Thr | Trp | Lys | Asp | Gly | Asn | Ser | Arg | Trp | Asp | Ile | Ile | Asp | Leu |
|---|---|---|---|---|---|---|---|---|---|---|---|---|---|---|---|
| | 130 | | | | | 135 | | | | | 140 | | | | |

| Met | Arg | Ala | Cys | Tyr | Ala | Leu | Arg | Pro | Glu | Gly | Ile | Val | Trp | Pro | Glu |
|---|---|---|---|---|---|---|---|---|---|---|---|---|---|---|---|
| 145 | | | | | 150 | | | | | 155 | | | | | 160 |

| Asn | Asp | Asp | Gly | Leu | Pro | Ser | Met | Arg | Leu | Glu | Leu | Leu | Thr | Ala | Ala |
|---|---|---|---|---|---|---|---|---|---|---|---|---|---|---|---|
| | | | | 165 | | | | | 170 | | | | | 175 | |

| Asn | Gly | Ile | Glu | His | Ala | Asn | Ala | His | Asp | Ala | Thr | Ser | Asp | Val | Tyr |
|---|---|---|---|---|---|---|---|---|---|---|---|---|---|---|---|
| | | | 180 | | | | | 185 | | | | | 190 | | |

| Ala | Thr | Ile | Ala | Met | Ala | Lys | Leu | Val | Lys | Glu | Lys | Gln | Pro | Lys | Leu |
|---|---|---|---|---|---|---|---|---|---|---|---|---|---|---|---|
| | | 195 | | | | | 200 | | | | | 205 | | | |

| Phe | Asp | Phe | Leu | Phe | Asn | Leu | Arg | Ser | Lys | Arg | Lys | Val | Glu | Ser | Leu |
|---|---|---|---|---|---|---|---|---|---|---|---|---|---|---|---|
| | 210 | | | | | 215 | | | | | 220 | | | | |

| Val | Asp | Ile | Ile | Asn | Met | Thr | Pro | Leu | Val | His | Val | Ser | Gly | Met | Phe |
|---|---|---|---|---|---|---|---|---|---|---|---|---|---|---|---|
| 225 | | | | | 230 | | | | | 235 | | | | | 240 |

| Gly | Ala | Asp | Arg | Gly | Phe | Thr | Ser | Trp | Val | Val | Pro | Leu | Ala | Trp | His |
|---|---|---|---|---|---|---|---|---|---|---|---|---|---|---|---|
| | | | | 245 | | | | | 250 | | | | | 255 | |

| Pro | Thr | Asn | Asn | Asn | Ala | Val | Ile | Val | Ala | Asp | Leu | Ala | Gln | Asp | Ile |
|---|---|---|---|---|---|---|---|---|---|---|---|---|---|---|---|
| | | | 260 | | | | | 265 | | | | | 270 | | |

| Thr | Pro | Leu | Leu | Glu | Leu | Ser | Ala | Asp | Glu | Leu | Arg | Glu | Arg | Leu | Tyr |
|---|---|---|---|---|---|---|---|---|---|---|---|---|---|---|---|
| | | 275 | | | | | 280 | | | | | 285 | | | |

| Thr | Pro | Lys | Lys | Asp | Leu | Gly | Asp | Leu | Thr | Pro | Ile | Pro | Leu | Lys | Leu |
|---|---|---|---|---|---|---|---|---|---|---|---|---|---|---|---|
| | 290 | | | | | 295 | | | | | 300 | | | | |

| Ile | His | Ile | Asn | Lys | Cys | Pro | Val | Leu | Ala | Pro | Ala | Lys | Thr | Leu | Leu |
|---|---|---|---|---|---|---|---|---|---|---|---|---|---|---|---|
| 305 | | | | | 310 | | | | | 315 | | | | | 320 |

| Pro | Glu | Asn | Ala | Glu | Arg | Leu | Gly | Ile | Asp | Arg | Ser | Ala | Cys | Leu | Ala |
|---|---|---|---|---|---|---|---|---|---|---|---|---|---|---|---|
| | | | | 325 | | | | | 330 | | | | | 335 | |

| Asn | Leu | Lys | Arg | Leu | Lys | Glu | Ser | Ala | Thr | Leu | Arg | Glu | Asn | Val | Val |
|---|---|---|---|---|---|---|---|---|---|---|---|---|---|---|---|
| | | | 340 | | | | | 345 | | | | | 350 | | |

| Gly | Val | Tyr | Gln | Val | Glu | Arg | Glu | Tyr | Pro | Lys | Ser | Thr | Asn | Val | Asp |
|---|---|---|---|---|---|---|---|---|---|---|---|---|---|---|---|
| | | 355 | | | | | 360 | | | | | 365 | | | |

| Ala | Met | Ile | Tyr | Asp | Gly | Phe | Phe | Ser | Ala | Gly | Asp | Lys | Ala | Asn | Phe |
|---|---|---|---|---|---|---|---|---|---|---|---|---|---|---|---|
| | 370 | | | | | 375 | | | | | 380 | | | | |

```
Glu Ile Leu Arg Glu Thr Ala Pro Glu Gln Leu Thr Gly Leu Gln Leu
385                 390                 395                 400

Lys Val Ser Asp Ser Arg Phe Asn Glu Leu Phe Phe Arg Tyr Arg Ala
            405                 410                 415

Arg Asn Phe Pro His Leu Leu Ser Met Pro Glu Gln Gln Lys Trp Leu
        420                 425                 430

Asp His Cys Arg Thr Val Leu Glu Asp Ser Ala Pro Ala Tyr Phe Ala
    435                 440                 445

Arg Leu Asp Ala Leu Ala Ile Glu Asn Ser His Asp Glu Arg Lys Met
450                 455                 460

Lys Leu Leu Gln Gln Leu Tyr Leu Tyr Gly Gln Lys Ile Ile Gly Ala
465                 470                 475                 480

<210> SEQ ID NO 40
<211> LENGTH: 588
<212> TYPE: PRT
<213> ORGANISM: Cenarchaeum symbiosum

<400> SEQUENCE: 40

Gln Phe Ser Val Leu Ala Gly Ser Leu Glu Lys Met Glu Ser Thr Ala
1               5                   10                  15

Lys Arg Leu Glu Leu Thr Gly Ile Leu Glu Glu Leu Leu Arg Glu Thr
            20                  25                  30

Pro His Glu Val Ile Ala Gln Ile Val Tyr Leu Ile Gln Gly Lys Leu
        35                  40                  45

Arg Pro Glu Phe Glu Gly Ile Glu Leu Gly Val Ala Glu Lys Leu Ala
    50                  55                  60

Val Arg Ala Val Ser Lys Ser Ser Gly Met Pro Ala Ala Arg Ile Glu
65                  70                  75                  80

Ala Ala Tyr Arg Arg Asp Gly Asp Leu Gly Arg Ala Ser Ser Ile
                85                  90                  95

Leu Glu Gln Lys Thr Gln Thr Thr Phe Leu Ala Glu Glu Ile Thr Val
            100                 105                 110

Glu Arg Val Tyr Asp Thr Leu Met Arg Ile Ala Arg Leu Glu Gly Ala
        115                 120                 125

Arg Ser Gln Asp Met Lys Met Arg His Ile Ser Ser Leu Leu Asn Asp
    130                 135                 140

Ala Ser Pro Arg Asp Ala Cys Tyr Ile Leu Lys Leu Ile Leu Gly Thr
145                 150                 155                 160

Leu Arg Leu Gly Ile Ala Glu Asn Thr Val Met Asp Ala Leu Ala Ala
                165                 170                 175

Ala Phe Thr Gly Ser Lys Ser Asn Arg Pro Glu Leu Glu Arg Ala Tyr
            180                 185                 190

Asn Val Ser Ser Asp Leu Gly Arg Val Ala Glu Ala Val Ser Ser Gly
        195                 200                 205

Gly Leu Glu Ala Val Arg Gly Phe Ala Val Ala Val Phe Ser Pro Ile
    210                 215                 220

Arg Pro Met Leu Ala Asp Arg Val Arg Ser Glu Ser Glu Ala Leu Glu
225                 230                 235                 240

Lys Met Gly Ala Gly Leu Ala Ala Glu Tyr Lys Leu Asp Gly Glu Arg
                245                 250                 255

Val Gln Val His Leu Ser Gly Gly Arg Val Glu Leu Phe Ser Arg Ser
            260                 265                 270

Leu Glu Asn Ile Thr Ala Tyr Tyr Pro Asp Ile Val Glu Arg Ile Pro
        275                 280                 285
```

Gly Arg Leu Arg Ala Arg Glu Ala Val Leu Glu Ala Glu Val Ala
            290                 295                 300

Val Asn Glu Glu Thr Gly Glu Phe Leu Pro Phe Gln Glu Leu Met His
305                 310                 315                 320

Arg Arg Arg Lys Tyr Asp Ile Asp Lys Ala Val Met Arg Tyr Pro Ile
                325                 330                 335

Thr Val Asn Phe Phe Asp Ile Leu Tyr Leu Asp Gly Arg Asp Cys Leu
            340                 345                 350

Gly Ile Ser Tyr Ser Glu Arg Arg Ala Leu Leu Glu Gly Val Val Asp
            355                 360                 365

Glu Asp Ser Phe Ala Arg Cys Val Pro Val Ser Thr Ile Pro Asp Glu
370                 375                 380

Ser Ala Leu Glu Asp Ser Leu Glu Asn Ser Ile Asn Ala Gly Cys Glu
385                 390                 395                 400

Gly Leu Met Leu Lys Leu Pro Asp Ala Pro Tyr Arg Ala Gly Ser Arg
            405                 410                 415

Gly Gly Tyr Trp Leu Lys Leu Lys Arg Glu Tyr Arg Asn Glu Leu Gly
            420                 425                 430

Asp Ser Leu Asp Leu Val Ile Ile Gly Ala Phe Phe Gly Lys Gly Arg
            435                 440                 445

Arg Thr Gly Arg Tyr Gly Thr Leu Leu Leu Ala Thr Tyr Asp Asp Ser
450                 455                 460

Arg Asp Thr Phe Pro Ser Ile Cys Lys Val Gly Thr Gly Phe Thr Asp
465                 470                 475                 480

Glu Asp Leu Asp Gln Leu Tyr Gln Leu Leu Ser Pro Arg Val Thr Leu
            485                 490                 495

Lys Arg Asn Pro Arg Ile Asp Ser Gly Met Glu Ala Asp Val Trp Phe
            500                 505                 510

Asp Pro Glu Val Val Met Glu Val Ala Ser Glu Ile Thr Leu Ser
            515                 520                 525

Pro Val His Lys Thr Ala Leu Asp Ser Val Arg Lys Gly Ala Gly Leu
            530                 535                 540

Ala Leu Arg Phe Pro Lys Phe Thr Gly Lys Leu Arg Thr Glu Lys Thr
545                 550                 555                 560

Ala Glu Asp Ala Ser Thr Asp Gln Glu Val Ile Ala Leu Tyr Lys Ser
                565                 570                 575

Gln Lys Lys Val Val Pro Asp Gly Gln Pro Gly Val
            580                 585

<210> SEQ ID NO 41
<211> LENGTH: 270
<212> TYPE: PRT
<213> ORGANISM: Colwellia psychrerythraea

<400> SEQUENCE: 41

Gln Gln Thr Thr Gln Lys Thr Gln Lys Phe Lys Pro Asn Ile Gln His
1               5                   10                  15

Gly Val Ser Tyr Gln Lys Val Asp Asp Ile Ser Gln Tyr Tyr Val Ser
            20                  25                  30

Glu Lys Leu Asp Gly Ile Arg Gly Tyr Trp Asp Gly Lys Gln Leu Phe
        35                  40                  45

Thr Arg Arg Gly Asn Leu Ile Asn Ser Pro Ser Trp Phe Thr Gln His
    50                  55                  60

Trp Pro Thr Tyr Pro Met Asp Gly Glu Leu Trp Leu Ala Arg Gly Gln

```
                65                  70                  75                  80

Phe Gln Leu Leu Leu Ser Cys Ala Thr Lys Arg Ile Ala Val Glu Asn
                        85                  90                  95

Lys Thr Thr Ser Cys Trp Arg Ser Val Arg Phe Met Ile Phe Asp Leu
                       100                 105                 110

Pro Lys His Leu Gly Asp Phe Asn Glu Arg Val Ile Lys Met Arg Thr
                       115                 120                 125

Leu Leu Val Gln Asn Gln Ser Val Tyr Leu Ala Met Ile Asp Gln Val
                       130                 135                 140

Lys Leu Glu Glu Leu Ser Ala Leu Asp His Lys Leu Asp Glu Val Ile
        145                 150                 155                 160

Ala Thr His Gly Glu Gly Leu Met Leu His Leu Ala Ser Ala His Tyr
                           165                 170                 175

Gln Gln Gly Arg Asn Pro Ala Leu Met Lys Leu Lys Lys Tyr Gln Asp
                       180                 185                 190

Ala Glu Ala Thr Val Ile Gly Tyr Thr Glu Gly Lys Gly Lys Tyr Gln
                       195                 200                 205

Asn Gln Leu Gly Ala Ile Lys Val Lys Thr Ser Asp Gly Ile Ile Phe
                       210                 215                 220

Lys Ile Gly Ser Gly Leu Ser Asp Ile Gln Arg Ala Asn Pro Pro Lys
        225                 230                 235                 240

Ile Gly Thr Ile Ile Thr Phe Lys Tyr Asn Gly Leu Thr Gln Ala Gly
                           245                 250                 255

Ile Pro Arg Phe Ala Arg Phe Trp Arg Ile Lys Ala Ser Gly
                       260                 265                 270

<210> SEQ ID NO 42
<211> LENGTH: 358
<212> TYPE: PRT
<213> ORGANISM: Streptomyces

<400> SEQUENCE: 42

Met Gly Arg Ala Val Val Phe Glu Glu Phe Gly Lys Glu Ala Arg Val
        1                5                  10                  15

Gln Asp Val Ala Asp Pro Ser Pro Ser Arg Asp Gly Val Val Val Arg
                        20                  25                  30

Val Glu Ala Thr Gly Leu Cys Arg Ser Asp Trp His Gly Trp Met Gly
                        35                  40                  45

His Asp Pro Asp Ile Thr Leu Pro His Val Pro Gly His Glu Leu Ala
                    50                  55                  60

Gly Val Val Glu Ala Val Gly Arg Asp Val Val Asp Arg Arg Pro Gly
        65                  70                  75                  80

Asp Arg Val Thr Val Pro Phe Val Cys Ala Cys Gly Arg Cys Ala Ala
                        85                  90                  95

Cys Ala Ala Gly Ala Gln Gln Val Cys Glu Arg Gln Thr Gln Pro Gly
                       100                 105                 110

Phe Thr His Trp Gly Ser Phe Ala Glu Tyr Val Ala Leu Glu Arg Ala
                       115                 120                 125

Asp Val Asn Leu Val Pro Val Pro His Gly Met Ser Phe Gly Thr Ala
                       130                 135                 140

Ala Ala Leu Gly Cys Arg Phe Ala Thr Ala Phe Arg Ala Val Val Ala
        145                 150                 155                 160

Arg Gly Arg Val Ala Pro Gly Glu Trp Val Ala Val His Gly Cys Gly
                           165                 170                 175
```

```
Gly Ala Gly Leu Ser Ala Val Met Ile Ala Val Ala Cys Gly Ala Arg
            180                 185                 190

Val Val Ala Val Asp Val Ser Pro Glu Ala Leu Arg Leu Ala Arg Thr
        195                 200                 205

Phe Gly Ala Ala Glu Cys Val Asp Ala Ser Ala His Pro Glu Gly Val
    210                 215                 220

Asp Ala Ala Val Arg Glu Leu Thr Gly Gly Gly Ala Gln Leu Ser Leu
225                 230                 235                 240

Asp Ala Leu Gly Ser Pro Val Thr Cys Ala Ala Ser Val Arg Ser Leu
                245                 250                 255

Arg Arg Gln Gly Arg His Val Gln Val Gly Leu Leu Pro Pro Ala Ala
                260                 265                 270

Gly Asp Pro Val Val Pro Met Ala Arg Val Ile Ala Leu Glu Leu Glu
            275                 280                 285

Leu Leu Gly Ser His Gly Met Ala Ala His Ala Tyr Pro Pro Met Met
        290                 295                 300

Asp Met Val Arg Ser Gly Ser Leu Arg Pro Asp Leu Leu Val Thr Ser
305                 310                 315                 320

Thr Ile Gly Leu Asp Ala Ala Pro Ala Ala Leu Ala Ala Met Ser Ala
                325                 330                 335

Gly Pro Gly Pro Gly Ala Gly Val Thr Val Ile Glu Pro Thr Arg Arg
            340                 345                 350

Pro His Pro Asp Gly Ala
            355

<210> SEQ ID NO 43
<211> LENGTH: 23
<212> TYPE: DNA
<213> ORGANISM: Artificial Sequence
<220> FEATURE:
<223> OTHER INFORMATION: oligonucleotide

<400> SEQUENCE: 43
attaggtacc cgccgcgctt aat                                         23

<210> SEQ ID NO 44
<211> LENGTH: 25
<212> TYPE: DNA
<213> ORGANISM: Artificial Sequence
<220> FEATURE:
<223> OTHER INFORMATION: oligonucleotide

<400> SEQUENCE: 44
taatgcatgc gaaattaata cgact                                       25

<210> SEQ ID NO 45
<211> LENGTH: 15
<212> TYPE: DNA
<213> ORGANISM: Artificial Sequence
<220> FEATURE:
<223> OTHER INFORMATION: molecular beacon substrate
<220> FEATURE:
<221> NAME/KEY: misc_feature
<222> LOCATION: (1)..(1)
<223> OTHER INFORMATION: labelled at 5' end with the FAM fluorophore
<220> FEATURE:
<221> NAME/KEY: misc_feature
<222> LOCATION: (15)..(15)
<223> OTHER INFORMATION: labelled at 3' end with the TAMRA quencher

<400> SEQUENCE: 45
cgccatcgga ggttc                                                  15
```

-continued

<210> SEQ ID NO 46
<211> LENGTH: 82
<212> TYPE: DNA
<213> ORGANISM: Artificial Sequence
<220> FEATURE:
<223> OTHER INFORMATION: molecular beacon probe
<220> FEATURE:
<221> NAME/KEY: misc_feature
<222> LOCATION: (7)..(7)
<223> OTHER INFORMATION: labelled with the Dabcyl fluorophore
<220> FEATURE:
<221> NAME/KEY: misc_feature
<222> LOCATION: (32)..(32)
<223> OTHER INFORMATION: labelled with the FAM fluorophore

<400> SEQUENCE: 46
ggcccgtagg aggaaaggac atcttctagc atacgggccg tcaagttcat ggccagtcaa    60
gtcgtcagaa atttcgcacc ac                                            82

<210> SEQ ID NO 47
<211> LENGTH: 19
<212> TYPE: DNA
<213> ORGANISM: Artificial Sequence
<220> FEATURE:
<223> OTHER INFORMATION: primer

<400> SEQUENCE: 47
gtggtgcgaa atttctgac                                                19

<210> SEQ ID NO 48
<211> LENGTH: 586
<212> TYPE: PRT
<213> ORGANISM: Aliivibrio wodanis

<400> SEQUENCE: 48

Met Ser Lys Gln Met Lys Phe Gly Leu Leu Pro Ala Ala Ile Ala Gly
1               5                   10                  15

Ala Leu Leu Ser Gly Asn Ala Phe Ala Gly Thr Glu Ala Cys Ile Glu
            20                  25                  30

Val Phe Lys Ser Ala Ala Asn Asp Tyr Gln Glu His Asn Val Leu Tyr
        35                  40                  45

Thr Ala Ala Ser Cys Asn Phe Ala Thr Val Gly Gly Thr Thr Ala Asn
    50                  55                  60

Ser Leu Arg Ala Asn Asp Ser Ala Asp Ile Ala Tyr Glu Leu Thr Lys
65                  70                  75                  80

Asn Leu Asp Leu Asn Phe Glu Ala Val Asp Gln Asp Ala Ala Glu
            85                  90                  95

Thr Leu Asn Ile Val Tyr Val Pro Thr Ser Asp Ile Pro Ala Ala Ser
            100                 105                 110

Arg Leu Lys Phe Arg Leu Asn Gly Ala Thr Phe Ala Asn Asn Ser Asn
        115                 120                 125

Ile Ile Tyr Leu Val Lys Ala Glu Asp Ser Ala Thr Gly Ile Thr
    130                 135                 140

Thr Lys Tyr Ser Ala Val Ala Ser Thr Asp Gly Ala Val Asp Gly Glu
145                 150                 155                 160

Asn Val Ile Thr Phe Ile Val Thr Asp Leu Ile Gly Ala Gly Thr Arg
                165                 170                 175

Leu Val Leu Ser Leu Glu Asn Gln Pro Thr Leu Asp Leu Thr Gly Ala
            180                 185                 190

Val Glu Asn Arg Thr Thr Phe Glu Ser Pro Ala Ile Asn Ile Ala Asn
            195                 200                 205

Pro Glu Val Cys Thr Pro Asn Asp Lys Val Thr Leu Glu Val Ile Glu
210                 215                 220

Ala Lys Ser Asp Phe Gly Gln Asp Ile Lys Gly Ala Val Thr Asn Pro
225                 230                 235                 240

Ala Thr Asn Lys Leu Ala Asp Leu Val Asp Ile Gln Lys Gln Phe Thr
            245                 250                 255

Leu Leu His Asp Ala Gln Leu Thr Thr Glu Ala Leu Val Asp Ala Glu
        260                 265                 270

Ser Pro Ser Tyr Arg Gly Gln Phe Val Phe Ser Lys Thr Asp Thr Gly
    275                 280                 285

Leu Trp Val Asn Gln Thr Thr Glu Gln Gly Leu Phe Trp Glu Ser Thr
290                 295                 300

Ile Gln Asn Lys Ile Ser Ser Leu Asp Gln Tyr Val Glu Ile Asp Thr
305                 310                 315                 320

Glu Asp Arg Leu Arg Val Arg Leu Asn Pro Glu Gly Ser Leu Gly Gly
            325                 330                 335

Val Met Asn Phe Ala Met Leu Tyr Asn Asp Thr Thr Arg Ala Asn Thr
        340                 345                 350

Pro Leu Asp Ala Ser Glu Asp Ser His Ile Ser Thr Glu Ala Gln Tyr
    355                 360                 365

Met Tyr Asn Tyr Asn Thr Thr Gly Asn Arg Trp Thr Asn Val Lys Asp
370                 375                 380

Thr Ala Gln Glu Tyr Ser Tyr Asn Ile Tyr Asp Val Val Asn Gly Glu
385                 390                 395                 400

Asp Ser Ala Arg Ile Ala Met Gln Leu Glu Gly Asn Gly Gln Pro Met
            405                 410                 415

Ser Phe Asn Tyr Leu Leu Asn Ala Ser Leu Gly Leu Glu Phe Lys Asp
        420                 425                 430

Val Lys Leu Gln Asp Asp Thr Tyr Cys Gln Thr Lys Thr Pro Phe Lys
    435                 440                 445

Val Gly Val Asn Gly Ala Thr Leu Lys Val Pro His Thr Thr Asn Asn
450                 455                 460

Pro Ala Asn Phe Val Arg Ile Thr Asn Glu His Val Thr Gly Ala Glu
465                 470                 475                 480

Val Ser Val Thr Val Phe Asp Glu Asn Ser Thr Thr Ala Ala Asn Glu
            485                 490                 495

Ile Thr Phe Val Leu Asn Ala Glu Asn Gly Phe Ser Glu Glu Leu Gly
        500                 505                 510

Pro Lys Asp Ser Ile Val Tyr Lys Ser Asp Lys Ile Ile Lys Lys Tyr
    515                 520                 525

Ala Glu Leu Leu Lys Ala Lys Thr Gly Leu Asp Ala Leu Lys Thr Ser
530                 535                 540

Asp Arg Val Ser Met Thr Phe Val Val Thr Ala Pro Lys Asp Thr Val
545                 550                 555                 560

His Ala Thr Ser Val Ile Lys Gly Pro Gly Asn Thr Asp Arg Val Met
            565                 570                 575

Ala Val Leu Asp Asn Asn Lys Trp Ser Gln
        580                 585

<210> SEQ ID NO 49
<211> LENGTH: 587
<212> TYPE: PRT

<213> ORGANISM: Aliivibrio wodanis

<400> SEQUENCE: 49

```
Met Ser Lys Gln Met Lys Phe Gly Leu Leu Pro Ala Ala Ile Ala Gly
1               5                   10                  15

Ala Leu Leu Ser Gly Asn Ala Phe Ala Gly Thr Glu Ala Cys Ile Glu
            20                  25                  30

Ile Ser Lys Thr Thr Ala Ser Tyr Thr Glu Leu Ala Ala Ala Asp Leu
        35                  40                  45

Tyr Glu Gly Ser Ala Cys Ser Tyr Thr Gly Thr Ser Thr Asp Lys Asp
50                  55                  60

Leu Leu Pro Asn Asn Ser Ala Lys Ile Ala Tyr Glu Leu Thr Lys Val
65                  70                  75                  80

Ala Asp Tyr Asp Leu Glu Asp Ile Thr Lys Thr Ala Tyr Thr Gly Lys
                85                  90                  95

Ala Ser Asp Asp Leu Ser Ile Val Tyr Val Pro Thr Thr Asp Val Pro
            100                 105                 110

Pro Ala Ala Arg Leu Thr Phe Lys Leu Asn Asn Ala Thr Phe Ala Val
        115                 120                 125

Asp Glu Asn Ile Ile His Leu Val Lys Val Glu Glu Asp Ser Gln Asn
130                 135                 140

Pro Gly Ser Tyr Ile Tyr Thr Ala Val Ala Ser Ser Asp Gly Gln Val
145                 150                 155                 160

Asp Gly Glu Ser Thr Ala Leu Phe Met Val Lys Ser Gly Val Thr Val
                165                 170                 175

Gly Ala Gly Thr Arg Leu Phe Leu Ser Thr Ser Asn Gln Pro Thr Ala
            180                 185                 190

Leu Thr Gly Ile Thr Thr Pro Gly Ile His Leu Glu Phe Thr Glu Glu
        195                 200                 205

Cys Thr Val Asp Gln Lys Val Thr Leu Glu Val Ile Asp Ala Lys Thr
210                 215                 220

Asp Phe Gly Phe Val Ile Ala Gly Ala Lys Thr Gln Ala Ala Ser Asp
225                 230                 235                 240

Leu Val Val Ala Glu Arg Gln Tyr Gln Leu Ala Val Glu Lys Asn Leu
                245                 250                 255

Pro Val Gly Gln Leu Thr Leu Thr Val Glu Ala Asp Val Asn Ala Glu
            260                 265                 270

Asp Pro Ser Gln Arg Lys Phe Phe Leu Thr Asn Thr Gly Ala Gly Glu
        275                 280                 285

Leu Ala Pro Pro Ala Gly Gly Trp Asp Asn Gln Thr Thr Ala Lys Ser
290                 295                 300

Val Val Trp Glu Ala Tyr Phe Gln Asn Asn Phe Asn Ser Leu Asp Leu
305                 310                 315                 320

Ala His Val Leu Arg Pro Glu Asp Lys Val Leu Leu Asp Thr Asn Ser
                325                 330                 335

Pro Lys Tyr Thr Gly Thr Ala Ile Thr Leu Gly Ala Leu Thr Gln Met
            340                 345                 350

Thr Asn Ala Thr Thr Ala Leu Asp Lys Met Thr Asn Ser His Leu Ala
        355                 360                 365

Ala Asn Thr Asn His Val Asp Phe Asn Glu Thr Thr Glu Trp Ala Thr
370                 375                 380

Leu Asn Ser Ser Leu Thr Ser Tyr His Phe Asp Ala Glu Glu Val Phe
385                 390                 395                 400
```

```
Gly Pro Thr Asp Leu Thr Gly Ala Asp Thr Asp Arg Ala Leu Ala Leu
                405                 410                 415

Val Leu Ala Thr Asn Gly Thr Thr Pro Met Asn Phe Gly Tyr Ser Val
            420                 425                 430

Asp Ala Lys Phe Gly Met Asp Leu Ala Asp Val Thr Gly Gly Leu Phe
        435                 440                 445

Thr Tyr His Asp Thr Ala Thr Ser Cys Asn Pro Thr Thr Pro Phe Ala
    450                 455                 460

Ile Asp Val Asn Gly Ala Val Leu Lys Val Pro Tyr Ala Tyr Asn Thr
465                 470                 475                 480

Asp Lys Asn Trp Val Arg Ile Thr Asn Glu His Asp Thr Glu Ala Glu
                485                 490                 495

Val Thr Val Glu Val Phe Asp Glu Asn Asp Ala Ala Gly Asp Lys Arg
            500                 505                 510

Ile Leu Thr Leu Ala Lys Ile Gly Ala Asp Ser Thr Val Tyr Lys
        515                 520                 525

Ala Asp Ala Ile Ile Ala Leu Tyr Glu Ala Glu Ile Gly Arg Ala Ser
    530                 535                 540

Ser Asn Arg Val Ser Met Thr Phe Thr Val Thr Ala Pro Lys Asp Thr
545                 550                 555                 560

Val His Gly Val Ser Val Gln Ala Ile Pro Gly Gly Val Asp Arg Val
                565                 570                 575

Leu Pro Val Leu Asp Gln Asn Asn Trp Asn Gln
                580                 585

<210> SEQ ID NO 50
<211> LENGTH: 7
<212> TYPE: PRT
<213> ORGANISM: Artificial Sequence
<220> FEATURE:
<223> OTHER INFORMATION: motif

<400> SEQUENCE: 50

Gly Thr Glu Ala Cys Ile Glu
1               5

<210> SEQ ID NO 51
<211> LENGTH: 5
<212> TYPE: PRT
<213> ORGANISM: Artificial Sequence
<220> FEATURE:
<223> OTHER INFORMATION: portion of fusion moiety

<400> SEQUENCE: 51

Gly Asn Ala Phe Ala
1               5

<210> SEQ ID NO 52
<211> LENGTH: 60
<212> TYPE: RNA
<213> ORGANISM: Artificial Sequence
<220> FEATURE:
<223> OTHER INFORMATION: RNA sequence depicted in Figure 6B

<400> SEQUENCE: 52
augaguaagc aaaugaaguu uggacuucuu ccagcagcga ucgcuggugc auuacugagc    60
```

FUSION MOIETIES AND MICROBIAL HOSTS FOR PROTEIN PRODUCTION

The present invention relates generally to microbial host cells for protein production. In particular, the present invention relates to a particular species of sub-Arctic bacterium as a host cell for protein production. The invention also provides polypeptide and polynucleotide sequences that enhance the expression of a protein of interest in host cells.

The first recombinant proteins were expressed in *Escherichia coli* in 1976, and since then the production of recombinant proteins in *E. coli* has had a great impact on our lives, e.g., by eliminating the need to extract proteins from large volumes of biological materials. However, even though the production of recombinant proteins is a well-developed method, there are still challenges to overcome and many variables to consider, e.g., the expression host, plasmids, promoters, selection markers, affinity tags, and fusion partners.

Some proteins, for example psychrophilic (cold-adapted) enzymes, are difficult to express in conventional hosts (such as *E. coli*), for example as they may aggregate in inclusion bodies in standard hosts. Psychrophilic enzymes originate from organisms living in cold environments, and with 80% of the earth's biosphere being cold (e.g., below 5° C.), organisms living in these environments represent a largely untapped resource with respect to enzyme development.

Cold adapted enzymes are generally characterized by having a higher catalytic activity at low temperatures, compared to their mesophilic homologues (e.g. up to 10× higher). Current understanding of this phenomenon is that the whole protein, or parts of it (e.g. the active site), is destabilized thus allowing flexibility at low temperatures. Consequently, cold-adapted enzymes typically melt at relatively low temperatures. In other words, they are typically thermolabile, and a gentle rise in temperature can therefore inactivate the protein. These properties can be highly beneficial in some commercial and biotechnological applications. One example of activity at low temperatures being beneficial is the use of cold-active enzymes as components in detergents, thus reducing the need to heat water during washing. Another example is the shrimp alkaline phosphatase that is completely inactivated after 5 min at 65° C. In comparison, a typical protocol for >95% inactivation of calf intestinal alkaline phosphatase is 10 min at 70° C. More gentle heat inactivation can improve the quality of the final sample and simplify experimental protocols. Cold-active enzymes are therefore replacing some of the mesophilic enzymes already on the market. Progress in development of new cold-active enzymes is however slow, and severely hampered by the lack of efficient protocols for expression of cold-active proteins in active form.

There is therefore an urgent need to develop new tools, methods and expression hosts suitable for low-temperature expression of proteins (e.g. cold-active or cold adapted proteins or other proteins that are difficult to express in mesophiles).

In this regard, the present inventors have found that the bacterium *Aliivibrio wodanis* is a useful expression host for proteins that are typically difficult to express in mesophiles such as *E. coli* (e.g. cold-adapted enzymes). The inventors have demonstrated that proteins, particularly cold-adapted proteins, can be expressed in *Aliivibrio wodanis*, and that such proteins can be readily produced and purified, and importantly remain active. The inventors have found that *Aliivibrio wodanis* can be easily and cost-effectively cultured and that *Aliivibrio wodanis* grows fast at low temperatures. The inventors have also shown proteins expressed in *Aliivibrio wodanis* host cells appear in the soluble fraction and thus are readily accessible and amenable to purification and downstream uses. This is unlike some other expression systems (e.g. *E. coli*) in which expressed proteins can form inclusion bodies. The inventors have also developed molecular tools that can further enhance the utility of *Aliivibrio wodanis* as a protein expression host.

Thus, in a first aspect, the present invention provides a method of producing a protein, said method comprising culturing an *Aliivibrio wodanis* host cell comprising a heterologous nucleic acid molecule encoding said protein under conditions suitable for the expression of the encoded protein.

Thus, methods of the present invention employ *Aliivibrio wodanis* as a protein expression host.

In some embodiments, the *Aliivibrio wodanis* (*Aliivibrio wodanis* strains) are characterised by having an optimal growth rate at a temperature of 5.20° C. In some embodiments, the *Aliivibrio wodanis* (*Aliivibrio wodanis* strains) are characterised by having their optimal growth rate at a temperature of about 12° C.-18° C. (e.g. about 12° C., 13° C., 14° C., 15° C., 16° C., 17° C. or 18° C.). However, *Aliivibrio wodanis* may be grown (cultured) at lower temperatures, for example at temperatures approaching freezing (e.g. at about 4° C.). Growth rate, which may be evaluated in terms of "doubling time", may be assessed in any suitable culture media, e.g. Lysogeny Broth (LB) supplemented with 2.5% NaCl. Without wishing to be bound by theory, it is believed that the ability to grow at low temperatures, and in particular to have an optimum growth rate at low temperatures (e.g. 12° C.-18° C.), may be particularly advantageous when it comes to expressing pyschrophilic enzymes. The inventors have an in-house collection of ~1000 cold-adapted marine bacteria and have observed that bacteria having comparable growth characteristics to *Aliivibrio wodanis* are rare.

Preferably, the *Aliivibrio wodanis* (*Aliivibrio wodanis* strains) used in methods of the present invention can be grown to high density, at low temperatures. In some embodiments, the *Aliivibrio wodanis* is characterised by having a doubling time of about 150 minutes (e.g. 120-180 minutes or 140-160 minutes) when grown at about 12° C. (e.g. 10° C.-14° C.). In some embodiments, the *Aliivibrio wodanis* is characterised by having a doubling time of about 25 hours (e.g. 20-30 hours or 23-27 hours) when grown at about 4° C. (e.g. 2° C.-6° C.). Preferably, such doubling times are as assessed in culture in Lysogeny Broth (LB) supplemented with 2.5% NaCl.

In some embodiments, the *Aliivibrio wodanis* is characterised by its ability to reach its maximum optical density (OD, e.g. as assessed at 600 nm, $OD_{600\,nm}$) at about 1-3 days (e.g. 2-3 days or 2.5-3.5 days e.g. about 3 days) of growth in liquid culture at about 12° C. (e.g. 10° C.-14° C., preferably at 12° C.), preferably in Lysogeny Broth (LB) supplemented with 2.5% NaCl. In some embodiments, the *Aliivibrio wodanis* is characterised by its ability to reach its maximum optical density (OD, e.g. as assessed at 600 nm, $OD_{600\,nm}$) at about 4-7 days (e.g. 5 to 7 days or 5 to 6 days e.g. about 6 days) of growth in liquid culture at about 4° C. (e.g. 2° C.-4° C., preferably at 4° C.), preferably in Lysogeny Broth (LB) supplemented with 2.5% NaCl.

In some embodiments, the *Aliivibrio wodanis* is characterised by an ability to reach an $OD_{600\,nm}$ of about 7 (e.g. 6-8) when grown in liquid culture (preferably in Lysogeny Broth (LB) supplemented with 2.5% NaCl) at about 12° C. (e.g. 10° C.-14° C., preferably at 12° C.), for example for about 3 days.

In some embodiments, the *Aliivibrio wodanis* is characterised by an ability to reach an $OD_{600\ nm}$ of about 2.5 to 3 when grown in liquid culture (preferably in Lysogeny Broth (LB) supplemented with 2.5% NaCl) at about 4° C. (e.g. 2° C.-6° C., preferably at 4° C.), for example for about 6 to 10 days.

In preferred embodiments, the *Aliivibrio wodanis* host cell is sensitive to (or susceptible to, or exhibits no growth or no significant growth when exposed to) one or more antibiotics. Such antibiotic sensitivity means that an antibiotic may be used a selection agent to select for *Aliivibrio wodanis* cells that have been transformed or conjugated with (or have taken up) a polynucleotide encoding an antibiotic resistance gene. For example, in connection with the present invention, the heterologous nucleic acid molecule encoding said protein may be an expression vector (e.g. a plasmid) encoding the protein (protein to be produced) and additionally an antibiotic resistance protein, and the sensitivity of the *Aliivibrio wodanis* host cell (i.e. the recipient *Aliivibrio wodanis* host cell prior to transformation or conjugation) to an antibiotic means that the antibiotic may be used as a selection agent (i.e. to exert a selection pressure) to select for those *Aliivibrio wodanis* cells (or colonies) that have been transformed or conjugated with the polynucleotide.

In some embodiments, the antibiotic is chloramphenicol (also referred to herein as Cm or CHL) or tetracycline. In some embodiments, the *Aliivibrio wodanis* host cell is susceptible to 2 µg/ml chloramphenicol or 4 µg/ml chloramphenicol. In some embodiments, the *Aliivibrio wodanis* host cell is susceptible to 10 µg/ml tetracycline or 20 µg/ml tetracycline. In some embodiments, the susceptibility to antibiotics is as assessed in culture on agar plates (e.g. LB agar plates supplemented with 2.5% NaCl) at 12° C. for 2 days.

For the avoidance of doubt, reference to the *Aliivibrio wodanis* host cell being sensitive to one or more antibiotics is a reference to antibiotic sensitivity of the *Aliivibrio wodanis* host cell in the absence of the heterologous polynucleotide (e.g. prior to transformation or conjugation with such a polynucleotide).

*Aliivibrio wodanis* host cells in connection with the present invention are capable of taking up (or receiving) and expressing a heterologous nucleic acid molecule (e.g. a plasmid) encoding a protein (the protein to be produced). There are a variety of methods for introducing a heterologous nucleic acid molecule encoding a protein into bacterial cells and any of these may be used in connection with the present invention. Such methods include transformation (e.g. by heat-shock or electroporation) and conjugation (plasmid conjugation)). Thus, preferably *Aliivibrio wodanis* host cells are capable of having a heterologous nucleic acid molecule encoding a protein introduced by transformation or conjugation. Conjugation is particularly preferred. Thus, in some embodiments, *Aliivibrio wodanis* host cells are capable of having a heterologous nucleic acid molecule encoding a protein introduced by conjugation, preferably by a triparental mating method (e.g. as described elsewhere herein).

A tri-parental mating method is a bacterial conjugation method of introducing a nucleic acid molecule into a recipient bacterial host. Tri-parental mating methods are well established in the art and are typically characterised by a conjugative plasmid present in one bacterial strain (which may be referred to as a "helper" strain) that assists (or facilitates) the transfer of donor plasmid present in another bacterial strain (which may be referred to as a "donor" strain) into a third bacterial strain (which may referred to as a "recipient strain"). When a triparental mating method is used in the context of the present invention the "donor" plasmid comprises a heterologous nucleic acid molecule encoding a protein (protein to be produced). In the context of the present invention the "recipient" strain is an *Aliivibrio wodanis* strain. An exemplary and preferred "helper" strain is *E. coli* CC118 λpir (carrying a conjugative/helper plasmid such as pEVS104, e.g. as described by Stabb and Ruby (2002)). An exemplary and preferred "donor" strain is *E. coli* CC118 λpir carrying a donor plasmid such as pTM214 e.g. as described in Miyashiro et al. (2011)). These strains are described in the Example section herein.

Methods of introducing heterologous nucleic acids encoding proteins by conjugation (e.g. by a triparental mating method) into bacterial cells are known in the art and any suitable method may be used.

One example of a tri-parental mating method is as follows: An *E. coli* helper strain (e.g. *E. coli* CC118 λpir carrying a helper/conjugative plasmid such as pEVS104, Stabb and Ruby (2002)) and an *E. coli* donor strain (e.g. *E. coli* CC118 λpir carrying a donor plasmid such as pTM214, Miyashiro et al. (2011)) are grown, e.g. at about 37° C., for example to an $OD_{600}$ of 0.5-0.7 (e.g. in Lysogeny Broth) in presence of antibiotics that exert selection pressure on the helper and donor strains (e.g. 50 µg/ml kanamycin for a helper strain carrying the pEVS104 plasmid and 20 µg/ml chloramphenicol for a donor strain carrying the pTM214 plasmid). An *Aliivibrio wodanis* strain (recipient strain) is grown, e.g. at about 12° C., for example to an $OD_{600}$ of 1-2 (e.g. in Lysogeny Broth, LB, supplemented with 2.5% NaCl). An aliquot of each bacterial culture (e.g. a 1 ml aliquot) is pelleted (typically by centrifugation) and resuspended in medium (e.g. resuspended in LB, e.g. 1 ml). The resuspended bacteria may be pelleted and resuspended in medium (e.g. LB, e.g. 1 ml) for a second time. An aliquot (e.g. 500 µl) of each of the resuspended bacterial strains (an aliquot of each of the donor, helper and recipient strains) are mixed and then pelleted by centrifugation. The supernatant is removed and the pellet is resuspended in a small volume (e.g. about 20 µl) of medium (e.g. LB). The resuspended bacteria (bacterial mixture) is then plated (e.g. spotted) on an agar plate (e.g. an LB agar plate supplemented with 1% NaCl) and incubated at e.g. 16° C. The incubation time may be about 24 hours (e.g. for plasmid pTM214) or about 48 hours (e.g. for plasmid pNQ705). After incubation the bacteria (typically after having been scraped off the agar plate) are resuspended in medium (e.g. LB supplemented with 2.5% NaCl), plated (e.g. spread) on agar plates (e.g. LB agar) and cultured under conditions which support the growth of *Aliivibrio wodanis* colonies carrying the plasmid (donor plasmid) but which do not support the growth of *E. coli*. Such conditions may be growth for 3 days at 12° C. on LB agar supplemented with 2.5% NaCl and an agent such as an antibiotic to select for the presence of the donor plasmid (e.g. 2 µg/ml chloramphenicol for plasmid pTM214). Colonies that grow under these conditions are *Aliivibrio wodanis* colonies comprising (i.e. harbouring) the donor plasmid which comprises a heterologous nucleic acid molecule encoding a protein (the protein to be produced).

The triparental mating method (triparental mating approach) described in the Example section herein is particularly preferred.

In some embodiments of methods of the invention, the method comprises a step, prior to culturing the *Aliivibrio*

*wodanis*, of introducing a heterologous nucleic acid molecule encoding a protein (the protein to be produced) into the *Aliivibrio wodanis* host cell. This "introducing" step may be done by any appropriate means, for example by transformation (e.g. by heat-shock" or electroporation) or by conjugation (plasmid conjugation). In a preferred embodiment, the method comprises a step of introducing a heterologous nucleic acid molecule encoding a protein into the *Aliivibrio wodanis* host cell by conjugation, particularly preferably by a triparental mating method (e.g. as described elsewhere herein).

*Aliivibrio wodanis* host cells in connection with the present invention are capable of expressing a heterologous nucleic acid molecule encoding a reporter protein, for example a fluorescent protein such as GFP (green fluorescent protein), RFP (red fluorescent protein) or mCherry.

In some embodiments, *Aliivibrio wodanis* host cells in connection with the present invention are capable of expressing a reporter protein (e.g. a fluorescent protein) that is expressed from (i.e. encoded by) an expression vector, typically a plasmid (e.g. pTM214 or pVSV208). In some embodiments, the *Aliivibrio wodanis* is capable of expressing a reporter protein (e.g. a fluorescent protein) that has been introduced (e.g. on a plasmid) by a tri-parental mating method (e.g. as described elsewhere herein). The expression of a fluorescent reporter protein may be assessed via fluorescent microscopy and/or by analysing or measuring fluorescence in the supernatant of lysed cell cultures (e.g. at 588 nm in the case of RFP or at 485-538 nm in the case of GFP). Alternatively, or additionally, the expression of a reporter protein may be assessed by affinity purifying the reporter protein (e.g. based on the presence of an affinity tag such as a His-tag, if present), subjecting the affinity purified material to SDS-PAGE electrophoresis and assessing (and optionally quantifying) the level of expression of the reporter protein, e.g. by assessing the intensity of the band corresponding to reporter protein on a stained (e.g. coomassie stained) SDS-PAGE gel and optionally identifying the protein in the band as the reporter protein via mass spectrometry. In some embodiments, the reporter protein expression is as assessed in *Aliivibrio wodanis* strains grown at about 12° C.

Methods for expressing, and assessing the expression of, reporter proteins (e.g. fluorescent proteins) are described in the Example section herein and these represent preferred methods.

*Aliivibrio wodanis* host cells in connection with the present invention are capable of expressing a heterologous nucleic acid molecule encoding an active enzyme. Any appropriate method may be used for assessing the ability to express an active enzyme and a skilled person is familiar with such methods.

In some embodiments, *Aliivibrio wodanis* host cells in connection with the present invention are capable of expressing a heterologous nucleic acid molecule encoding the heterologous enzymes Exonuclease I or DNA Polymerase II from *Aliivibrio salmonicida*. The enzyme (e.g. Exonuclease I or DNA Polymerase II from *Aliivibrio salmonicida* or His-tagged versions of these proteins) may have been introduced into an *Aliivibrio wodanis* strain (e.g. on plasmid pTM214) using a triparental mating method (as described elsewhere herein), and grown (cultured) under conditions suitable for the expression of the encoded protein (e.g. using Lysogeny Broth, LB, supplemented with 2.5% NaCl, and optionally an antibiotic and optionally IPTG (e.g. for IPTG inducible promoters), for example for 3 days at 12° C.). Expression (e.g. the level of expression) of the enzyme may be assessed by any appropriate means, for example by analysing the soluble proteins (in the soluble fraction after cell lysis) by SDS-PAGE electrophoresis, for example subsequent to affinity purification of the enzyme (e.g. based on the presence of an affinity tag such as a His-tag, if present). The level of expression of the enzyme may be determined qualitatively or quantitatively and the skilled person is familiar with methods of doing this (e.g. by visually inspecting the intensity of the band on a stained SDS-PAGE gel that corresponds to the affinity purified protein, western blotting, or ELISA). Whether or not the expressed enzyme has retained its enzymatic activity may be assessed by any appropriate method and the choice of method will depend upon the type of enzyme expressed. Purely by way of example, Exonuclease I activity may be assessed by any Exonuclease I assay, for example a molecular beacon assay such as the molecular beacon assay described in the Example section herein. By way of another example, DNA Polymerase II activity may be assessed by any DNA polymerase assay, for example a molecular beacon assay such as the molecular beacon assay described in the Example section herein. For the avoidance of doubt, the term "active enzyme" means an enzyme that retains enzymatic activity after expression in, and isolation, purification (e.g. affinity purification) or harvesting from, the *Aliivibrio wodanis* strain (or the culture medium).

In a preferred embodiment, the *Aliivibrio wodanis* is an *Aliivibrio wodanis* strain selected from the group consisting of:
  (i) the *Aliivibrio wodanis* strain deposited under accession number ECACC 18050101. This strain is also referred to herein as 01/09/401 (and 01/09/401 (11) or Vw11);
  (ii) the *Aliivibrio wodanis* strain deposited under accession number ECACC 18050102. This strain is also referred to herein as 03/09/160 (and 03/09/160 (37) or Vw37); and
  (iii) an *Aliivibrio wodanis* strain having all the identifying characteristics of one or both of strains (i) and (ii).

The ECACC is the European Collection of Authenticated Cell Cultures having its address at Public Health England, Culture Collections, Porton Down, Salisbury, Wiltshire SP4 0JG, United Kingdom. Each deposit was made with the ECACC under the Budapest Treaty on 1 May 2018 and confirmed as viable. The stated depositor of the deposited strains is "UiT The Arctic University of Norway". For the avoidance of doubt, this is simply the English language version of the name of the Applicant, "Universitetet i Tromsø-Norges Arktiske Universitet". The stated depositor of the strains is the same entity as the Applicant.

In a particularly preferred embodiment, the *Aliivibrio wodanis* is an *Aliivibrio wodanis* strain selected from the group consisting of:
  (i) the *Aliivibrio wodanis* strain deposited under accession number ECACC 18050101. This strain is also referred to herein as 01/09/401 (and 01/09/401 (11) or Vw11); and
  (ii) the *Aliivibrio wodanis* strain deposited under accession number ECACC 18050102. This strain is also referred to herein as 03/09/160 (and 03/09/160 (37) or Vw37).

"*Aliivibrio wodanis* strains having all the identifying characteristics" of the deposited strains will include descendants and mutants of said strains. It is recognised that minor genotypic changes in such descendants and mutants may not be reflected in phenotypic changes and that some minor phenotypic changes in such descendants and mutants will be irrelevant, in particular irrelevant in terms of the protein production ability (i.e. ability to be used as host cell for protein expression), and consequently such descendants and mutants would, in the context of the present invention, be functionally equivalent to the deposited strains. "Identifying characteristics" will be understood with this purpose in mind.

"Aliivibrio wodanis strains having all the identifying characteristics" of the deposited strains typically have all of the following characteristics (or properties):

(a) a growth rate that is substantially equivalent to, equivalent to, or at least as fast as, the growth rate of one or both of the deposited strains (e.g. at a temperature in the range of 4-18° C., e.g. 4-12° C. or 12-18° C., such as at 4° C. or at 12° C.);

(b) a conjugation efficiency (plasmid conjugation efficiency) that is substantially equivalent to, equivalent to, or at least as efficient as, the conjugation efficiency of one or both of the deposited strains (e.g. as assessed in a triparental mating method e.g. as described elsewhere herein). The plasmid (donor plasmid) used for the assessment of conjugation efficiency may in some embodiments be pTM214 or pNQ705;

(c) an ability to express a reporter protein (e.g. GFP, RFP or mCherry), preferably under antibiotic selection pressure, that is substantially equivalent to (at a substantially equivalent level to), equivalent to (at an equivalent level to), or at least as high as (as least as high a level as), the ability of one or both of the deposited strains to express a reporter protein. The ability to express a reporter protein may be the ability to express RFP (e.g. typically expressed from a plasmid) under antibiotic selection pressure (such as 2 µg/ml chloramphenicol), that is substantially equivalent to, equivalent to, or at least as high as, the ability of one or both of the deposited strains to express RFP under the same conditions; and (d) an ability to express an active enzyme (a heterologous enzyme, e.g. Exonuclease I or DNA Polymerase II from *Aliivibrio salmonicida*), preferably under antibiotic selection pressure, that is substantially equivalent to (at a substantially equivalent level to), equivalent to (at an equivalent level to), or at least as high as (as least as high a level as), the ability of one or both of the deposited strains to express said active enzyme under the same conditions.

In relation to characteristic (a) above, the growth rate may be assessed by any appropriate method and a skilled person is familiar with such methods. For example, the growth rate may be assessed in a suitable growth medium (culture medium, preferably liquid medium), e.g. LB, Lysogeny Broth, supplemented with 2.5% NaCl. Growth rate may be as assessed, for example, at a temperature in the range of about 4° C. to about 12° C. (e.g. at 4° C. or 12° C.) over any suitable period of time, for example 1-14 days (e.g. 2-11 days, or 5-11 days or 2-7 or 5-7 days). For example, growth rate may as assessed at 4° C. over 6 days or at 12° C. over 3 days. The growth rate may be characterised by a doubling time of about 150 minutes when grown at 12° C. (e.g. in LB supplemented with 2.5% NaCl) or about 25 hours when grown at 4° C. (e.g. in LB supplemented with 2.5% NaCl).

In relation to characteristic (b) above, conjugation efficiency (plasmid conjugation efficiency) may be assessed by any appropriate method and a skilled person is familiar with such methods. Conjugation efficiency can be considered as the capacity of the *Aliivibrio wodanis* strain to receive (or take up) a conjugative plasmid. Conjugation efficiency may be assessed, for example, by using a triparental mating method, which employs a helper bacterial strain (e.g. *E. coli* CC118 λpir carrying a conjugative plasmid such as pEVS104), a donor bacterial strain carrying the plasmid to be transferred into the recipient strain (e.g. *E. coli* CC118 λpir carrying a donor plasmid such as pTM214), and a recipient strain (the *A. wodanis* recipient strain/target cell). After conjugation (and antibiotic selection in cases where the donor plasmid encodes an antibiotic resistance gene) the number of *Aliivibrio wodanis* colonies that have received the donor plasmid can be readily assessed by counting the number of colonies present (e.g. on culture plates such as agar plates e.g. LB agar plates supplemented with 2.5% NaCl), for example after about 3 days culture at 12° C. The conjugation efficiency may also be expressed in terms of colony-forming units (cfu). Thus, in relation to characteristic (b) above, an *Aliivibrio wodanis* strain post-conjugation typically produces (or gives rise to) a number of colonies (or colony-forming units) that is substantially equivalent to, equivalent to, or higher than the number of colonies (or colony-forming units) obtained (or observed) for one or both of the deposited strains post-conjugation. If the donor plasmid carries a reporter gene (e.g. a fluorescent reporter gene), conjugation efficiency may be assessed by observing the expression of (or measuring the expression of) the reporter gene post-conjugation. Thus, in relation to characteristic (b) above, an *Aliivibrio wodanis* strain post-conjugation may exhibit substantially equivalent, equivalent, or expression of the reporter gene than as compared to the expression of the reporter gene by one or both of the deposited strains post-conjugation. A particularly preferred method for assessing conjugation efficiency is described in the Example section herein.

In relation to characteristic (c) above, the reporter protein may be a fluorescent protein, e.g. GFP, RFP or mCherry. Any appropriate method for assessing reporter protein may be used and a skilled person is familiar with such methods. In one embodiment, RFP may be introduced into an *Aliivibrio wodanis* strain, e.g. on plasmid pVSV208 (Dunn et al., (2006)), using a triparental mating method, and the expression of RFP may be assessed, under antibiotic selection (e.g. chloramphenicol), by (i) observing RFP expression in *Aliivibrio wodanis* colonies (grown on culture plates) by fluorescent microscopy and/or (ii) monitoring RFP expression in the supernatant of lysed cell cultures by measuring fluorescence (e.g. at 588 nm). In such methods, *Aliivibrio wodanis* strains are typically grown at 12° C. (e.g. for about 3 days). Such a method for assessing RFP reporter expression is described in the Example section herein and represents a preferred method. In another embodiment, GFP (e.g. His-tagged GFP) may be introduced into an *Aliivibrio wodanis* strain (e.g. on plasmid pPSY001) using a triparental mating method, and the expression of GFP may be assessed, under antibiotic selection (e.g. chloramphenicol), by (i) observing GFP expression in *Aliivibrio wodanis* colonies (grown on culture plates) by fluorescent microscopy and/or (ii) monitoring GFP expression in the supernatant of lysed cell cultures by measuring fluorescence (e.g. at 485-538 nm) and/or (iii) affinity purifying the GFP (e.g. based on the presence of a His-tag if present), subjecting the affinity purified material to SDS-PAGE electrophoresis and assessing (and optionally quantifying) the level of expression of GFP, e.g. by assessing the intensity of the band corresponding to GFP on a stained (e.g. coomassie stained) SDS-PAGE gel and optionally identifying the protein in the band as GFP via mass spectrometry. Methods for assessing GFP expression are described in the Example section herein and represent preferred methods. In methods for assessing reporter gene expression, *Aliivibrio wodanis* strains are typically grown at 4° C.-18° C., preferably 4° C.-12° C. (e.g. at 4° C. or at 12° C.). Thus, in relation to characteristic (c) above, an *Aliivibrio wodanis* strain post-conjugation typically expresses a reporter protein (e.g. RFP or GFP or mCherry) to a level (or degree) that is substantially equivalent to, equivalent to, or higher than, the level (or degree) of reporter protein expression in one or both of the deposited strains post-conjugation.

In relation to characteristic (d) above, the active enzyme may be a polymerase or a nuclease, e.g. the heterologous enzymes Exonuclease I or DNA Polymerase II from *Aliivibrio salmonicida*. Any appropriate method may be used for assessing the ability to express an active enzyme and a skilled person is familiar with such methods. In such methods, the enzyme (e.g. Exonuclease I or DNA Polymerase II from *Aliivibrio salmonicida* or His-tagged versions of these proteins) may be introduced into an *Aliivibrio wodanis* strain (e.g. on plasmid pTM214) using a triparental mating method, and grown (cultured) under appropriate conditions (e.g. using LB supplemented with 2.5% NaCl, 2 μg/ml chloramphenicol, 100 mM IPTG for e.g. 3 days at 12° C.). Expression (e.g. the level of expression) of the enzyme may be assessed by any appropriate means for example by analysing the soluble proteins (in the soluble fraction after cell lysis) by SDS-PAGE electrophoresis, for example subsequent to affinity purification of the enzyme (e.g. based on the presence of a His-tag if present). The level of expression of the enzyme may be determined qualitatively or quantitatively and the skilled person is familiar with methods of doing this (e.g. by visually inspecting the intensity of the band on a stained SDS-PAGE gel, western blotting, or ELISA). Whether or not the expressed enzyme has enzymatic activity may be assessed by any appropriate method and the choice of method will depend upon the type of enzyme expressed. Purely by way of example, Exonuclease I activity may be assessed by any Exonuclease I assay, for example a molecular beacon assay such as the molecular beacon assay described in the Example section herein. By way of another example, DNA Polymerase II activity may be assessed by any DNA polymerase assay, for example a molecular beacon assay such as the molecular beacon assay described in the Example section herein. Thus, in relation to characteristic (d) above, an *Aliivibrio wodanis* strain post-conjugation typically expresses an active enzyme to a level (or degree) that is substantially equivalent to, equivalent to, or higher than, the level (or degree) of expression of said active enzyme by one or both of the deposited strains post-conjugation.

"Substantially equivalent to" typically means at least 80% of, preferably at least 90%, more preferably at least 95% of the performance of one or both of the deposited strains in relation to that characteristic.

In some embodiments, "*Aliivibrio wodanis* strains having all the identifying characteristics" of the deposited strains preferably have an ability to uniformly (or substantially uniformly) express a reporter protein (e.g. RFP) in all (or substantially all) colonies (or cells) of a culture (e.g. as assessed by fluorescent microscopy). Thus, in such embodiments there is uniformity or homogeneity (or substantial uniformity or substantial homogeneity) in the level of expression of the reporter protein between different (i.e. separate) colonies of the bacterial culture (e.g. different colonies on the same culture plate).

"*Aliivibrio wodanis* strains having all the identifying characteristics" of the deposited strains may also be considered to be a reference to *Aliivibrio wodanis* strains that are functionally equivalent to the deposited strains for the purpose of producing a protein in accordance with methods of the present invention.

Any type of protein may be produced using methods of the present invention.

In a preferred embodiment, the protein produced by methods of the invention is an enzyme. Particularly preferred enzymes are enzymes useful in molecular biology applications and/or in industrial applications. Exemplary industrial applications include applications in the laundry, food, feed and biomass conversion industries.

Thus, for example, nucleases (e.g. deoxyribonucleases or ribonucleases), polymerases (e.g. DNA polymerases or RNA polymerases), proteases, ligases, reverse transcriptases, phosphatases (e.g. alkaline phosphatase), kinases, methylases, topoisomerases, lipases, carbohydrases, amylases and cellulases are enzymes that may be produced using methods of the present invention. Other types of enzyme may also be produced, e.g. dehydrogenases such as alcohol dehydrogenases.

In some embodiments, the enzyme produced by methods of the invention is a nuclease (e.g. an exonuclease such as an Exonuclease I), a polymerase (e.g. a DNA polymerase such as DNA polymerase II), a ligase (such as a ligase 1 or a ligase 6), or an alcohol dehydrogenase. In some embodiments, the enzyme produced by methods of the invention is a nuclease (e.g. an exonuclease such as an Exonuclease I) or a polymerase (e.g. a DNA polymerase such as DNA polymerase II).

When producing proteins (e.g. enzymes) it is generally important that they are active (i.e. maintain enzyme activity in the case of enzymes) once they have been isolated, purified or harvested from the host cells in which they were produced. The present inventors have shown that enzymes can be produced in *Aliivibrio wodanis* in accordance with the present invention and that the isolated (or purified) enzymes produced are enzymatically active. The skilled person will be familiar with techniques to assess or verify that enzyme activity is present; the technique will of course depend on the type of enzyme. For example, Exonuclease I activity may be assessed by any Exonuclease I assay, for example a molecular beacon assay such as the molecular beacon assay described in the Example section herein. By way of another example, DNA Polymerase II activity may be assessed by any DNA polymerase assay, for example a molecular beacon assay such as the molecular beacon assay described in the Example section herein.

In preferred embodiments, the protein (e.g. enzyme) is a "cold-apdated" or "cold-active" protein. This means that the protein exhibits activity, preferably significant activity, or even its maximum activity, at cold temperatures, as discussed below.

In some embodiments, the protein to be produced (e.g. enzyme) is from (i.e. is derived from, or originates from, or is a protein encoded by) an organism that has a cold-temperature habitat (is found in a cold environment), e.g. a sub-Arctic or Arctic habitat. In some embodiments, the protein (e.g. enzyme) is from an organism that has a habitat having an average temperature of $\leq 10°$ C., $\leq 9°$ C., $\leq 8°$ C., $\leq 7°$ C., $\leq 6°$ C., or preferably $\leq 5°$ C. (e.g. $-20°$ C. to $10°$ C., or $-20°$ C. to $5°$ C., or $0°$ C. to $10°$ C., or $0°$ C. to $5°$ C., e.g. about $0°$ C., about $1°$ C., about $2°$ C., about $3°$ C., about $4°$ C. or about $5°$ C.).

In some embodiments, the protein to be produced (e.g. enzyme) is from an organism that can survive, and preferably grow (e.g. grow optimally), at a temperature of $<15°$ C., preferably $\leq 10°$ C., $\leq 9°$ C., $\leq 8°$ C., $\leq 7°$ C., $\leq 6°$ C., or preferably ≤5° C. (e.g. −20° C. to 10° C., or −20° C. to 5° C., or 0° C. to 10° C., or 0° C. to 5° C., e.g. about 0° C., about 1° C., about 2° C., about 3° C., about 4° C. or about 5° C.).

In preferred embodiments, the protein to be produced (e.g. enzyme) is from (i.e. is derived from, or originates from, or is encoded by) a marine organism, preferably a marine microorganism, more preferably a marine bacterium. Preferably, the marine environment is a "cold" marine environment, e.g. having an average temperature of ≤10° C., ≤9° C., ≤8° C., ≤7° C., ≤6° C., or preferably ≤5° C. (e.g. −20° C. to 10° C., or −20° C. to 5° C., or 0° C. to 10° C., or 0° C. to 5° C., e.g. about 0° C., about 1° C., about 2° C., about 3° C., about 4° C. or about 5° C.).

Thus, in some embodiments, the protein (e.g. enzyme) is from (is derived from, or originates from, or is a protein encoded by) a psychrophilic organism (or psychrophile), preferably a psychrophilic micro-organism such as psychrophilic bacterium. Proteins (e.g. enzymes) from marine psychrophilic organisms (e.g. bacteria) are preferred in some embodiments. Psychrophilic organisms may also be referred to as cryophilic microorganisms. Psychrophilic organisms are typically capable of growth and reproduction at cold temperatures (e.g. in the range −20° C. to 15° C. or in the range −20° C. to 10° C.). Such organisms are typically found in environments that are permanently cold, such as the sea (or deep sea), polar ice, permafrost, glaciers and snowfields.

Thus, in some embodiments, the protein (e.g. enzyme) is a psychrophilic protein.

In some embodiments, the protein (e.g. enzyme) is from (is derived from, or originates from, or is a protein encoded by) a microorganism of a genus selected from the group consisting of *Aliivibrio, Moritella, Cenarchaeum, Colwellia* and *Streptomyces*.

In some embodiments, the protein (e.g. enzyme) is from (is derived from, or originates from, or is a protein encoded by) a microorganism of a species selected from the group consisting of *Aliivibrio wodanis, Aliivibrio salmonicida, Moritella viscosa, Cenarchaeum symbiosum* and *Colwellia psychrerythraea*.

In some embodiments, the protein (e.g. enzyme) is from (is derived from, or originates from, or is a protein encoded by) a microorganism of a species selected from the group consisting of *Aliivibrio salmonicida, Moritella viscosa, Cenarchaeum symbiosum* and *Colwellia psychrerythraea*.

In some embodiments, the protein (e.g. enzyme) is from a microorganism (e.g. a bacterium) that inhabits the same environment (or habitat) as one or more of the organisms of the above-mentioned genera or species.

In some embodiments, the protein (e.g. enzyme) is not from the genus *Aliivibrio*. In some embodiments, the protein (e.g. enzyme) is not from the species *Aliivibrio wodanis*.

In some embodiments, the protein (e.g. enzyme) has an amino acid sequence that is at least 80%, at least 85%, at least 90%, at least 95% sequence identity to a protein from (derived from, originating from, or encoded by) an organism as described above.

In some embodiments, the activity (level of activity) of the protein (e.g. enzyme) is higher than the activity of a mesophilic homologue of said protein at low temperatures. For the avoidance of doubt, and unless it is otherwise clear from the context, when referring to the activity (level of activity), or other characteristic, of a protein (e.g. enzyme) relative to the activity a mesophilic homologue, said protein is a protein from an organism having a cold environment or habitat, or is a psychrophilic protein, for example as discussed above.

A mesophilic homologue of a protein of interest is a protein of a mesophile (e.g. a mesophilic microorganism) that has the same function, and typically a related amino acid sequence (e.g at least 50%, at least 60%, at least 70% at least 80%, at least 90% or at least 95% sequence identity), as the protein of interest (protein to be produced in accordance with the invention). A skilled person is readily able to identify homologues in other organisms based on the knowledge of the function (and typically sequence) of the protein of interest. This may be done by any suitable means such as the searching of relevant sequence databases, which the skilled person will be familiar with (e.g. the BLAST databases.

Homology (e.g. sequence identity) may be assessed by any convenient method. However, for determining the degree of homology (e.g. identity) between sequences, computer programs that make multiple alignments of sequences are useful, for instance Clustal W (Thompson, Higgins, Gibson, *Nucleic Acids Res.*, 22:4673-4680, 1994). If desired, the Clustal W algorithm can be used together with BLOSUM 62 scoring matrix (Henikoff and Henikoff, *Proc. Natl. Acad. Sci. USA,* 89:10915-10919, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (Needleman and Wunsch, *J. Mol. Biol.*, 48:443, 1970) as revised by Smith and Waterman (Smith and Waterman, *Adv. Appl. Math.*, 2:482, 1981) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton, *SIAM J. Applied Math.*, 48:1073, 1988) and those described in Computational Molecular Biology, Lesk, e.d. Oxford University Press, New York, 1988, Biocomputing: Informatics and Genomics Projects.

Preferably, percentage identities described herein refer to the percentage identity over the full-length of the reference sequence, unless this is otherwise clear from the context.

Generally, computer programs will be employed for such calculations. Programs that compare and align pairs of sequences, like ALIGN (Myers and Miller, *CABIOS,* 4:11-17, 1988), FASTA (Pearson and Lipman, Proc. Natl. Acad. Sci. USA, 85:2444-2448, 1988; Pearson, *Methods in Enzymology,* 183:63-98, 1990) and gapped BLAST (Altschul et al., *Nucleic Acids Res.,* 25:3389-3402, 1997), BLASTP, BLASTN, or GCG (Devereux, Haeberli, Smithies, *Nucleic Acids Res.,* 12:387, 1984) are also useful for this purpose. Furthermore, the Dali server at the European Bioinformatics institute offers structure-based alignments of protein sequences (Holm, *Trends in Biochemical Sciences,* 20:478-480, 1995; Holm, *J. Mol. Biol.,* 233:123-38, 1993; Holm, *Nucleic Acid Res.,* 26:316-9, 1998).

By way of providing a reference point, sequences having at least 70%, 75%, 80%, 85%, 90%, 95%, 96%, 97%, 98% or 99% homology, sequence identity etc. may be determined using the ALIGN program with default parameters (for instance available on Internet at the GENESTREAM network server, IGH, Montpellier, France).

Mesophiles typically grow best at temperatures between 20° C. and 45° C.

Thus, in some embodiments, the activity (level of activity) of the protein (e.g. enzyme) is higher than the activity of a mesophilic homologue of said protein at a temperature of ≤20° C., ≤15° C., ≤10° C. or ≤5° C. (e.g. 0° C. to 20° C., or 0° C. to 15° C., or 0° C. to 10° C., or 0° C. to 5° C., or 5° C. to 15° C.). In some embodiments, the activity of the protein (e.g. enzyme) is higher than the activity of a mesophilic homologue of said protein at a temperature of about 5° C., about 10° C. or about 15° C.

An example of a mesophile (mesophilic organism) is *E. coli*. Thus, in some embodiments, the activity (level of activity) of the protein (e.g. enzyme) is higher than the activity of an *E. coli* homologue of said protein at low temperatures (e.g. one or more of the temperatures or temperature ranges described above).

In some embodiments, the activity (level of activity) of the protein (e.g. enzyme) is at least 1.5 times, at least 2 times, at least 3 times, at least 4 times, at least 5 times, at least 6 times, at least 7 times, at least 8 times, at least 9 times, or at least 10 times higher (e.g. up to 5 times or up to 10 times or up to 20 times higher) than the activity of a mesophilic (e.g. *E. coli*) homologue of said protein at low temperatures, e.g. one or more of the temperatures or temperature ranges described above.

For example, in some embodiments, the activity (level of activity) of the protein (e.g. enzyme) is at least 1.5 times, at least 2 times, at least 3 times, at least 4 times, at least 5 times, at least 6 times, at least 7 times, at least 8 times, at least 9 time or at least 10 times higher (e.g. up to 5 times or up to 10 times or up to 20 times higher) than the activity of a mesophilic (e.g. *E. coli*) homologue of said protein at 5.20° C.

In other embodiments, the activity (level of activity) of the protein (e.g. enzyme) is at least 1.5 times, at least 2 times, at least 3 times, at least 4 times, at least 5 times, at least 6 times, at least 7 times, at least 8 times, at least 9 time or at least 10 times higher (e.g. up to 5 times or up to 10 times or up to 20 times higher) than the activity of a mesophilic (e.g. *E. coli*) homologue of said protein at ≤10° C.

Alternatively viewed, in some embodiments, the activity (level of activity) of the protein (e.g. enzyme) is at least 50%, at least 100%, at least 200%, at least 300%, at least 400%, at least 500%, at least 600%, at least 700%, at least 800%, at least 900%, or at least 1000% higher (e.g. up to 500%, up to 1000% or up to 2000% higher) than the activity of a mesophilic (e.g. *E. coli*) homologue of said protein at low temperatures, e.g. one or more of the temperatures or temperature ranges described above.

In some embodiments, the activity (level of activity) of the protein (e.g. enzyme) is at least 50%, at least 100%, at least 200%, at least 300%, at least 400%, at least 500%, at least 600%, at least 700%, at least 800%, at least 900%, or at least 1000% higher (e.g. up to 500%, up to 1000% or up to 2000% higher) than the activity of a mesophilic (e.g. *E. coli*) homologue of said protein at ≤20° C.

In some embodiments, the activity the protein (e.g. enzyme) is at least 50%, at least 100%, at least 200%, at least 300%, at least 400%, at least 500%, at least 600%, at least 700%, at least 800%, at least 900%, or at least 1000% higher (e.g. up to 500%, up to 1000% or up to 2000% higher) than the activity of a mesophilic (e.g. *E. coli*) homologue of said protein at ≤10° C.

The activity of the protein (e.g. relative to the activity of a mesophilic homologue) may be tested by any appropriate method (which could be a cell based method or a method which assesses the activity of the purified or isolated protein, e.g. affinity purified protein) and will depend on the type of protein (e.g. enzyme) being tested. A skilled person could readily identify an appropriate method or assay to use. Purely by way of example, if the protein is an Exonuclease I or a DNA polymerase II a molecular beacon assay could be used, e.g. one of the molecular beacon assays described in the Example section herein, to assess (or measure or determine) activity at one or more of the temperatures described above (e.g. ≤20° C., ≤15° C., ≤10° C. or ≤5° C.).

In some embodiments, the protein (e.g. enzyme) is more thermolabile than a mesophilic homologue of said protein. Put another way, the protein (e.g. enzyme) may be less thermostable than a mesophilic homologue of said protein. For the avoidance of doubt, and unless it is otherwise clear from the context, when referring to the themolability or thermostability of a protein (e.g. enzyme) relative to the themolability or thermostability of a mesophilic homologue, said protein is a protein from an organism having cold environment or habitat, or is a psychrophilic protein, for example as discussed above.

In some embodiments, a protein (e.g. enzyme) may be substantially inactivated at a temperature at which a mesophilic homologue of said protein is not substantially inactivated. In some embodiments, a protein such as an enzyme may be inactivated at a temperature at which a mesophilic homologue of said protein is not inactivated. In some embodiments, a protein (e.g. enzyme) may be irreversibly inactivated at a temperature at which a mesophilic homologue of said protein is not irreversibly inactivated.

In some embodiments, the temperature at which a protein (e.g. enzyme) is substantially inactivated is lower than (e.g. at least 5° C., at least 10° C., at least 15° C. or at least 20° C. lower) the temperature at which a mesophilic homologue of said protein is substantially inactivated. In some embodiments, the temperature at which a protein (e.g. enzyme) is inactivated is lower than (e.g. at least 5° C., at least 10° C., at least 15° C. or at least 20° C. lower) the temperature at which a mesophilic homologue of said protein is inactivated. In some embodiments, the temperature at which a protein (e.g. enzyme) is irreversibly inactivated (or denatured) is lower than (e.g. at least 5° C., at least 10° C., at least 15° C. or at least 20° C. lower) the temperature at which a mesophilic homologue of said protein is irreversibly inactivated (or denatured).

The skilled person would be readily able to determine whether or not a given protein (e.g. enzyme) is substantially inactivated (e.g. has a reduction in activity of at least 70%, at least 80% or at least 90% or at least 95%), inactivated or irreversibly inactivated at a given temperature relative to a mesophilic homologue of said protein by exposing samples (or preparations) of the protein and the mesophilic homologue of the protein to the given temperature (e.g. about 35° C., about 37° C., about 40° C., about 45° C., about 50° C., about 55° C., about 60° C., about 65° C., about 70° C. or about 75° C.) for a period of time (e.g. at least 5 minutes, at least 10 minutes, at least 30 minutes, at least 1 h, at least 2 h, at least 12 h, or more) and subsequently testing (or measuring) the activity of the protein in an appropriate assay. The assay would depend on the type of protein being tested. By way of example, if the protein is an Exonuclease I or a DNA polymerase II a molecular beacon assay could be used, e.g. one of the molecular beacon assays described in the Example section herein, could be used to assess (or measure or determine) activity.

In some embodiments, the protein (protein to be produced), e.g. an enzyme, exhibits a substantial proportion of its maximum activity (e.g. enzymatic activity) at low temperatures (e.g. ≤20° C., ≤15° C., ≤10° C. or ≤5° C.).

In some embodiments, the protein (protein to be produced), e.g. an enzyme, exhibits at least of 20%, at least 30%, at least 40%, at least 50%, at least 60%, at least 70%, at least 80%, at least 90% at least 95% or 100% of its maximum activity (e.g. enzymatic activity) at a temperature of ≤20° C. (e.g. at a temperature of 0° C.-20° C. or 4° C.-20° C., e.g. about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C. or 20° C.).

In some embodiments, the protein (protein to be produced), e.g. an enzyme, exhibits at least of 20%, at least 30%, at least 40%, at least 50%, at least 60%, at least 70%, at least 80%, at least 90% at least 95% or 100% of its maximum activity (e.g. enzymatic activity) at a temperature of 15° C. (e.g. at a temperature of 0° C.-15° C. or 4° C.-15° C.).

In some embodiments, the protein (protein to be produced), e.g. an enzyme, exhibits at least of 20%, at least 30%, at least 40%, at least 50%, at least 60%, at least 70%, at least 80%, at least 90% at least 95% or 100% of its maximum activity (e.g. enzymatic activity) at a temperature of ≤10° C. (e.g. at a temperature of 0° C.-10° C. or 4° C.-10° C.).

In some embodiments, the protein (protein to be produced), e.g. an enzyme, exhibits at least of 20%, at least 30%, at least 40%, at least 50%, at least 60%, at least 70%, at least 80%, at least 90% at least 95% or 100% of its maximum activity (e.g. enzymatic activity) at a temperature of ≤5° C. (e.g. at a temperature of 0° C.-5° C. or 2° C.-5° C. or 4° C.-5° C.).

The activity (level of activity) of a protein relative to its maximum activity may be tested by any appropriate method (which could be a cell based method or a method which assesses the activity of the purified protein, e.g. affinity purified protein) and will depend on the type of protein (e.g. enzyme) being tested. The maximum activity of the protein can be determined by, for example, measuring the activity of the protein at a number of different temperatures across a temperature range (e.g. 0° C. to 80° C., e.g. in 5° C. intervals) and establishing which temperature provides the highest protein (e.g. enzyme) activity. The activity at this temperature can be set as the "maximum activity" temperature. A skilled person could readily identify an appropriate method or assay to use. Purely by way of example, if the protein is an Exonuclease I or a DNA polymerase II a molecular beacon assay, e.g. one of the molecular beacon assays described in the Example section herein, could be used to assess (or measure or determine) activity.

(Active) fragments of proteins (e.g. enzymes) may also be produced by methods of the present invention. Thus, references herein to proteins (e.g. enzymes) encompass such (active) fragments (e.g. enzymatically active fragments) unless otherwise clear from the context. Such fragments typically represent at least 70%, at least 80%, at least 90%, or at least 95% of the length of the full-length protein.

In one embodiment, the protein is an Exonuclease I from *Aliivibrio salmonicida* (AsExoI). The AsExoI amino acid sequence is:

(SEQ ID NO: 37)
MPQDNAPSFFFFDYETWGTSPSLDRPCQFAGVRTDEDFNIIGEPLVIYCR

PPIDYLPSPEACLITGITPQMAVSKGLSEPEFIAQIHNELSKPNTCSLGY

NNIRFDDEVSRYTLYRNFFEPYGWSWQNGNSRWDLLDVMRAVYALRPEGI

EWPKDEEGKPSFRLEKLSQANGIEHENAHDAMADVIATIELAKVVKKAQP

KMFNYLLSMRHKKKAATLIDIIEMTPLMHVSGMFGVDRGNISWIVPVAWH

PTNNNAVITIDLALDPAVFLELDAEQLHQRMYTKRSELGPDELPVPVKLV

HLNKCPILAPAKTLTAENAIALNVDREACLRNLKVIRENPEIRQKLIDLY

NIEPGYEKSSNVDTLLYDGFFSHADKTAIDMIRQSTPEQLIDFEPNVSDP

RIKPLLFRYRARNFPHTLNESEQLRWQAHLQDYFETHMSDYETRFESLYL

ESEGNEKKTAILRAVYNYVQQLVS

In one embodiment, the protein is a DNA polymerase II from *Aliivibrio salmonicida* (AsPoIII). The AsPoIII amino acid sequence is:

(SEQ ID NO: 38)
LNSPHCGFLLTRQNKDIRDHSLVDLWVKCDDHIAHLLIENELAVIFFLKE

RQAEYESILTNAHIHYSIKSTSLHTFQHQPVFGLYFSSTQQKRVATALFE

DHQLPTFEGDIRLADRYLMERFICGGMAFVGTPRQRKGYVEYRDVKIKSA

EMTPEFSVVSLDVECSEKGILYSVALHCERDTRIIMVGPEETSDLPIEWV

ENEKALLLALESWFQTFDPDIIIGWNVINFDFNLLIKRAKWHNLAFRLGR

GNSSLYFRESNKNRQQGFLSFPGRVVLDGIDALKTATYHFSSWSLESVSQ

ELLNEGKSIHDPSDRMGEINRMYREDKCALAKYNLQDCVLVTRIFELTHL

LEFVIERTKLTGIELDRVGGSVAAFTNLYLPRLHRAGYIAPNLESENWIA

SPGGYVMSSKPGLYESVLVLDFKSLYPSIIKTFRIDPLGLVEGLKLESGI

DDGQAIEGFRGGRFHRTKHFLPNLIETLWSARDVAKKNNEKAFSQAIKII

MNSFYGVLGSSGCRFFDHRLASSITMRGHEIMKTTRELIESQGYEVIYGD

TDSTFVTLGESMPSDEADKIGKQLVDHINQWWTAHLESEYAIDSALEIEY

ETHYRIFLMPTIRGSEMGSKKRYAGLIRKGDKEEIIFKGLETVRTDWTPL

SQEFQKVLFDKVFHQQAVEEYVREYVDKTKSGEFDNKLIYRKRLRRQLDE

YQKNVPPHVKAARIADTQNQKLGKPLMYQQGGWIEYIITTAGPEPIEYRQ

NPIDYDHYVEKQLKPIAEGILPFVNLSFTELSASQLGLF

In one embodiment, the protein is an Exonuclease I from *Moritella viscosa* (MvExoI). The MvExoI amino acid sequence is:

(SEQ ID NO: 39)
MDNNSNKTATDLPTFYWHDYETFGLSPSLDRPSQFAGIRTDMDFNVIGEP

DMFYCRQSDDYLPSPEAAMITGITPQKTQAEGVSEAEFSKRIEAQFSQKN

TCIIGYNNIRFDDEVTRNIFYRNFYDPYAHTWKDGNSRWDIIDLMRACYA

LRPEGIVWPENDDGLPSMRLELLTAANGIEHANAHDATSDVYATIAMAKL

VKEKQPKLFDFLFNLRSKRKVESLVDIINMTPLVHVSGMFGADRGFTSWV

VPLAWHPTNNNAVIVADLAQDITPLLELSADELRERLYTPKKDLGDLTPI

PLKLIHINKCPVLAPAKTLLPENAERLGIDRSACLANLKRLKESATLREN

VVGVYQVEREYPKSTNVDAMIYDGFFSAGDKANFEILRETAPEQLTGLQL

KVSDSRFNELFFRYRARNFPHLLSMPEQQKWLDHCRTVLEDSAPAYFARL

DALAIENSHDERKMKLLQQLYLYGQKIIGA

In one embodiment, the protein is a ligase (e.g. ligase 1) from *Cenarchaeum symbiosum* (CsLig1). The ligase is a DNA ligase. The CsLig1 amino acid sequence is:

(SEQ ID NO: 40)
QFSVLAGSLEKMESTAKRLELTGILEELLRETPHEVIAQIVYLIQGKLRP

EFEGIELGVAEKLAVRAVSKSSGMPAARIEAAYRRDGDLGRAASSILEQK

TQTTFLAEEITVERVYDTLMRIARLEGARSQDMKMRHISSLLNDASPRDA

CYILKLILGTLRLGIAENTVMDALAAAFTGSKSNRPELERAYNVSSDLGR

VAEAVSSGGLEAVRGFAVAVFSPIRPMLADRVRSESEALEKMGAGLAAEY

KLDGERVQVHLSGGRVELFSRSLENITAYYPDIVERIPGRLRAREAVLEA

EAVAVNEETGEFLPFQELMHRRRKYDIDKAVMRYPITVNFFDILYLDGRD

CLGISYSERRALLEGVVDEDSFARCVPVSTIPDESALEDSLENSINAGCE

GLMLKLPDAPYRAGSRGGYWLKLKREYRNELGDSLDLVIIGAFFGKGRRT

GRYGTLLLATYDDSRDTFPSICKVGTGFTDEDLDQLYQLLSPRVTLKRNP

RIDSGMEADVWFDPEVVMEVVASEITLSPVHKTALDSVRKGAGLALRFPK

FTGKLRTEKTAEDASTDQEVIALYKSQKKVVPDGQPGV

In one embodiment, the protein is a ligase (e.g. ligase 6) from *Colwellia psychrerythraea* (CpLig6). The ligase is a DNA ligase. The CpLig6 amino acid sequence is:

(SEQ ID NO: 41)
QQTTQKTQKFKPNIQHGVSYQKVDDISQYYVSEKLDGIRGYWDGKQLFTR

RGNLINSPSWFTQHWPTYPMDGELWLARGQFQLLLSCATKRIAVENKTTS

CWRSVRFMIFDLPKHLGDFNERVIKMRTLLVQNQSVYLAMIDQVKLEELS

ALDHKLDEVIATHGEGLMLHLASAHYQQGRNPALMKLKKYQDAEATVIGY

TEGKGKYQNQLGAIKVKTSDGIIFKIGSGLSDIQRANPPKIGTIITFKYN

GLTQAGIPRFARFWRIKASG

In one embodiment, the protein is an alcohol dehydrogenase from *Streptomyces* (AdhStrep). The AdhStrep amino acid sequence is:

(SEQ ID NO: 42)
MGRAVVFEEFGKEARVQDVADPSPSRDGVVVRVEATGLCRSDWHGWMGHD

PDITLPHVPGHELAGVVEAVGRDVVDRRPGDRVTVPFVCACGRCAACAAG

AQQVCERQTQPGFTHWGSFAEYVALERADVNLVPVPHGMSFGTAAALGCR

FATAFRAVVARGRVAPGEWVAVHGCGGAGLSAVMIAVACGARVVAVDVSP

EALRLARTFGAAECVDASAHPEGVDAAVRELTGGGAQLSLDALGSPVTCA

ASVRSLRRQGRHVQVGLLPPAAGDPVVPMARVIALELELLGSHGMAAHAY

PPMMDMVRSGSLRPDLLVTSTIGLDAAPAALAAMSAGPGPGAGVTVIEPT

RRPHPDGA

In some embodiments, the protein (protein to be produced) is a protein that is difficult to express in mesophilic organisms (e.g. mesophilic microorganisms such as *E. coli*). In some embodiments, the protein is a protein that forms inclusion bodies when expressed in mesophilic microorganisms such as *E. coli*. In some embodiments, the protein is a protein that, when expressed in a mesophilic organism (e.g. *E. coli*), is not present, or is only present in small proportion (e.g. <10% or <5%), in the soluble fraction after cell lysis.

In some embodiments, the protein is a protein of the Immunoglobulin (Ig) superfamily. In some embodiments, the protein is an antigen binding protein such as an antibody, or an antigen binding fragment thereof. In some embodiments, the protein is, or comprises, an antibody chain (e.g. a heavy chain or a light chain such as the heavy chain of IgG or the light chain of IgG). In some embodiments, the protein is, or comprises, a variable domain (or variable region) of an antibody (e.g. a variable heavy (VH) domain and/or a variable light (VL) domain of an antibody). In some embodiments, the protein is a scFv molecule (single-chain variable fragment).

In some embodiments, the protein (protein to be produced) further comprises a fusion moiety that aids in the purification of the protein by acting as a ligand in affinity purification (for example appropriate "tags" to enable purification and/or identification may be present, e.g., His tags such as a 6× His tag or myc tags). Such fusion moieties are typically amino acid based (e.g. a 6× His tag) and may be provided at the N-terminus and/or the C-terminus of the protein. In some embodiments, an N-terminal fusion moiety (tag) may be provided immediately before (N-terminal to) the first amino acid of the protein (protein to be produced), i.e. the first (N-terminal) amino acid of the protein (protein to be produced) being immediately C-terminal to (the next amino acid to) the last (C-terminal) amino acid of the tag. In some embodiments, a C-terminal fusion moiety (tag) may be provided immediately after (C-terminal to) the last amino acid of the protein (protein to be produced), the last (C-terminal) amino acid of the protein (protein to be produced) being immediately N-terminal to (the next amino acid to) the first (N-terminal) amino acid of the tag. In some embodiments, there may be an amino acid linker (such as a 1-20 or 1-10 or 1-5 amino acid linker) between the fusion moiety (tag) and the protein.

In some embodiments, the protein (protein to be produced) may also comprise a fusion moiety (or fusion peptide or fusion "tag") that provides increased expression of the protein and/or increased solubility and/or increased secretion of the recombinant protein. Thus, in some embodiments, the protein is a fusion protein comprising (or consisting of) a fusion moiety (e.g. as described herein) and protein of interest.

The present inventors have advantageously found that if a protein (protein to be produced) is in the form of a fusion protein having a fusion moiety (or tag) having the amino acid sequence MSKQMKFGLLPAAIAGALLS (SEQ ID NO:1), the production (or expression) of the protein (protein to be produced) in *Aliivibrio wodanis* is increased (or elevated).

Thus, in some embodiments, the protein (protein to be produced) is a fusion protein comprising (or consisting of) (i) a fusion moiety (or tag) comprising (or consisting of) an amino acid sequence of SEQ ID NO:1 or an amino acid sequence that is at least 70% (e.g. at least 75%, at least 80%, at least 85%, at least 90% or at least 95%) identical to SEQ ID NO:1, and (ii) a protein (protein to be produced or protein of interest).

Put another way, in some embodiments, the protein is additionally provided with a fusion moiety (or tag) comprising (or consisting of) an amino acid sequence of SEQ ID NO:1 or an amino acid sequence that is at least 70% (e.g. at least 75%, at least 80%, at least 85%, at least 90% or at least 95%) identical to SEQ ID NO:1.

In some embodiments, the fusion moiety (or tag) consists of an amino acid sequence of SEQ ID NO:1 or an amino acid sequence that is at least 70% (e.g. at least 75%, at least 80%, at least 85%, at least 90% or at least 95%) identical to SEQ ID NO:1.

In preferred embodiments, the fusion moiety (or tag) consists of an amino acid sequence of SEQ ID NO:1.

In embodiments in which a fusion moiety (or tag) comprising (or consisting of) an amino acid sequence of SEQ ID NO:1 or an amino acid sequence that is at least 70% (e.g. at least 75%, at least 80%, at least 85%, at least 90% or at least 95%) identical to SEQ ID NO:1 is employed, preferably the fusion moiety is provided as an N-terminal tag (i.e. is present, or fused, at the N-terminus of the protein or is located N-terminally with respect to the protein of interest).

A fusion moiety based on SEQ ID NO:1 as discussed above may be used in conjunction with any protein to be produced. In some preferred embodiments, if the protein is not from the genus *Aliivibrio*, the protein is provided with a fusion moiety (or tag), preferably an N-terminal fusion moiety, comprising (or consisting of) an amino acid sequence of SEQ ID NO:1 or an amino acid sequence that is at least 70% (e.g. at least 75%, at least 80%, at least 85%, at least 90% or at least 95%) identical to SEQ ID NO:1.

In some embodiments, an N-terminal fusion moiety (tag) based on SEQ ID NO:1 (as described above) may be provided immediately before (immediately N-terminal to) the first amino acid of the protein (protein of interest e.g. enzyme), i.e. the first (N-terminal) amino acid of the protein (protein of interest e.g. enzyme) being immediately C-terminal to (the next amino acid to) the last (C-terminal) amino acid of the tag (i.e. with no amino acids in between). In some embodiments, there may be an amino acid linker such as a 1-20, 1-10 or 1-5 amino acid linker) between the fusion moiety (tag) and the protein.

In some embodiments, the fusion moiety may comprise (or consist of) a fragment (or portion) of an amino acid sequence of SEQ ID NO:1 or a fragment (or portion) of an amino acid sequence that is at least 70% (e.g. at least 75%, at least 80%, at least 85%, at least 90% or at least 95%) identical to SEQ ID NO:1. In some embodiments, the fragment is at least 14 amino acids in length or at least 15 amino acids in length, preferably at least 16 amino acids in length or at least 17 amino acids in length, more preferably at least 18 amino acids in length or at least 19 amino acids in length. Preferably, the fragment has at least 70%, at least 75%, at least 80%, at least 85%, at least 90% or at least 95% sequence identity to SEQ ID NO:1.

In some embodiments, a fusion moiety comprising (or consisting of) an amino acid sequence of SEQ ID NO:1, or an amino acid sequence that is at least 70% identical to SEQ ID NO:1, further comprises at its C-terminal end an amino acid sequence comprising (or consisting of) GNAFA (SEQ ID NO:51) or comprising (or consisting of) an amino acid sequence having 1, 2 or 3 (preferably 1 or 2, more preferably 1) amino acid insertions, deletions or substitutions as compared to the amino acid sequence GNAFA (SEQ ID NO:51).

In some preferred embodiments, a fusion moiety comprising (or consisting of) an amino acid sequence of SEQ ID NO:1, or an amino acid sequence that is at least 70% identical to SEQ ID NO:1, further comprises at its C-terminal end an amino acid sequence comprising (or consisting of) GNAFA (SEQ ID NO:51).

A particularly preferred fusion moiety comprising the amino acid sequence of SEQ ID NO:1 is a fusion moiety comprising (or consisting of) the amino acid sequence of SEQ ID NO:4 (MSKQMKFGLLPAAIAGALLSGNAFA).

SEQ ID NO:4 corresponds to SEQ ID NO:1 but has an additional 5 amino acids (GNAFA; SEQ ID NO:51) at the C-terminal end as compared to SEQ ID NO:1. The inventors have found that a peptide having the amino acid sequence of SEQ ID NO:4 can be used as a fusion moiety to enhance expression and secretion of a protein.

Thus, in some embodiments, the protein (protein to be produced) is a fusion protein comprising (or consisting of) (i) a fusion moiety (or tag) comprising (or consisting of) an amino acid sequence of SEQ ID NO:4 or an amino acid sequence that is at least 70% (e.g. at least 75%, at least 80%, at least 85%, at least 90% or at least 95%) identical to SEQ ID NO:4, and (ii) a protein (protein to be produced or protein of interest).

The discussion elsewhere herein in connection with SEQ ID NO:1-related fusion moieties and fusion proteins comprising SEQ ID NO:1-related fusion moieties and methods and uses involving such fusion moieties and fusion proteins, e.g. of preferred features, may be applied *mutatis mutandis* to of SEQ ID NO:4-related embodiments of the present invention.

In some embodiments, the fusion moiety may comprise (or consist of) a fragment (or portion) of an amino acid sequence of SEQ ID NO:4 or a fragment (or portion) of an amino acid sequence that is at least 70% (e.g. at least 75%, at least 80%, at least 85%, at least 90% or at least 95%) identical to SEQ ID NO:4. In some embodiments, the fragment is at least 14 amino acids in length or at least 15 amino acids in length, preferably at least 16 amino acids in length or at least 17 amino acids in length or at least 18 amino acids in length or at least 19 amino acids in length, more preferably at least 20 amino acids in length, at least 21 amino acids in length, at least 22 amino acids in length, at least 23 amino acids in length or at least 24 amino acids in length. Preferably, the fragment has at least 70%, at least 75%, at least 80%, at least 85%, at least 90% or at least 95% sequence identity to SEQ ID NO:4.

In some embodiments, fusion moieties comprising (or consisting of) an amino acid sequence that is at least 70% (e.g. at least 75%, at least 80%, at least 85%, at least 90% or at least 95%) identical to SEQ ID NO:4 (or fragments thereof) have no more than 3 (preferably 1 or 2, more preferably 1, and most preferably no) amino acid insertions, deletions or substitutions in the GNAFA (SEQ ID NO:51) amino acid motif of SEQ ID NO:4.

In preferred embodiments, the protein to be produced by methods of the present invention (protein of interest) is not a protein encoded by the Awod_I1781 gene of *Aliivibrio wodanis*. The Awod_I1781 gene may also be referred to as the AW0309160_00174 gene (i.e. Awod_I1781 and AW0309160_00174 may be considered synonyms). The protein encoded by the Awod_I1781/AW0309160_00174 gene has the amino acid sequence set forth as SEQ ID NO:

(SEQ ID NO: 48)
MSKQMKFGLLPAAIAGALLSGNAFAGTEACIEVFKSAANDYQEHNVLYTA

ASCNFATVGGTTANSLRANDSADIAYELTKNLDLNFEAVDQDDAAETLNI

VYVPTSDIPAASRLKFRLNGATFANNSNIIYLVKAEADSATGITTKYSAV

ASTDGAVDGENVITFIVTDLIGAGTRLVLSLENQPTLDLTGAVENRTTFE

SPAINIANPEVCTPNDKVTLEVIEAKSDFGQDIKGAVTNPATNKLADLVD

IQKQFTLLHDAQLTTEALVDAESPSYRGQFVFSKTDTGLWVNQTTEQGLF

WESTIQNKISSLDQYVEIDTEDRLRVRLNPEGSLGGVMNFAMLYNDTTRA

NTPLDASEDSHISTEAQYMYNYNTTGNRWTNVKDTAQEYSYNIYDVVNGE

-continued

DSARIAMQLEGNGQPMSFNYLLNASLGLEFKDVKLQDDTYCQTKTPFKVG

VNGATLKVPHTTNNPANFVRITNEHVTGAEVSVTVFDENSTTAANEITFV

LNAENGFSEELGPKDSIVYKSDKIIKKYAELLKAKTGLDALKTSDRVSMT

FVVTAPKDTVHATSVIKGPGNTDRVMAVLDNNKWSQ.

In some embodiments, the protein to be produced by methods of the present invention is not a protein comprising (or consisting of) the amino acid sequence of SEQ ID NO:48. In some embodiments, the protein to be produced by methods of the present invention is not a protein comprising (or consisting of) an amino acid sequence that is at least 60% identical (or at least 70%, at least 80% or at least 90% identical) to the amino acid sequence of SEQ ID NO:48.

In some embodiments, the protein to be produced by the methods of the present invention is not a protein of SEQ ID NO:49. In some embodiments, the protein to be produced by methods of the present invention is not a protein comprising (or consisting of) an amino acid sequence that is at least 60% identical (or at least 70%, at least 80% or at least 90% identical) to the amino acid sequence of SEQ ID NO:49.

(SEQ ID NO: 49)
MSKQMKFGLLPAAIAGALLSGNAFAGTEACIEISKTTASYTELAAADLYE

GSACSYTGTSTDKDLLPNNSAKIAYELTKVADYDLEDITKTAYTGKASDD

LSIVYVPTTDVPPAARLTFKLNNATFAVDENIIHLVKVEEDSQNPGSYIY

TAVASSDGQVDGESTALFMVKSGVTVGAGTRLFLSTSNQPTALTGITTPG

IHLEFTEECTVDQKVTLEVIDAKTDFGFVIAGAKTQAASDLVVAERQYQL

AVEKNLPVGQLTLTVEADVNAEDPSQRKFFLTNTGAGELAPPAGGWDNQT

TAKSVVWEAYFQNNFNSLDLAHVLRPEDKVLLDTNSPKYTGTAITLGALT

QMTNATTALDKMTNSHLAANTNHVDFNETTEWATLNSSLTSYHFDAEEVF

GPTDLTGADTDRALALVLATNGTTPMNFGYSVDAKFGMDLADVTGGLFTY

HDTATSCNPTTPFAIDVNGAVLKVPYAYNTDKNWVRITNEHDTEAEVTVE

VFDENDAAGDKRILTLAKIGADDSTVYKADAIIALYEAEIGRASSNRVSM

TFTVTAPKDTVHGVSVQAIPGGVDRVLPVLDQNNWNQ

In preferred embodiments, a protein (protein produced) in accordance with the present invention is not a naturally occurring protein that comprises SEQ ID NO:1 or SEQ ID NO:4 (or that comprises a fragment or variant of SEQ ID NO:1 or SEQ ID NO:4 as described herein), i.e. is not a protein that naturally comprises SEQ ID NO:1 or SEQ ID NO:4 (or that naturally comprises a fragment or variant of SEQ ID NO:1 or SEQ ID NO:4 as described herein).

In some embodiments, a fusion moiety based on SEQ ID NO:1 or SEQ ID NO:4 as discussed above may be provided in addition to a fusion moiety that aids in the purification of the protein (e.g. a 6× His tag) and/or a fusion moiety that provides increased expression of the protein and/or increased solubility of the recombinant protein. In some embodiments, a fusion moiety based on SEQ ID NO:1 or SEQ ID NO:4 as discussed above and a fusion moiety that aids in the purification of the protein (e.g. a 6× His tag) and/or a fusion moiety that provides increased expression of the recombinant protein may each be positioned N-terminally relative to the protein of interest. In some such embodiments, a fusion moiety based on SEQ ID NO:1 or SEQ ID NO: 4 may be positioned either N-terminally or C-terminally relative to a fusion moiety that aids in the purification of the protein (e.g. a 6× His tag) and/or a fusion moiety that provides increased expression of the protein and/or increased solubility of the recombinant protein. In other embodiments, a fusion moiety based on SEQ ID NO:1 or SEQ ID NO:4 as discussed above may be positioned N-terminally relative to the protein of interest and a fusion moiety that aids in the purification of the protein (e.g. a 6× His tag) and/or a fusion moiety that provides increased expression of the protein and/or increased solubility of the recombinant protein may be positioned C-terminally to the protein of interest.

Unless otherwise clear from the context, the terms "N-terminal" and "N-terminally" mean positioned N-terminal relative to the protein of interest. For example, in some preferred fusion proteins described herein, an N-terminal "tag" (or moiety) may be positioned at the extreme N-terminus of the fusion protein (with the first (i.e. N-terminal) amino acid of the "tag" being the first (i.e. N-terminal) amino acid of the fusion protein). In other examples, in fusion proteins described herein, an N-terminal "tag" (or moiety) may be positioned N-terminally relative to the protein of interest, but there may be one or more additional amino acids N-terminal to the "tag". The same applies, *mutatis mutandis*, to the terms "C-terminal" and "C-terminally".

For the avoidance of doubt, in the context of the present invention a fusion protein is a single protein (single polypeptide chain) comprising a protein (protein of interest) and one or more fusion moieties. Fusion proteins may be considered to be chimeric proteins or hybrid proteins. Fusion proteins comprise at least two different polypeptide sequences which do not occur together in the same protein (or same polypeptide) in nature. Thus, fusion proteins in accordance with the present invention do not have naturally occurring counterparts. Fusion proteins may thus be considered artificial proteins or non-native proteins or non-natural proteins or non-wildtype proteins. Fusion proteins can be considered proteins which comprise two unrelated polypeptide sequences.

Methods of the present invention comprise culturing an *Aliivibrio wodanis* host cell comprising a heterologous nucleic acid molecule encoding a protein. By "heterologous nucleic acid molecule" is meant a nucleic acid molecule (or polynucleotide) that is not normally found in the host organism, i.e. not normally found in *Aliivibrio wodanis* or not native to *Aliivibrio wodanis*. Thus, heterologous nucleic acid molecules include non-*Aliivibrio wodanis* nucleic acid molecules, i.e. polynucleotide sequences that are not present in *Aliivibrio wodanis*. Typically, "heterologous nucleic acid molecules" have been introduced into the *Aliivibrio wodanis* by transformation or conjugation as discussed elsehere herein. Although a protein encoded by a heterologous nucleic acid molecule in accordance with the present invention is typically not an *Aliivibrio wodanis* protein, in some embodiments, an *Aliivibrio wodanis* protein may be produced in accordance with the present invention if said protein is expressed from an expression vector and/or its expression is under the control of a non-native regulatory sequence (e.g. promoter). A "heterologous nucleic acid molecule" may also be considered a "heterologous polynucleotide".

Typically, the heterologous nucleic acid molecule encoding the protein is, or is on (i.e. encoded on or expressed from), an expression vector (e.g. a plasmid).

Possible expression vectors (or recombinant expression vectors) include but are not limited to cosmids or plasmids, so long as the vector is compatible with *Aliivibrio wodanis*.

The skilled person is able to identify suitable expression vectors. Exemplary and preferred expression vectors are described in the Example section herein (see e.g. Table 4). The expression vectors are suitable for transformation or conjugation of a host cell, which means that the expression vectors contain a nucleic acid molecule and regulatory sequences selected for expression in *Aliivibrio wodanis*, which are operatively linked to the nucleic acid molecule. Operatively linked is intended to mean that the nucleic acid is linked to regulatory sequences in a manner that allows expression of the nucleic acid molecule. Thus expression vectors typically have the necessary regulatory sequences for the transcription and translation of the protein sequence encoded by the nucleic acid molecule.

Suitable regulatory sequences may be derived from a variety of sources, including bacterial, fungal, viral, mammalian, or insect genes and are well known in the art. Selection of appropriate regulatory sequences may be readily accomplished by one of ordinary skill in the art. Examples of such regulatory sequences include: a transcriptional promoter and enhancer or RNA polymerase binding sequence, a ribosomal binding sequence, including a translation initiation signal.

In some embodiments, the regulatory sequence is an inducible promoter (e.g. an IPTG inducible promoter).

In some embodiments, protein expression is under the control of the $P_{trc}$ promoter. $P_{trc}$ is a well-characterised IPTG inducible promoter.

In some embodiments, protein expression is under the control of the $P_{lac}$ promoter. $P_{lac}$ is a well-characterised promoter.

In some embodiments, protein expression is under the control of a promoter comprising (or consisting of) a polynucleotide of SEQ ID NO:3 or a sequence having at least 70% (e.g. at least 75%, at least 80%, at least 85%, at least 90% or at least 95%) sequence identity to SEQ ID NO:3.

Additionally, other sequences, such as an origin of replication, additional DNA restriction sites, enhancers, and sequences conferring inducibility of transcription may be incorporated into the expression vector.

Expression vectors may also contain a selectable marker gene (e.g. an antibiotic resistance gene) that facilitates the selection of host cells transformed or or conjugated with an expression vector.

The recombinant expression vectors may also contain genes that encode a fusion moiety that provides increased expression of the protein; increased solubility of the protein; and aid in the purification of the target protein by acting as a ligand in affinity purification (for example appropriate "tags" to enable purification and/or identification may be present, e.g., His tags or myc tags).

Expression vectors can be introduced into the *Aliivibrio wodanis* host cells by any appropriate means (e.g. transformation or conjugation as described elsewhere herein). Suitable methods for introducing expression vectors into heterologous host cells can be found in Sambrook et al., 1989 (Sambrook, Fritsch and Maniatis, *Molecular Cloning: A Laboratory Manual*, 2nd Ed., Cold Spring Harbor Press, Cold Spring Harbor, N.Y., 1989) and other laboratory textbooks.

In some preferred embodiments, the expression vector is a plasmid. In some embodiments, the expression vector is a plasmid that is capable of being maintained extrachromasomally in the cell (e.g. as a circular plasmid). In some embodiments, the expression vector is a plasmid that is capable of being integrated into the host cell chromosome.

In some embodiments the plasmid is, or is based on, the plasmid pTM214 (described in Miyashiro et al. (2011)).

In some embodiments the plasmid is, or is based on, the plasmid pNQ705 (described in Milton et al. (1992)).

In some embodiments the plasmid is, or is based on, the plasmid pVSV208 (described in Dunn et al. (2006)).

In some embodiments the plasmid is, or is based on, the plasmid pVSV105 (described in Dunn et al. (2006)).

In some embodiments, the plasmid is, or is based on, the plasmid pPSY001 described in the Example section herein and depicted in FIG. 2A.

In some embodiments, the plasmid has a promoter comprising (or consisting of) a polynucleotide of SEQ ID NO:3 or a sequence having at least 70% (e.g. at least 75%, at least 80%, at least 85%, at least 90% or at least 95%) sequence identity to SEQ ID NO:3, said promoter directing the expression (or driving or controlling) the expression of the protein.

As set out elsewhere herein, the present inventors have found that if a protein (protein to be produced) is in the form of a fusion protein having a fusion moiety (or tag) having the amino acid sequence MSKQMKFGLLPAAIAGALLS (SEQ ID NO:1), the production of the protein in *Aliivibrio wodanis* is increased. The 60 base pair nucleotide sequence ATGAGTAAGC AAATGAAGTT TGGACTTCTT CCAGCAGCGA TCGCTGGTGC ATTACTGAGC (SEQ ID NO:2) encodes this fusion moiety. Without wishing to be bound by theory, it is believed the RNA molecule corresponding to this sequence is capable of forming a strong RNA secondary structure having three base-paired regions and two terminal loops (see FIG. 6B) and that this may contribute to the increase in protein expression observed in the present of the fusion moiety.

The inventors have also found that if a protein (protein to be produced) is in the form of a fusion protein having a fusion moiety having the amino acid sequence MSKQMKFGLLPAAIAGALLSGNAFA (SEQ ID NO:4), the expression level of the protein in *Aliivibrio wodanis* is increased and the level of secretion of the protein from *Aliivibrio wodanis* is increased. The 75 nucleotide sequence 5'-ATGAGTAAGC AAATGAAGTT TGGACTTCTT CCAGCAGCGA TCGCTGGTGC ATTACTGAGC GGCAACGCAT TCGCT-3' (SEQ ID NO:5) encodes the fusion moiety of SEQ ID NO:4.

Thus, in some embodiments, the nucleic acid molecule encoding the protein (protein to be produced) is a nucleic acid molecule comprising (or consisting of) (i) a polynucleotide comprising (or consisting of) a polynucleotide sequence of SEQ ID NO:2 or SEQ ID NO:5 or a nucleotide sequence that is at least 70% (e.g. at least 75%, at least 80%, at least 85%, at least 90% or at least 95%) identical to SEQ ID NO:2 or SEQ ID NO:5, and (ii) a polynucleotide (polynucleotide sequence) encoding the protein (protein to be produced or protein of interest). For the avoidance of doubt, in such embodiments the polynucleotide (polynucleotide sequence) of (i) and the polynucleotide (polynucleotide sequence) of (ii) are present on a single (i.e. the same) nucleic acid molecule). Thus, the polynucleotide (polynucleotide sequence) of (i) and the polynucleotide (polynucleotide sequence) of (ii) can be considered to be fused. Such polynucleotides can be considered fusion polynucleotides or polynucleotides that encode fusion proteins.

Put another way, in some embodiments, the nucleic acid molecule encoding the protein (protein to be produced) additionally comprises a polynucleotide sequence of SEQ ID NO:2 or SEQ ID NO:5, or an amino acid sequence that is at least 70% (e.g. at least 75%, at least 80%, at least 85%, at least 90% or at least 95%) identical to SEQ ID NO:2 or SEQ ID NO:5.

In some embodiments, the nucleic acid molecule encoding the protein (protein to be produced) additionally comprises a fragment (or portion) of a polynucleotide sequence of SEQ ID NO:2 or a fragment (or portion) of a nucleotide sequence that is at least 70% (e.g. at least 75%, at least 80%, at least 85%, at least 90% or at least 95%) identical to SEQ ID NO:2. In some embodiments the fragment is at least 42 nucleotides in length, at least 45 nucleotides in length, at least 48 nucleotides in length, at least 51 nucleotides in length, at least 54 nucleotides in length, or at least 57 nucleotides in length. Preferably, the fragment has at least 70%, at least 75%, at least 80%, at least 85%, at least 90% or at least 95% sequence identity to SEQ ID NO:2.

In some embodiments, the nucleic acid molecule encoding the protein (protein to be produced) additionally comprises a fragment (or portion) of a polynucleotide sequence of SEQ ID NO:5 or a fragment (or portion) of a nucleotide sequence that is at least 70% (e.g. at least 75%, at least 80%, at least 85%, at least 90% or at least 95%) identical to SEQ ID NO:5. In some embodiments, the fragment is at least 42 nucleotides in length, at least 45 nucleotides in length, at least 48 nucleotides in length, at least 51 nucleotides in length, at least 54 nucleotides in length, at least 57 nucleotides in length, at least 60 nucleotides in length, at least 63 nucleotides in length, at least 66 nucleotides in length, at least 69 nucleotides in length or at least 72 nucleotides in length. Preferably, the fragment has at least 70%, at least 75%, at least 80%, at least 85%, at least 90% or at least 95% sequence identity to SEQ ID NO:5.

In some embodiments, the polynucleotide encoding the protein (protein to be produced) additionally comprises a polynucleotide sequence of SEQ ID NO:2.

In some embodiments, the polynucleotide encoding the protein (protein to be produced) additionally comprises a polynucleotide sequence of SEQ ID NO:5.

In embodiments in which in the nucleic acid molecule encoding the protein (protein to be produced) comprises (i) a polynucleotide comprising (or consisting of) a polynucleotide sequence of SEQ ID NO:2 or SEQ ID NO:5 or a sequence that is at least 70% (e.g. at least 75%, at least 80%, at least 85%, at least 90% or at least 95%) identical to SEQ ID NO:2 or SEQ ID NO:5, and (ii) a polynucleotide encoding a protein (protein to be produced or protein of interest, e.g. as defined elsewhere herein), the polynucleotide of (i) is preferably 5' to (i.e. positioned 5' to, e.g. immediately 5' to) the polynucleotide sequence encoding the protein. In some embodiments, the polynucleotide sequence based on SEQ ID NO:2 or SEQ ID NO:5 may be positioned immediately 5' to the polynucleotide encoding the protein (i.e. with no nucleotides between the SEQ ID NO:2 based sequence or SEQ ID NO:5 based sequence and the start of (the 5' end of) the polynucleotide sequence encoding the protein). In other embodiments, there may be one or more (e.g. 3-60, 3-20 or 3-15) nucleotides between the polynucleotide sequence based on SEQ ID NO:2 or based on SEQ ID NO:5 and the start of (the 5' end of) the polynucleotide encoding the protein. If there is stretch (or run or number) of nucleotides between the SEQ ID NO:2 based or SEQ ID NO:5 based polynucleotide and the polynucleotide encoding the protein, typically the number of nucleotides is divisible by three so that the fusion protein is expressed in-frame.

In preferred embodiments of methods and uses of the invention, the nucleic acid molecule does not encode a protein encoded by the Awod_I1781 gene of *Aliivibrio wodanis*. Thus, in some embodiments, the nucleic acid molecule does not encode a protein comprising the amino acid sequence of SEQ ID NO:48. In some embodiments, the nucleic acid molecule does not encode a protein comprising the amino acid sequence having an amino acid sequence that is at least 60% identical (or at least 70%, at least 80% or at least 90% identical) to the amino acid sequence of SEQ ID NO:48.

In some embodiments of methods and uses of the invention, the nucleic acid molecule does not encode a protein comprising the amino acid sequence of SEQ ID NO:49. In some embodiments, the nucleic acid molecule does not encode a protein comprising the amino acid sequence having an amino acid sequence that is at least 60% identical (or at least 70%, at least 80% or at least 90% identical) to the amino acid sequence of SEQ ID NO:49.

In preferred embodiments of methods and uses of the invention, a nucleic acid molecule in accordance with the present invention is not a naturally occurring nucleic acid molecule that comprises SEQ ID NO:2 or SEQ ID NO:5 (or that comprises a fragment or variant of SEQ ID NO:2 or SEQ ID NO:5 as described herein), i.e. is not a nucleic acid molecule that naturally comprises SEQ ID NO:2 or SEQ ID NO: 5 (or that naturally comprises a fragment or variant of SEQ ID NO:2 or SEQ ID NO:5 as described herein).

In preferred embodiments, nucleic acid molecules of the present invention are ≤100,000 nucleotides in length, ≤50,000 nucleotides in length, ≤20,000 nucleotides in length, ≤10,000 nucleotides in length, ≤9,000 nucleotides in length, ≤8,000 nucleotides in length, ≤7,000 nucleotides in length, ≤6,000 nucleotides in length or ≤5,000 nucleotides in length.

The person skilled in the art will be readily able to determine "conditions suitable for the expression of the encoded protein" in accordance with the methods of the present invention.

In some embodiments, the culturing of the *Aliivibrio wodanis* is done at a temperature of ≤20° C. (e.g. 0° C. to 20° C. or 4° C. to 20° C. or 12° C. to 20° C.). In some embodiments, the culturing of the *Aliivibrio wodanis* is done at a temperature ≤18° C. (e.g. 0° C. to 18° C. or 4° C. to 18° C. or 12° C. to 18° C.). In some embodiments, the culturing of the *Aliivibrio wodanis* is done at a temperature ≤15° C. (e.g. 0° C. to 15° C. or 4° C. to 15° C. or 12° C. to 15° C.). In some embodiments, the culturing of the *Aliivibrio wodanis* is done at a temperature ≤12° C. (e.g. 0° C. to 12° C. or 4° C. to 12° C.). In some embodiments, the culturing of the *Aliivibrio wodanis* is done at a temperature ≤10° C. (e.g. 0° C. to 10° C. or 4° C. to 10° C.). In some embodiments, the culturing of the *Aliivibrio wodanis* is done at a temperature ≤5° C. (e.g. 0° C. to 5° C.).

In some embodiments, the culturing of the *Aliivibrio wodanis* is done at a temperature of about 4° C. to about 18° C. (e.g. 4° C. to about 12° C. or 4° C. to about 16° C. or about 8° C. to about 16° C. or about 8° C. to about 18° C.).

In some preferred embodiments, the culturing of the *Aliivibrio wodanis* is done at a temperature of about 12° C. to about 18° C. (e.g. about 12° C. to about 17° C., or about 12° C. to about 16° C., or about 12° C. to about 15° C., or about 12° C. to about 14° C., or about 13° C. to about 18° C., or about 14° C. to about 18° C., or about 15° C. to about 18° C., or about 16° C. to about 18° C.).

In some preferred embodiments, the culturing of the *Aliivibrio wodanis* is done at a temperature of about 4° C., about 5° C., about 6° C., about 7° C., about 8° C., about 9° C., about 10° C., about 11° C., about 12° C., about 13° C., about 14° C., about 15° C., about 16° C., about 17° C. or about 18° C.

In some preferred embodiments, the culturing of the *Aliivibrio wodanis* is done at a temperature of about 12° C., about 13° C., about 14° C., about 15° C., about 16° C., about 17° C. or about 18° C.

In one preferred embodiment, the culturing of the *Aliivibrio wodanis* is done at a temperature of about 12° C.

In one preferred embodiment, the culturing of the *Aliivibrio wodanis* is done at a temperature of about 4° C.

Fluctuations from the preferred temperatures, or fluctuations outside of the preferred temperature ranges, may be tolerated, but for most of the culture period the temperature will be at the preferred temperature, or within preferred range endpoints.

Preferably a constant temperature is used for the culturing of the *Aliivibrio wodanis* and preferred temperatures are set out elsewhere herein. However, in some embodiments, the temperature may be varied during the culturing.

In embodiments of methods of the invention that further comprise a step prior to culturing the *Aliivibrio wodanis* of introducing a heterologous nucleic acid molecule encoding a protein and/or a further step subsequent to culturing the *Aliivibrio wodanis* of isolating (or obtaining or harvesting or purifying) the protein from the *Aliivibrio wodanis* host cell or from the growth medium or supernatant, these additional steps may be performed at a temperature that is different from (e.g. higher than) the temperature used for the culturing step. Alternatively, in some embodiments the entire method may be performed at the same temperature.

Any appropriate growth medium may be used for the culturing of *Aliivibrio wodanis* and the skilled person will be readily able to identify appropriate media. The medium may be a solid medium (e.g. an agar-based medium) or a liquid medium (e.g. a broth). For protein production in accordance with the present invention a liquid medium is typically preferred.

In some embodiments, the *Aliivibrio wodanis* cells are cultured in Lysogeny Broth (also referred to as LB) or in a medium that is equivalent thereto in terms of supporting the growth of *Aliivibrio wodanis*.

In some embodiments, the *Aliivibrio wodanis* cells are cultured in Lysogeny Broth supplemented with NaCl (e.g. 1%-5% NaCl, preferably 2.5% NaCl). In a preferred embodiment, the *Aliivibrio wodanis* cells are cultured in Lysogeny Broth supplemented with 2.5% NaCl.

For the avoidance of doubt, references herein to "supplemented with X % NaCl" or "+X % NaCl" or "with X % NaCl" are references to the total amount of NaCl added (w/v) to the medium (e.g. LB). A typical and preferred composition for 1 litre of LB supplemented with 2.5% NaCl is 10 g Peptone (e.g. from Fluka), 5 g yeast extract (e.g. from Merck), 25 g NaCl, 1000 ml $H_2O$ (preferably Milli-Q water). A typical and preferred composition for 1 litre of LB supplemented with 1% NaCl is 10 g Peptone (e.g. from Fluka), 5 g yeast extract (e.g. from Merck), 10 g NaCl, 1000 ml $H_2O$ (preferably Milli-Q water). For agar preparation, typically 15 g agar (e.g. from Fluka) is additionally included.

In some embodiments, the culturing may be done for between 1 and 14 days (e.g. 1-10 days, 2-10 days, 3-10 days, 1-6 days, 2-6 days, 3-6 days, 1-3 days or 2-3 days). In some embodiments, the culturing may be done for up to 1 day, up to 2 days, up to 3 days, up to 4 days, up to 5 days, up to 6 days, up to 7 days, up to 8 days, up to 9 days, up to 10 days, up to 11 days, up to 12 days, up to 13 days, up to 14 days, or longer.

In some embodiments, the culturing may be done for about 1 day, about 2 days, about 3 days, about 4 days, about 5 days, about 6 days, about 7 days, about 8 days, about 9 days, about 10 days, about 11 days, about 12 days, about 13 days or about 14 days. In some embodiments, the culturing may be done for about 1 day, about 2 days, about 3 days, about 4 days, about 5 days or about 6 days.

In some embodiments, the culturing may be done until the optical density (OD) of the culture reaches an $OD_{600\ nm}$, of at least 0.5, preferably at least 1, at least 2, at least 3, at least 4, at least 5, at least 6 or at least 7.

In some embodiments, the culture is a batch culture and in other embodiments the culture is a continuous culture.

The culturing of the bacterial strains of the invention in the production methods of the invention may take place in any suitable vessel (e.g. in culture flasks or in a bioreactor). In some embodiments a bioreactor (a system for the growth of cells in culture), preferably of industrial scale, may be used, preferably under the above described conditions. Suitable bioreactors are available in the art and the skilled person would find such reactors routine to use. Bioreactors may be specially designed to supply nutrients to a living culture of bacteria under optimum conditions and/or facilitate the removal of products produced by the bacteria, e.g. waste products that may inhibit growth. The bioreactor may be adapted to function in a batch-wise fashion or as a continuous culture, or both.

In some embodiments of methods of the invention, a step of isolating or obtaining or harvesting or purifying the protein from the *Aliivibrio wodanis* host cell, or from the growth medium/supernatant, is performed. Such methods may also comprise a step of purification (e.g. affinity purification) of the protein product. Such methods may also comprise a step of formulating the protein into a composition including at least one additional component, such as an acceptable buffer or carrier.

The protein (protein produced by a method of the invention) may be separated, or isolated, or harvested, or purified, from the *Aliivibrio wodanis* host cells or culture media using any of the purification techniques for protein known in the art and widely described in the literature, or any combination thereof. Such techniques may include for example, precipitation, ultrafiltration, dialysis, various chromatographic techniques, e.g. size exclusion chromatography, ion-exchange chromatography, affinity chromatography, electrophoresis, centrifugation etc. As discussed above, the proteins may be modified to carry amino acid motifs or other protein or non-protein tags, e.g. polyhistidine tags (e.g. $His_6$-tag), to assist in isolation, solubilisation and/or purification or identification.

In some embodiments, the *Aliivibrio wodanis* host cells are separated from the culture medium, e.g. by centrifugation, and then lysed (e.g. by the application of a lysis buffer). Any suitable lysis reagent (or lysis buffer) may be used. By way of example, a lysis buffer having the composition 50 mM Tris pH 8.0, 750 mM NaCl, and 5% (v/v) glycerol may be used. The lysis buffer may be supplemented with a protease inhibitor (or cocktail of protease inhibitors) and/or with DNase. In some embodiments, the cells may be disrupted by using a cell disruptor (e.g. after application of the lysis buffer). In some embodiments, the cell disruptor may be used at about 1.38 kbar, or at a setting that achieves substantially the same, the same, or at least the same, amount of cell disruption (lysis). Preferably, after cell lysis, the lysate is cleared by centrifugation (e.g. at 20,000×g for 30 mins at 4° C.).

In some embodiments, the protein is affinity purified (e.g. from a cleared lysate or supernatant). In some preferred embodiments, the protein carries a tag that facilitates purification, for example a His-tag (e.g. a $His_6$-tag) and purification may be done based on the tag by using an affinity reagent that binds to the tag. By way of example, if the protein has a His-tag, the protein may be affinity purified using immobilized metal affinity chromatography (I MAC). Such affinity purification methods are well-known in the art and suitable reagents equipment are commercially available (e.g. the HisTRAP HP column from GE Healthcare). Particularly preferred methods, and preferred reagents, for affinity purification are described in the Example section herein.

The terms "isolated" or "purified" used herein in connection with isolating or purifying a protein produced by a method of the invention refers to a protein substantially free of cellular material or other proteins from the source from which it is derived. In some embodiments, such isolated or purified proteins are substantially free of culture medium.

In one aspect, the present invention provides an *Aliivibrio wodanis* strain selected from the group consisting of:
 (i) the *Aliivibrio wodanis* strain deposited under accession number ECACC 18050101. This strain is also referred to herein as 01/09/401 (and 01/09/401 (11) or Vw11);
 (ii) the *Aliivibrio wodanis* strain deposited under accession number ECACC 18050102. This strain is also referred to herein as 03/09/160 (and 03/09/160 (37) or Vw37); and
 (iii) an *Aliivibrio wodanis* strain having all the identifying characteristics of one or both of strains (i) and (ii).

The ECACC is the European Collection of Authenticated Cell Cultures having its address at Public Health England, Culture Collections, Porton Down, Salisbury, Wiltshire SP4 0JG, United Kingdom. Each deposit was made with the ECACC under the Budapest Treaty on 1 May 2018 and confirmed as viable.

In a particularly preferred embodiment, the *Aliivibrio wodanis* is a strain of *Aliivibrio wodanis* strain selected from the group consisting of:
 (i) the *Aliivibrio wodanis* strain deposited under accession number ECACC 18050101; and
 (ii) the *Aliivibrio wodanis* strain deposited under accession number ECACC 18050102.

The bacterial strains are typically "isolated". By "isolated" it is meant that the bacterial strain is not in contact with the components of its natural environment, i.e. the environment from which it was originally taken. More specifically, an isolated strain of the invention is not in contact with environment from which it was taken and/or is not in contact with other microbes, e.g. bacteria, from the environment from which it was taken. Most populations of the bacterial strains of the invention will have been produced by means of a technical process, e.g. cultured, and not themselves taken from a natural environment, these are inherently "isolated" in the sense of being free from any natural environment or state.

Thus, the invention also provides a biologically pure culture of a bacterial strain of the invention. A biologically pure culture may be considered as being substantially, preferably essentially, and most preferably completely, free of other intact cells, microbial or otherwise. Numerically this may be expressed as a culture in which at least 90%, preferably at least 95%, 98%, 99% or 99.5%, of the cells present therein are those of a selected bacterial strain of the invention. The above isolated strains will preferably be biologically pure cultures.

In another aspect, the present invention provides a fusion protein comprising (or consisting of) (i) a fusion moiety (or tag) comprising (or consisting of) an amino acid sequence of SEQ ID NO:1 or an amino acid sequence that is at least 70% (e.g. at least 75%, at least 80%, at least 85%, at least 90% or at least 95%) identical to SEQ ID NO:1, and (ii) a protein. The protein of (ii) is the protein of interest, such as an enzyme.

In a preferred embodiment, the fusion protein comprises (or consists of) (i) a fusion moiety (or tag) consisting of an amino acid sequence of SEQ ID NO:1 and (ii) a protein.

In preferred embodiments of the fusion proteins of the invention, the fusion moiety (or tag) is provided (or positioned or fused) as an N-terminal tag (i.e. is present or fused at the N-terminus of the protein, optionally via an amino acid linker such as a 1-20, 1-10 or 1-5 amino acid linker).

Thus, in preferred embodiments, the fusion protein comprises (or consists of) (i) a fusion moiety (or tag) comprising (or consisting of) an amino acid sequence of SEQ ID NO:1 or an amino acid sequence that is at least 70% (e.g. at least 75%, at least 80%, at least 85%, at least 90% or at least 95%) identical to SEQ ID NO:1, and (ii) a protein, wherein the fusion moiety of (i) is positioned at the N-terminus of the fusion protein (i.e. is an N-terminal fusion moiety or N-terminal tag). The protein of (ii) is the protein of interest, such as an enzyme.

In one preferred embodiment, the fusion protein comprises (i) a N-terminal fusion moiety (or tag) consisting of an amino acid sequence of SEQ ID NO:1 and (ii) an Exonuclease I such as an Exonuclease I *Moritella viscosa* (MvExoI) or from *Aliivibrio salmonicida* (AsExoI).

In one preferred embodiment, the fusion protein comprises (or consists of) (i) a N-terminal fusion moiety (or tag) consisting of an amino acid sequence of SEQ ID NO:1 and (ii) a DNA polymerase such as a DNA polymerase II from *Aliivibrio salmonicida* (AsPolII).

In one preferred embodiment, the fusion protein comprises (or consists of) (i) a N-terminal fusion moiety (or tag) consisting of an amino acid sequence of SEQ ID NO:1 and (ii) a ligase such as a ligase (e.g. ligase 1) from *Cenarchaeum symbiosum* (CsLig1) or a ligase (e.g. ligase 6) from *Colwellia psychrerythraea* (CpLig6).

In one preferred embodiment, the fusion protein comprises (or consists of) (i) a N-terminal fusion moiety (or tag) consisting of an amino acid sequence of SEQ ID NO:1 and (ii) an alcohol dehydrogenase from *Streptomyces* (AdhStrep).

In some embodiments of fusion proteins of the invention, a fusion moiety comprising (or consisting of) an amino acid sequence of SEQ ID NO:1, or an amino acid sequence that is at least 70% identical to SEQ ID NO:1, further comprises at its C-terminal end an amino acid sequence comprising (or consisting of) GNAFA (SEQ ID NO:51) or comprising (or consisting of) an amino acid sequence having 1, 2 or 3 (preferably 1 or 2, more preferably 1) amino acid insertions, deletions or substitutions as compared to the amino acid sequence GNAFA (SEQ ID NO:51). In some embodiments, a fusion moiety comprising (or consisting of) an amino acid sequence of SEQ ID NO:1, or an amino acid sequence that is at least 70% identical to SEQ ID NO:1, further comprises at its C-terminal end an amino acid sequence comprising (or consisting of) GNAFA (SEQ ID NO:51).

A particularly preferred fusion moiety comprising the amino acid sequence of SEQ ID NO:1 is a fusion moiety comprising (or consisting of) the amino acid sequence of SEQ ID NO:4 (MSKQMKFGLLPAAIAGALLSGNAFA).

Thus, in another aspect, the present invention provides a fusion protein comprising (or consisting of) (i) a fusion moiety (or tag) comprising (or consisting of) an amino acid sequence of SEQ ID NO:4 or an amino acid sequence that is at least 70% (e.g. at least 75%, at least 80%, at least 85%, at least 90% or at least 95%) identical to SEQ ID NO:4, and (ii) a protein. The protein of (ii) is the protein of interest, such as an enzyme.

In a preferred embodiment, the fusion protein comprises (or consists of) (i) a fusion moiety (or tag) consisting of an amino acid sequence of SEQ ID NO:4 and (ii) a protein.

In preferred embodiments, the fusion protein comprises (or consists of) (i) a fusion moiety (or tag) comprising (or consisting of) an amino acid sequence of SEQ ID NO:4 or an amino acid sequence that is at least 70% (e.g. at least 75%, at least 80%, at least 85%, at least 90% or at least 95%) identical to SEQ ID NO:4, and (ii) a protein, wherein the fusion moiety of (i) is positioned at the N-terminus of the fusion protein (i.e. is an N-terminal fusion moiety or N-terminal tag). The protein of (ii) is the protein of interest, such as an enzyme.

The discussion elsewhere herein in connection with fusion proteins comprising SEQ ID NO:1-related fusion moieties, e.g. of preferred features, may be applied *mutatis mutandis* to aspects and embodiments of the invention that relate to fusion proteins comprising SEQ ID NO:4-related fusion moieties.

In some embodiments, fusion moieties comprising (or consisting of) an amino acid sequence that is at least 70% (e.g. at least 75%, at least 80%, at least 85%, at least 90% or at least 95%) identical to SEQ ID NO:4 (or fragments thereof) have no more than 3 (preferably 1 or 2, more preferably 1, and most preferably no) amino acid insertions, deletions or substitutions in the GNAFA (SEQ ID NO:51) amino acid motif of SEQ ID NO:4.

In some embodiments, a fusion protein of the invention may comprise a fusion moiety that comprises (or consists of) a fragment (or portion) of an amino acid sequence of SEQ ID NO:1 or a fragment (or portion) of an amino acid sequence that is at least 70% (e.g. at least 75%, at least 80%, at least 85%, at least 90% or at least 95%) identical to SEQ ID NO:1. In some embodiments, the fragment is at least 14 amino acids in length or at least 15 amino acids in length, preferably at least 16 amino acids in length or at least 17 amino acids in length, more preferably at least 18 amino acids in length or at least 19 amino acids in length. Preferably, the fragment has at least 70%, at least 75%, at least 80%, at least 85%, at least 90% or at least 95% sequence identity to SEQ ID NO:1. Suitable fragments are also discussed elsewhere herein.

In some embodiments, a fusion protein of the invention may comprise a fusion moiety that comprises (or consists of) a fragment (or portion) of an amino acid sequence of SEQ ID NO:4 or a fragment (or portion) of an amino acid sequence that is at least 70% (e.g. at least 75%, at least 80%, at least 85%, at least 90% or at least 95%) identical to SEQ ID NO:4. In some embodiments, the fragment is at least 14 amino acids in length or at least 15 amino acids in length, preferably at least 16 amino acids in length or at least 17 amino acids in length or at least 18 amino acids in length or at least 19 amino acids in length, more preferably at least 20 amino acids in length, at least 21 amino acids in length, at least 22 amino acids in length, at least 23 amino acids in length or at least 24 amino acids in length. Preferably, the fragment has at least 70%, at least 75%, at least 80%, at least 85%, at least 90% or at least 95% sequence identity to SEQ ID NO:4. Suitable fragments are also discussed elsewhere herein.

The fusion protein of the present invention is not a protein encoded by the Awod_I1781 gene of *Aliivibrio wodanis*. Thus, the fusion protein of the present invention is not a protein comprising (or consisting of) the amino acid sequence of SEQ ID NO:48. In some embodiments, the fusion protein is not a protein comprising (or consisting of) an amino acid sequence that is at least 60% identical (or at least 70%, at least 80% or at least 90% identical) to the amino acid sequence of SEQ ID NO:48.

The fusion protein of the present invention is not a protein comprising (or consisting of) the amino acid sequence of SEQ ID NO:49. In some embodiments, the fusion protein of the present invention is not a protein comprising (or consisting of) an amino acid sequence that is at least 60% identical (or at least 70%, at least 80% or at least 90% identical) to the amino acid sequence of SEQ ID NO:49.

A fusion protein in accordance with the present invention is not a naturally occurring protein that comprises SEQ ID NO:1 or SEQ ID NO:4, i.e. is not a protein that naturally comprises SEQ ID NO:1 or SEQ ID NO:4. Preferably, a fusion protein in accordance with the present invention is not a naturally occurring protein that comprises a fragment or variant of SEQ ID NO:1 or SEQ ID NO:4 as described herein, i.e. is not a protein that naturally comprises a fragment or variant of SEQ ID NO:1 or SEQ ID NO:4 as described herein.

In some embodiments, fusion proteins in accordance with the present invention do not comprise the amino acid motif GTEACIE (SEQ ID NO:50).

In some embodiments, fusion proteins of the invention may be isolated fusion proteins.

Typically and preferably, fusion proteins that comprise (or consist of) a fusion moiety that comprises (or consists of) a fragment or a variant of SEQ ID NO:1 or SEQ ID NO:4 as described herein are capable of being expressed in, and/or secreted from, a host cell in which they are expressed to a level that is at least substantially equivalent to (or equivalent to or at least (substantially) the same as) the level of expression or secretion attained (or observed) when the fusion moiety comprises (or consists of) SEQ ID NO:1 or SEQ ID NO:4 (i.e. SEQ ID NO:1 itself or SEQ ID NO:4 itself).

SEQ ID NO:1-based fusion proteins and SEQ ID NO:4-based fusion proteins are also discussed elsewhere herein in the context of the methods of the invention and that discussion, e.g. of preferred features, may be applied *mutatis mutandis* to the aspect of the invention directed to the fusion protein products themselves.

In another aspect, the present invention provides a nucleic acid molecule encoding a fusion protein of the invention. Thus, the present invention provides a nucleic acid molecule comprising (or consisting of) (i) a polynucleotide comprising (or consisting of) a polynucleotide sequence of SEQ ID NO:2 or a polynucleotide sequence that is at least 70% (e.g. at least 75%, at least 80%, at least 85%, at least 90% or at least 95%) identical to SEQ ID NO:2, and (ii) a polynucleotide sequence encoding a protein. The protein of (ii) is the protein of interest, such as an enzyme.

In a preferred embodiment, the nucleic acid molecule comprises (or consists of) (i) a polynucleotide consisting of a polynucleotide sequence of SEQ ID NO:2 and (ii) a polynucleotide sequence encoding a protein.

In preferred embodiments in which in the nucleic acid molecule encoding the protein (protein to be produced) comprises (i) a polynucleotide comprising (or consisting of) a polynucleotide sequence of SEQ ID NO:2 or a sequence that is at least 70% (e.g. at least 75%, at least 80%, at least 85%, at least 90% or at least 95%) identical to SEQ ID NO:2, and (ii) a polynucleotide sequence encoding a protein, the polynucleotide of (i) is 5' to (i.e. positioned 5' to, e.g. immediately 5' to) the polynucleotide sequence encoding the protein.

A particularly preferred polynucleotide comprising (or consisting of) a polynucleotide sequence of SEQ ID NO:2 comprises (or consists of) the polynucleotide sequence of SEQ ID NO:5.

Thus, in another aspect, the present invention provides a nucleic acid molecule comprising (or consisting of) (i) a polynucleotide comprising (or consisting of) a polynucleotide sequence of SEQ ID NO:5 or a polynucleotide sequence that is at least 70% (e.g. at least 75%, at least 80%, at least 85%, at least 90% or at least 95%) identical to SEQ ID NO:5, and (ii) a polynucleotide sequence encoding a protein. The protein of (ii) is the protein of interest, such as an enzyme.

In a preferred embodiment, the nucleic acid molecule comprises (or consists of (i) a polynucleotide consisting of a polynucleotide sequence of SEQ ID NO:5 and (ii) a polynucleotide sequence encoding a protein.

In preferred embodiments in which in the nucleic acid molecule encoding the protein (protein to be produced) comprises (i) a polynucleotide comprising (or consisting of) a polynucleotide sequence of SEQ ID NO:5 or a sequence that is at least 70% (e.g. at least 75%, at least 80%, at least 85%, at least 90% or at least 95%) identical to SEQ ID NO:2, and (ii) a polynucleotide sequence encoding a protein, the polynucleotide of (i) is 5' to (i.e. positioned 5' to, e.g. immediately 5' to) the polynucleotide sequence encoding the protein.

The discussion elsewhere herein in connection with nucleic acids comprising SEQ ID NO:2-related polynucleotides, e.g. of preferred features, may be applied *mutatis mutandis* to aspects and embodiments of the invention that relate to nucleic acid molecules comprising SEQ ID NO:5-related polynucleotides.

In another embodiment, a nucleic acid molecule of the invention may comprise (or consist of) (i) a polynucleotide comprising (or consisting of) a fragment (or portion) of a polynucleotide sequence of SEQ ID NO:2 or a fragment (or portion) of a polynucleotide sequence that is at least 70% (e.g. at least 75%, at least 80%, at least 85%, at least 90% or at least 95%) identical to SEQ ID NO:2, and (ii) a polynucleotide sequence encoding a protein. The protein of (ii) is the protein of interest, such as an enzyme. In some embodiments the fragment is at least 42 nucleotides in length, at least 45 nucleotides in length, at least 48 nucleotides in length, at least 51 nucleotides in length, at least 54 nucleotides in length or at least 57 nucleotides in length. Preferably, the fragment has at least 70%, at least 75%, at least 80%, at least 85%, at least 90% or at least 95% sequence identity to SEQ ID NO:2. Suitable fragments are also discussed elsewhere herein.

In another embodiment, a nucleic acid molecule of the invention may comprise (or consist of) (i) a polynucleotide comprising (or consisting of) a fragment (or portion) of a polynucleotide sequence of SEQ ID NO:5 or a fragment (or portion) of a polynucleotide sequence that is at least 70% (e.g. at least 75%, at least 80%, at least 85%, at least 90% or at least 95%) identical to SEQ ID NO:5, and (ii) a polynucleotide sequence encoding a protein. The protein of (ii) is the protein of interest, such as an enzyme. In some embodiments the fragment is at least 42 nucleotides in length, at least 45 nucleotides in length, at least 48 nucleotides in length, at least 51 nucleotides in length, at least 54 nucleotides in length, at least 57 nucleotides in length, at least 60 nucleotides in length, at least 63 nucleotides in length, at least 66 nucleotides in length at least 69 nucleotides in length or at least 72 nucleotides in length. Preferably, the fragment has at least 70%, at least 75%, at least 80%, at least 85%, at least 90% or at least 95% sequence identity to SEQ ID NO:2. Suitable fragments are also discussed elsewhere herein.

The nucleic acid molecule of the invention does not encode a protein encoded by the Awod_I1781 gene of *Aliivibrio wodanis*. Thus, the nucleic acid molecule of the present invention does not encode a protein comprising (or consisting of) the amino acid sequence of SEQ ID NO:48. In some embodiments, the nucleic acid molecule does not encode a protein comprising (or consisting of) an amino acid sequence that is at least 60% identical (or at least 70%, 80% or 90% identical) to the amino acid sequence of SEQ ID NO:48.

The nucleic acid molecule of the present invention does not encode a protein comprising (or consisting of) the amino acid sequence of SEQ ID NO:49. In some embodiments, the fusion protein of the present invention is not a protein comprising (or consisting of) an amino acid sequence that is at least 60% identical (or at least 70%, 80% or 90% identical) to the amino acid sequence of SEQ ID NO:49.

A nucleic acid molecule in accordance with the present invention is not a naturally occurring nucleic acid molecule that comprises SEQ ID NO:2 or SEQ ID NO:5, i.e. is not a nucleic acid molecule that naturally comprises SEQ ID NO:2 or SEQ ID NO:5. Preferably, a nucleic acid molecule in accordance with the present invention is not a naturally occurring nucleic acid molecule that comprises a fragment or variant of SEQ ID NO:2 or SEQ ID NO:5 as described herein, i.e. is not a nucleic acid molecule that naturally comprises a fragment or variant of SEQ ID NO:2 or SEQ ID NO:5 as described herein.

In some embodiments, nucleic acid molecules of the present invention are ≤100,000 nucleotides in length, ≤50,000 nucleotides in length, ≤20,000 nucleotides in length, ≤10,000 nucleotides in length, ≤9,000 nucleotides in length, ≤8,000 nucleotides in length, ≤7,000 nucleotides in length, ≤6,000 nucleotides in length or ≤5,000 nucleotides in length.

In another aspect, the present invention provides an expression vector, e.g. a plasmid) which comprises a polynucleotide sequence of SEQ ID NO:2 or SEQ ID NO:5, or a polynucleotide sequence that is at least 70% (e.g. at least 75%, at least 80%, at least 85%, at least 90% or at least 95%) identical to SEQ ID NO:2 or SEQ ID NO:5. In some embodiments, the expression vector is configured such that a polynucleotide sequence encoding a protein (e.g. enzyme) of interest can be inserted (or cloned) downstream (i.e. at the 3'-end) of the polynucleotide sequence of SEQ ID NO:2 or SEQ ID NO:5 (or SEQ ID NO:2 related sequence or SEQ ID NO:5 related sequence). Such expression vectors may thus encode fusion proteins of the invention.

In some embodiments, nucleic acid molecules and expression vectors of the invention may be isolated nucleic acid molecules and expression vectors.

Nucleic acid molecules comprising SEQ ID NO:2 or SEQ ID NO:5 (or related sequences) are discussed elsewhere herein in the context of the methods of the invention and that discussion, e.g. of preferred features, may be applied *mutatis mutandis* to the aspect of the invention directed to the nucleic acid molecule products themselves and related expression vector products.

In another aspect, the present invention provides an expression vector (e.g. a plasmid) that comprises a promoter that comprises (or consists of) a polynucleotide of SEQ ID NO:3 or a sequence having at least 70% (e.g. at least 75%, at least 80%, at least 85%, at least 90% or at least 95%) sequence identity to SEQ ID NO:3. In some embodiments, a protein of interest is also encoded by said expression vector, preferably a polynucleotide encoding said protein of interest is positioned downstream (3' to) said SEQ ID NO:3-based promoter such that expression of the protein of interest is under the control of (or driven by) said promoter.

The proteins (e.g. fusion proteins) and nucleic acid molecules of the invention may be "isolated" or "purified". The term "isolated" or "purified" typically refers to a protein or nucleic acid that is substantially free of cellular material or other proteins (or other nucleic acids) from the source from which it is derived or produced. In some embodiments, such isolated or purified proteins or nucleic acid molecules are substantially free of culture medium when produced by recombinant techniques, or chemical precursors or other chemicals when chemically synthesized.

In another aspect, the present invention provides a composition comprising (i) a fusion protein of the invention or a nucleic acid molecule of the invention or an expression vector of the invention and (ii) a buffer, carrier or diluent. Typically such compositions are cell-free (or substantially cell-free) compositions. Compositions of the invention may be suitable for biotechnological and/or industrial applications. Suitable buffers, carriers and diluents for proteins and nucleic acids are well-known to a person skilled in the art.

In another aspect, the present invention provides the use of *Aliivibrio wodanis* as host microorganism for the production of a protein. The discussion above in connection with other aspects of the invention may be applied, *mutatis mutandis*, to this aspect of the invention.

In another aspect, the present invention provides a method for increasing the expression level of a protein in an *Aliivibrio wodanis* host cell (or increasing the level to which a protein is expressed when expressed in a host cell or increasing the level to which a protein is capable of being expressed in a host cell), said method comprising incorporating into said protein (preferably at the N-terminus) a fusion moiety comprising (or consisting of) an amino acid sequence of SEQ ID NO:1 or SEQ ID NO:4 or an amino acid sequence that is at least 70% (e.g. at least 75%, at least 80%, at least 85%, at least 90% or at least 95%) identical to SEQ ID NO:1 or SEQ ID NO:4. The increase in expression may be an increase of at least 10%, at least 20%, at least 30%, at least 40%, at least 50%, at least 60%, at least 70%, at least 80%, at least 90%, at least 100%, at least 200%, at least 300%, at least 400%, at least 500% or at least 1000% (e.g. up to 500% increase, or up to 1000% increase or up to 2000% increase) in comparison with the same protein that lacks the fusion moiety. The discussion above in connection with other aspects of the invention may be applied, *mutatis mutandis*, to this aspect of the invention.

In another aspect the present invention provides the use of a fusion moiety comprising (or consisting of) an amino acid sequence of SEQ ID NO:1 or SEQ ID NO:4 or an amino acid sequence that is at least 70% (e.g. at least 75%, at least 80%, at least 85%, at least 90% or at least 95%) identical to SEQ ID NO:1 or SEQ ID NO:4 in the preparation (or production) of a protein (e.g. enzyme) in an *Aliivibrio wodanis* host cell, wherein said fusion moiety is fused (preferably N-terminally fused) to the protein. Preferably, the use of the fusion moiety increases the expression of the protein in the host cell in comparison to when the fusion moiety is not used (not present). The increase in expression may be an increase of at least 10%, at least 20%, at least 30%, at least 40%, at least 50%, at least 60%, at least 70%, at least 80%, at least 90%, at least 100%, at least 200%, at least 300%, at least 400%, at least 500% or at least 1000% (e.g. up to 500% increase, or up to 1000% increase or up to 2000% increase) in comparison to when the fusion moiety is not used (not present).

In another aspect the invention provides a kit comprising one or more of the *Aliivibrio wodanis* strains the invention, and/or one or more of fusion proteins of the invention, and/or one or more of the nucleic acid molecules of the invention, and/or one or more of the expression vectors of the invention. Preferably said kits are for use in the methods and uses as described herein, e.g., for protein production. Preferably said kits comprise instructions for use of the kit components.

As described in the Example section herein, the present inventors have also found that, advantageously, "difficult to express" proteins (e.g. enzymes), such as proteins that are typically difficult to express in mesophilic organisms (e.g. *E. coli*), can be satisfactorily expressed in mesophiles (e.g. in *E. coli*) if the protein is provided with a fusion moiety based on SEQ ID NO:1.

Thus, in another aspect, the present invention provides a method of producing a protein, said method comprising culturing a host cell comprising a heterologous nucleic acid molecule encoding said protein under conditions suitable for the expression of the encoded protein, wherein said protein is a fusion protein comprising (or consisting of) (i) a fusion moiety (or tag) comprising (or consisting of) an amino acid sequence of SEQ ID NO:1 or SEQ ID NO:4 (or fragment thereof) or an amino acid sequence that is at least 70% (e.g. at least 75%, at least 80%, at least 85%, at least 90% or at least 95%) identical to SEQ ID NO:1 or SEQ ID NO:4 (or fragment thereof), and (ii) a protein (protein to be produced or protein of interest). Other features and properties of other aspects of the invention apply, *mutatis mutandis*, to this aspect of the invention. For example, exemplary and preferred fusion proteins are discussed elsewhere herein in connection with other aspects of the invention and these apply, *mutatis mutandis*, to this aspect of the invention. For example, preferably, the fusion moiety of (i) is positioned N-terminally relative to the protein of (ii), e.g. as described elsewhere herein. Exemplary and preferred nucleic acids and expression vectors are discussed elsewhere herein in connection with other aspects of the invention and these apply, *mutatis mutandis*, to this aspect of the invention.

In accordance with this aspect of the invention, the host cell is typically a microorganism, preferably a bacterial host cell. In some embodiments, the host cell is of the genus *Aliivibrio* (e.g. is *A. wodanis*). In some embodiments, the host cell is not of the genus *Aliivibrio*. In some embodiments, the host cell is a non-*Aliivibrio* bacterial host cell. In some embodiments the host cell is a mesophilic host cell, preferably a mesophilic bacterial host cell, more preferably *E. coli* (e.g. *E. coli* DH5αλpir).

In some embodiments, the host cell (e.g. *E. coli*) may be cultured at its optimum growth temperature (e.g. about 37° C. in the case of *E. coli*). In some embodiments, the host cell (e.g. *E. coli*) may be cultured at a temperature that is lower than its optimum growth temperature (e.g. ≤35° C., ≤30° C., ≤25° C., ≤20° C., or ≤15° C., preferably at about 15° C., in the case of *E. coli*). In some embodiments, the host cell (e.g. *E. coli*) may be cultured initially at its optimum growth temperature (e.g. about 37° C. in the case of *E. coli*), for example until an $OD_{600\ nm}$ of about 0.7-1.0 is reached, and subsequently cultured at a lower temperature (e.g. ≤35° C., ≤30° C., ≤25° C., ≤20° C., or ≤15° C., preferably at about 15° C., in the case of *E. coli*), for example for 1-20, 1-10, 1-8, 5-20, 5-10, 5-8, 10-15 or 15-20 hours. Without wishing be bound by theory, culture at a lower the optimum temperature may be advantageous for the expression of "difficult to express" proteins. A particularly preferred method for producing a protein in a mesophilic host cell (e.g. in *E. coli*) is described in the Example section herein.

In another aspect, the present invention provides a method for increasing the expression level of a protein in a host cell (or increasing the level to which a protein is expressed when expressed in a host cell or increasing the level to which a protein is capable of being expressed in a host cell), said method comprising incorporating into said protein (preferably at the N-terminus) a fusion moiety comprising (or consisting of) an amino acid sequence of SEQ ID NO:1 or SEQ ID NO:4 (or fragment thereof) or an amino acid sequence that is at least 70% (e.g. at least 75%, at least 80%, at least 85%, at least 90% or at least 95%) identical to SEQ ID NO:1 or SEQ ID NO:4 (or fragment thereof). The increase in expression may be an increase of at least 10%, at least 20%, at least 30%, at least 40%, at least 50%, at least 60%, at least 70%, at least 80%, at least 90%, at least 100%, at least 200%, at least 300%, at least 400%, at least 500% or at least 1000% (e.g. up to 500% increase, or up to 1000% increase or up to 2000% increase) in comparison with the same protein that lacks the fusion moiety. The discussion above in connection with other aspects of the invention may be applied, *mutatis mutandis*, to this aspect of the invention. For example, the host cell may be of the genus *Aliivibrio* or may be a non-*Aliivibrio* host cell (e.g. a mesophilic bacterial host cell) as described elsewhere herein.

In another aspect, the present invention provides the use of a fusion moiety comprising (or consisting of) an amino acid sequence of SEQ ID NO:1 or SEQ ID NO:4 (or a fragment thereof) or an amino acid sequence that is at least 70% (e.g. at least 75%, at least 80%, at least 85%, at least 90% or at least 95%) identical to SEQ ID NO:1 or SEQ ID NO:4 (or a fragment thereof) in the preparation (or production) of a protein (e.g. enzyme) in a host cell, wherein said fusion moiety is fused (preferably N-terminally fused) to the protein. Preferably, the use of the fusion moiety increases the expression of the protein in the host cell in comparison to when the fusion moiety is not used (not present). Put another way, preferably the use of the fusion moiety increases level to which a protein is expressed when expressed in a host cell or increases the level to which a protein is capable of being expressed in a host cell. The increase in expression may be an increase of at least 10%, at least 20%, at least 30%, at least 40%, at least 50%, at least 60%, at least 70%, at least 80%, at least 90%, at least 100%, at least 200%, at least 300%, at least 400%, at least 500% or at least 1000% (e.g. up to 500% increase, or up to 1000% increase or up to 2000% increase) in comparison to when the fusion moiety is not used (not present). The discussion above in connection with other aspects of the invention may be applied, *mutatis mutandis*, to this aspect of the invention. For example, the host cell may be of the genus *Aliivibrio* or may be a non-*Aliivibrio* host cell (e.g. a mesophilic bacterial host cell) as described elsewhere herein.

In another aspect, the present invention provides a method for increasing the level of secretion of a protein from a host cell (or increasing the ability of a protein to be secreted from a host cell), said method comprising incorporating into said protein (preferably at the N-terminus) a fusion moiety comprising (or consisting of) an amino acid sequence of SEQ ID NO:1 or SEQ ID NO:4 (or fragment thereof) or an amino acid sequence that is at least 70% (e.g. at least 75%, at least 80%, at least 85%, at least 90% or at least 95%) identical to SEQ ID NO:1 or SEQ ID NO:4 (or fragment thereof). The increase in secretion may be an increase of at least 10%, at least 20%, at least 30%, at least 40%, at least 50%, at least 60%, at least 70%, at least 80%, at least 90%, at least 100%, at least 200% or at least 300% (e.g. up to 50% or up to 100% or up to 200% or up to 300% or up to 500%), in comparison with the same protein that lacks the fusion moiety. The discussion above in connection with other aspects of the invention may be applied, *mutatis mutandis*, to this aspect of the invention. For example, the host cell may be of the genus *Aliivibrio* or may be a non-*Aliivibrio* host cell (e.g. a mesophilic bacterial host cell) as described elsewhere herein.

Where the terms "comprise", "comprises", "comprising", "has" or "having", or other equivalent terms are used herein, then in some more specific embodiments these terms include the term "consists of" or "consists essentially of", or other equivalent terms.

The invention will now be further described in the following non-limiting Examples with reference to the following drawings:

FIG. 1. Selection of *A. wodanis* strains. A. Growth curve for *A. wodanis* strain 03/09/160 at 4° C. and 12° C. Similar growth pattern was observed for all 12 tested strains. Error bars represent standard deviation between three replicates. B. Conjugation efficiency for twelve *A. wodanis* strains. Bars show uptake of pTM214 vector. Plus signs (+) indicate integration of pNQ705 vector into chromosome. C. Expression of RFP in *A. wodanis* 03/09/160 containing pVSV208. Bars indicate measured relative fluorescence. RFU=relative fluorescence units.

Figure 2:
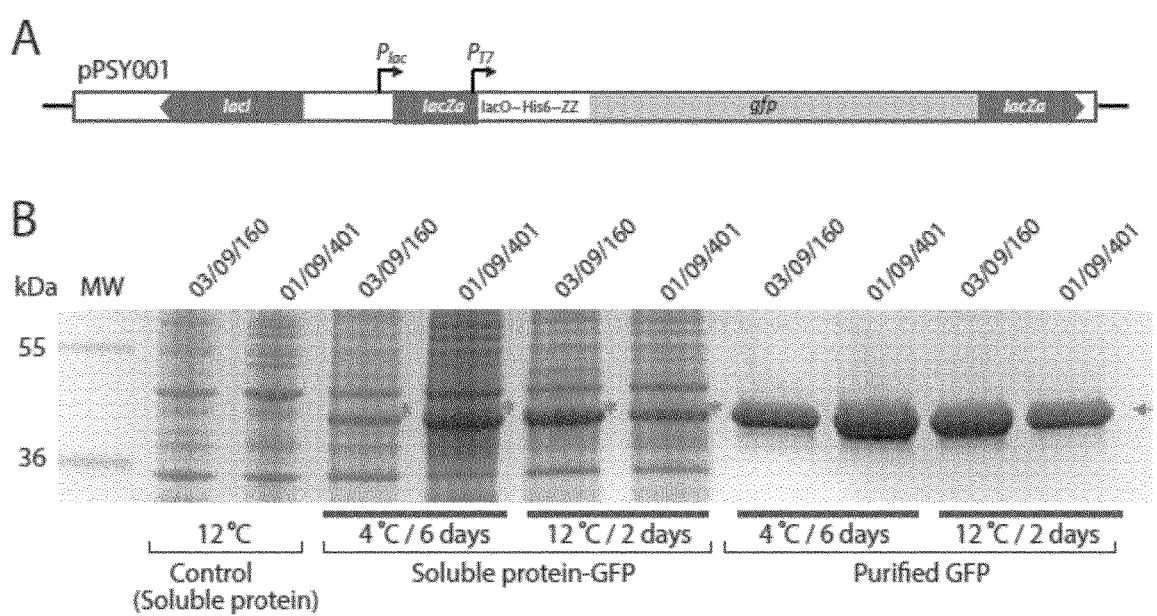

FIG. 2. Expression of GFP in *A. wodanis* strains 01/09/401 and 03/09/160. A. Schematic drawing showing the expression cassette in pPSY001. The promoter and His-ZZ-GFP originates from pETZZ1a and the plasmid backbone is from pVSV105. B. Coomassie-stained SDS polyacrylamide gel showing expressed GFP. MW=Molecular weight marker. Control samples (soluble protein fraction) are from *A. wodanis* with no plasmid. The molecular weight of GFP is 26.9 kDa. In the figure GFP migrates as a higher molecular weight molecule (approx. 44 kDa) due to the presence of the His-ZZ-tag. Arrow is pointing to the expected size of GFP (44 kDa), and asterisks indicate protein bands verified by mass spectrometry as GFP in soluble protein fraction.

Figure 3:
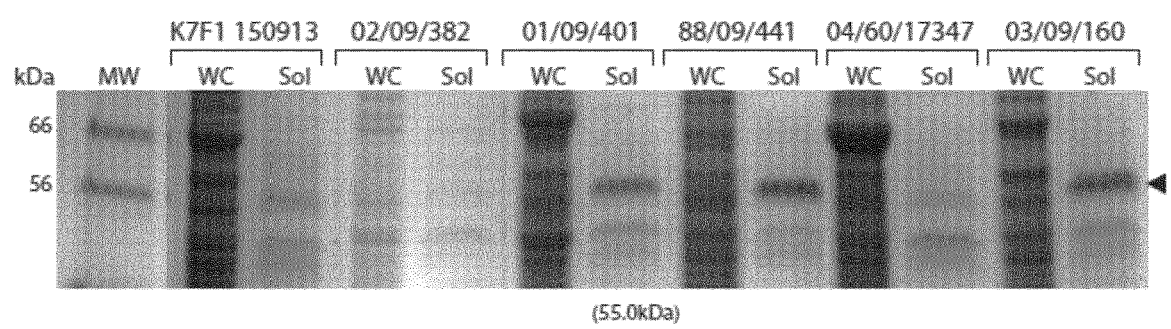

FIG. 3. Expression of Exonuclease I from *A. salmonicida* (AsExoI). Expression of AsExoI was compared using six *A. wodanis* strains. Arrowhead denotes bands with molecular weight (55.0 kDa) corresponding to AsExoI (verified by mass spectrometry). WC=whole cell, Sol=soluble protein fraction, MW=molecular weight marker.

Figure 4:
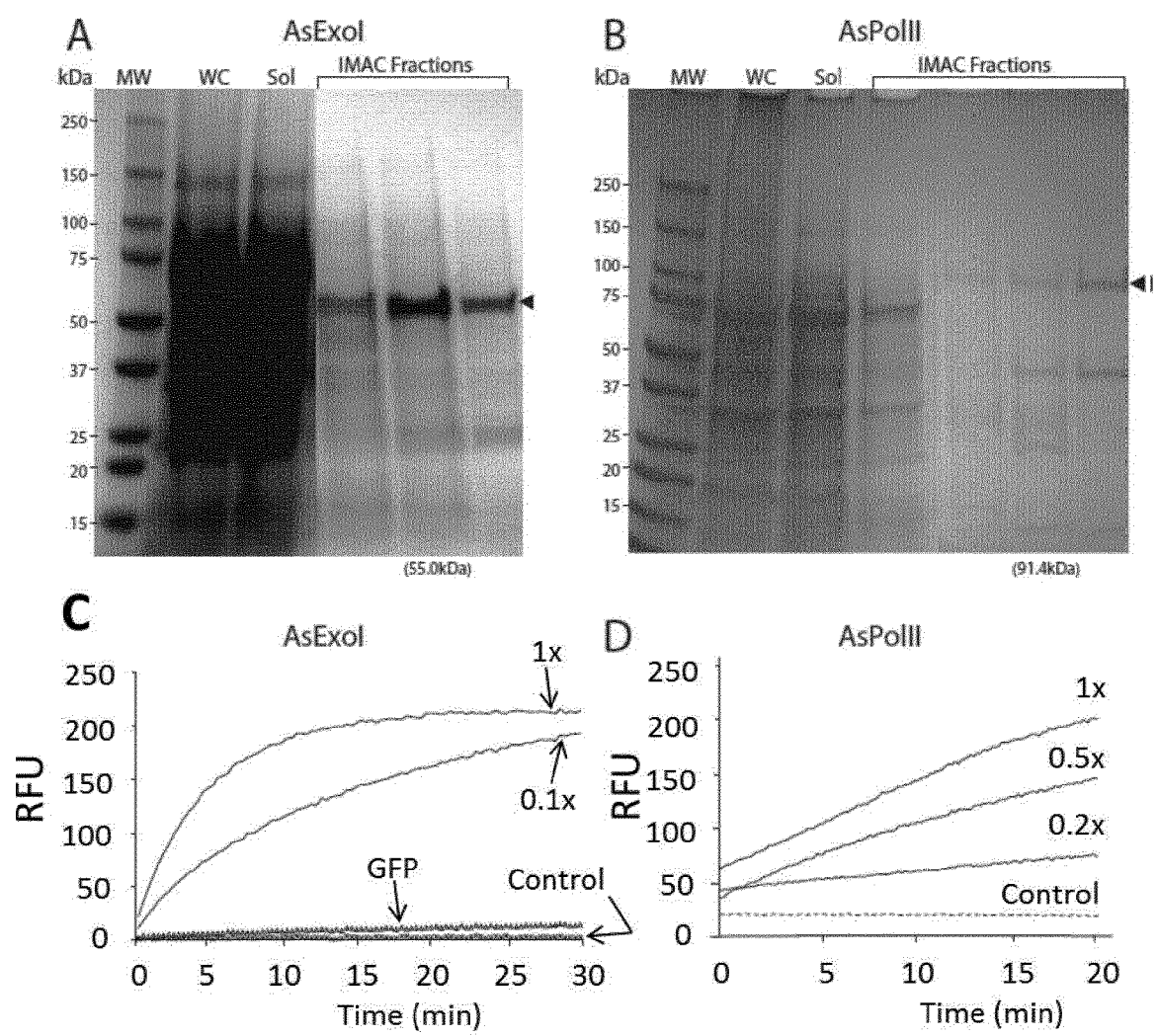

FIG. 4. Expression, purification and activity of AsExoI and AsPolIII. Coomassie-stained SDS acrylamide gels showing expressed and affinity purified 6×His-AsExoI (A) and 6×His-AsPolIII (B). MW=molecular weight marker (Biorad protein standard), WC=whole cell extract, Sol=lysate soluble protein fraction. Immobilized metal affinity chromatography (IMAC) was done to purify 6×His-tagged proteins, and proteins eluted in IMAC fractions are shown on the gels. Molecular weights of AsExoI ans AsPolIII are theoretically 55.0 kDa and 91.4 kDa. Arrows heads indicate bands on gels that were identified as the desired enzyme targets. The activity of AsExoI (C) and AsPolIII (D) was monitored by adding increasing concentrations of enzyme to molecular beacon substrate.

Figure 5:
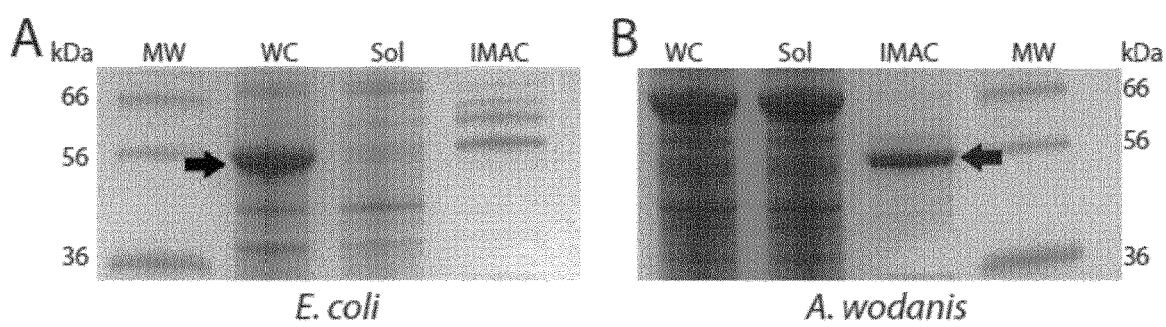

FIG. 5. Comparative expression of AsExoI in *E. coli* and *A. wodanis* strain 03/09/160. Expression of AsExoI was done in *E. coli* at 37° C. overnight (A) and in *A. wodanis* at 12° C. for 3 days (B). WC=whole cell extract, Sol=soluble protein fraction, IMAC=Immobilized metal affinity chromatography purification fractions. Arrows are pointing to bands corresponding to the expected protein (verified by mass spectrometry).

Figure 6:
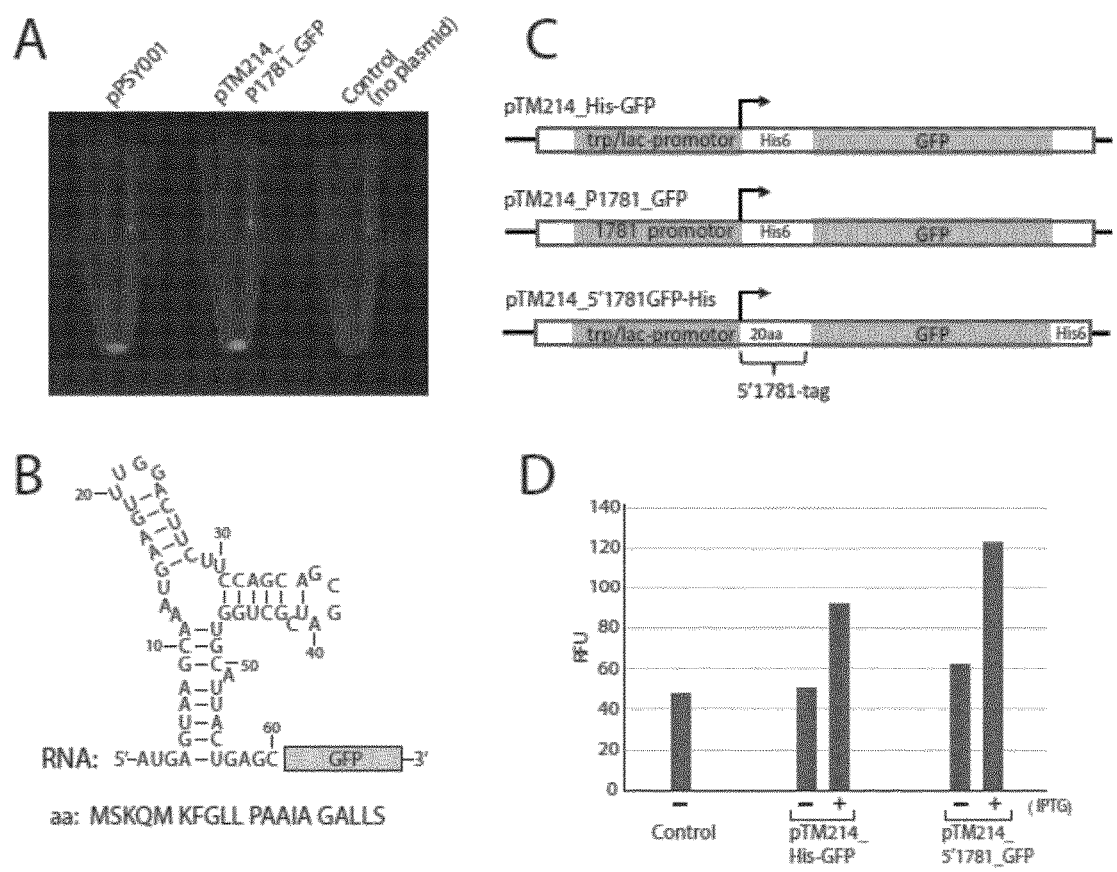

FIG. 6. Expression of gfp using a 5'-fusion sequence from Awod_I1781. Awod_I1781 was by RNA-sequencing identified in this study as the most highly expressed gene under our standard growth conditions. A. Picture shows cell pellets of *A. wodanis* containing pPSY001 (expresses gfp) pTM214_P1781_GFP (contains 300-bp of the Awod_I1781 gene promoter), or no plasmid (control in microcentrifuge tubes subjected to UV light. Bright green color shows strong expression of gfp (in FIG. 6A the fluorescent pellets (shown in white) at the base of the tubes represent the bright green color). B. Secondary structure model of the first 60-nt of Awod_I1781 mRNA (SEQ ID NO:52). The sequence was used as a 5'-fusion to improve protein expression (gfp shown as example). Also shown is the 20-mer amino acid sequence (SEQ ID NO:1). C. Schematic figure showing the expression cassettes of plasmids pTM214_His-GFP, pTM214_P1781_GFP and pTM214_5'1781_GFP. pTM214_P1781_GFP contains a 300-bp region of the Awod_I1781 promoter placed in front of gfp, and the latter contains a $P_{trc}$ promoter in front of a 60-nt/20-aa 5'-fusion from Awod_I1781 followed by gfp. pTM214_5'1781_GFP was used as backbone for cloning and expression of non-*Aliivibrio* enzyme test cases. D. Fluorescence measurements of *A. wodanis* containing no plasmid (Control), pTM214_His-GFP or pTM214_5'1781_GFP. Samples with (+) or without (−) IPTG are shown. Values are expressed as relative fluorescence units (RFU).

Figure 7:
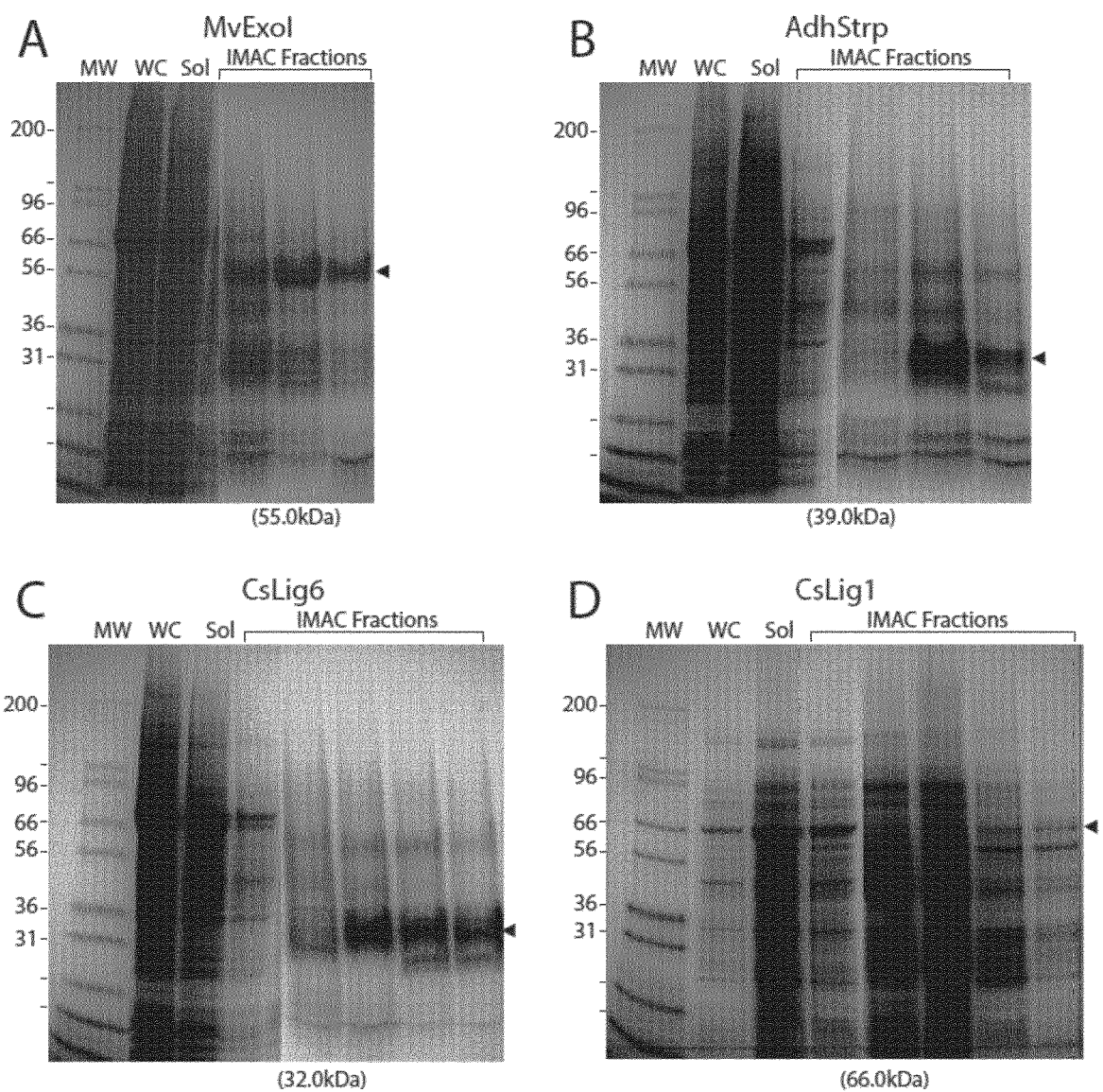

FIG. 7. Expression and purification of non-*Aliivibrio* "test-case" enzymes. Enzymes from a wider phylogenetic range were selected as test-cases. A. MvExoI (Mw—55 kDa), Exonuclease I from *Moritella viscosa*. B. AdhStrep (Mw—39 kDa), alkoholdehydrogenase from *Streptomyces*. C. CpLig6 (Mw—32 kDa), Ligase 6 from *Colwellia psychrerythraea*. D. CsLig1 (Mw—66 kDa), Ligase 1 from *Cenarchaeum symbiosum*. Arrowheads indicate bands of expected size. MW=molecular weight marker. WC=whole cell extract, Sol=lysate soluble protein fraction. Immobilized metal affinity chromatography (IMAC) was done to purify 6×His-tagged proteins, and proteins eluted in IMAC fractions are shown on the gels.

Figure 8:
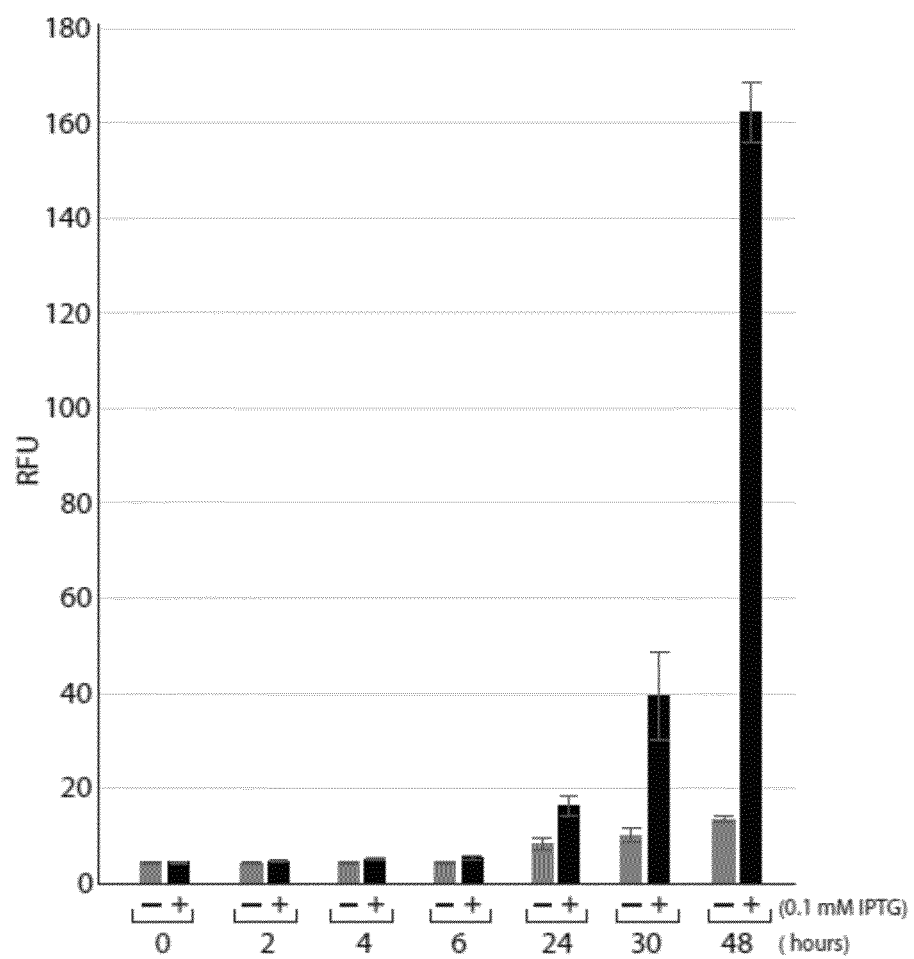

FIG. 8. Expression of mCherry from pTM214. Expression of mCherry was monitored over time in cultures of *A. wodanis* 03/09/160 harbouring pTM214 with (+) or without (−) 0.1 mM IPTG. mCherry expression from $P_{trc}$ is strongly elevated after 48 hours.

Figure 9:
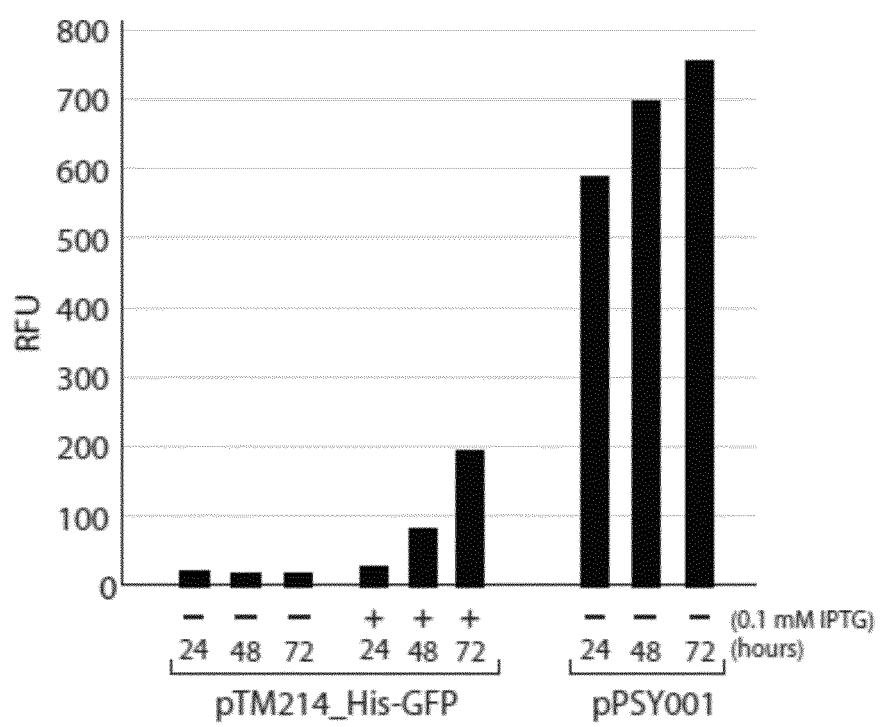

FIG. 9. Comparison of GFP expression from *A. wodanis* 03/09/160 containing pTM214_His-GFP or pPSY001. Expression of GFP from pTM214_His-GFP ($P_{trc/lac}$) is induced by the addition of IPTG. Expression of GFP from pPSY001 ($P_{lac}$ and $P_{T7}$) remains several times stronger in the absence of IPTG, and is thus regarded as constitutively expressed in *A. wodanis*. RFU=relative fluorescence units.

Figure 10:
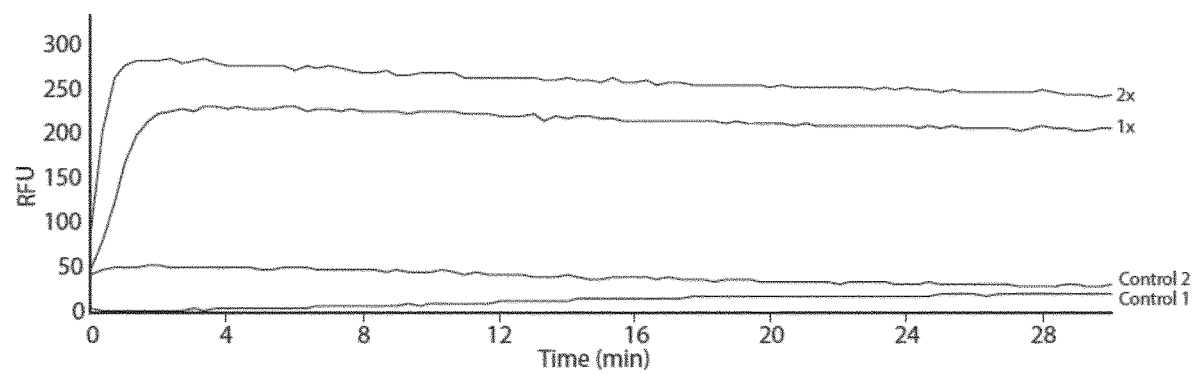

FIG. 10. Activity of MvExoI. The activity of MvExoI (Mw-55.0 kDa), Endonuclease I from *M. viscosa*, was monitored by adding 0.5 µL (1×) or 1 µL (2×) of enzyme to the molecular beacon substrate in a similar manner as described for AsExoI. In Control 1, the enzyme was replaced with the buffer used for elution during affinity purification of the His-tagged enzymes. Activity is expressed as relative fluorescence units (RFU). In Control 2, MvExoI was replaced with His-purified AdhStrep.

Figure 11:
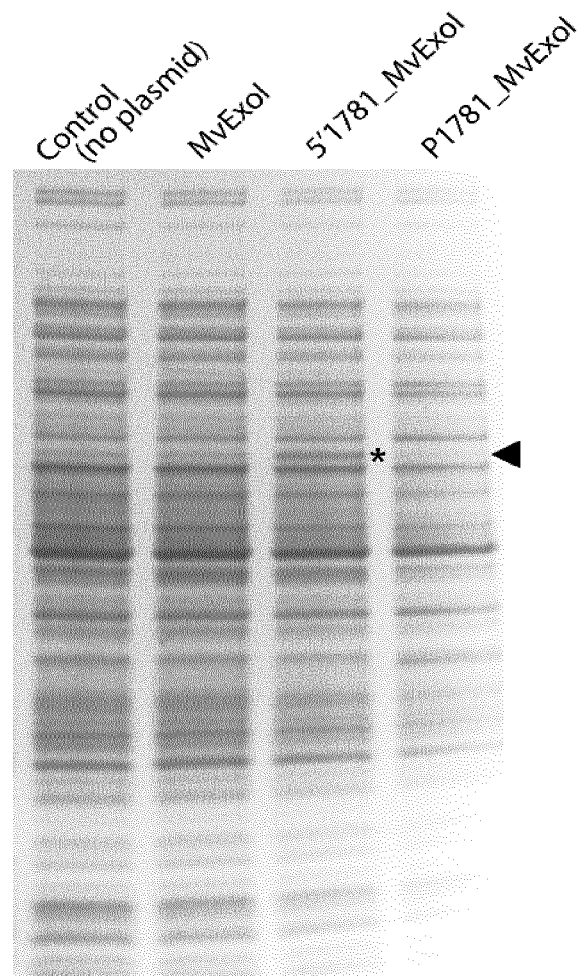

FIG. 11. Expression of *M. viscosa* exonuclease I (MvExoI) in *E. coli* strain DH5αλpir.

The SDS-PAGE gel shows protein bands from *E. coli* whole cell extracts when containing no plasmid (control), or pTM214_MvExoI (MvExoI), pTM214_5'1781_MvExoI (5'1781_MvExoI) or pTM214_P1781_MvExoI (P1781_MvExoI). 5'1781_MvExoI expressed from plasmid pTM214_5'1781_MvExoI (5'1781_MvExoI) encodes *M. viscosa* exonuclease I (MvExoI) having an N-terminal fusion moiety having the amino acid sequence of MSKQMKFGLLPAAIAGALLS (SEQ ID NO:1). Plasmids pTM214_MvExoI (MvExoI) and pTM214_P1781_MvExoI (P1781_MvExoI) encode *M. viscosa* exonuclease I that does not have an N-terminal fusion moiety. pTM214_P1781_MvExoI (P1781_MvExoI) has a 300 nucleotide fragment (SEQ ID NO:3) of the promoter of the *A. wodanis* gene Awod_I1781 upstream of the MvExoI coding sequence. Overnight cultures of *E. coli* with or without plasmid were diluted 1:100 in LB medium and grown to $OD_{600\ nm}$=0.7-1 at 37° C. Cultures were then transferred to 15° C. for expression overnight. Arrow is pointing to the expected size of MvExoI (55.0 kDa), and an asterisk indicates the protein band verified by mass spectrometry as MvExoI.

Figure 12:
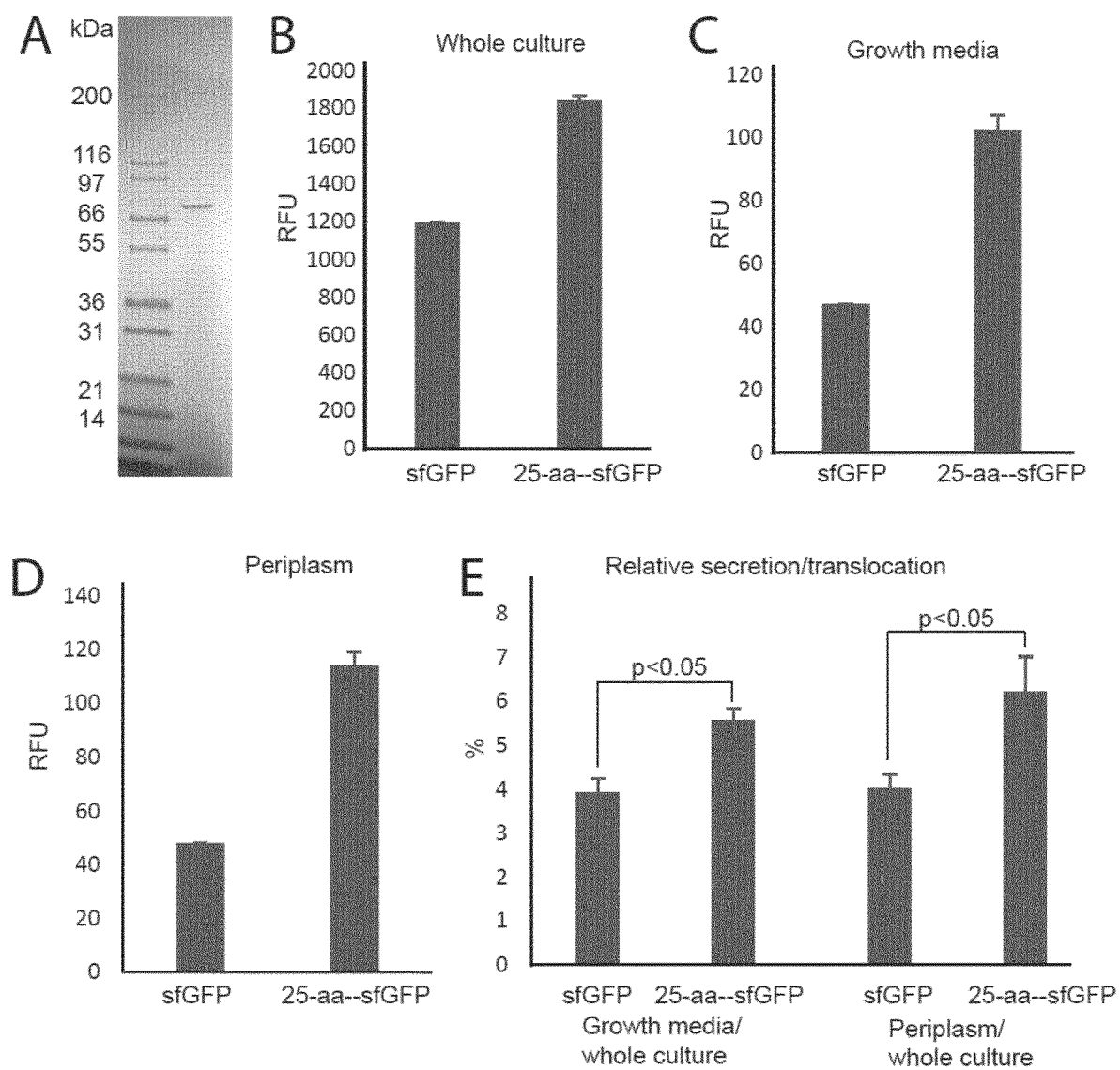

FIG. 12. A 25-aa peptide originating from AwodI11781 enhances export of sfGFP. A. SDS-PAGE of spent growth media of *A. wodanis* 03/09/160. The visible protein band was analyzed by LC-MS/MS and determined to originate from AwodI11781. B-D. Measurement of fluorescence in whole culture, growth media and periplasm of *A. wodanis* 03/09/160 expressing sfGFP (from plasmid pTM214_sfGFP) or a 25-aa-sfGFP fusion (from plasmid pTM214_174 ss_sfGFP). Bacteria without vector was used as control/blank. E. Relative secretion/translocation compared to total florescence. p value calculated with Student's t-test.

EXAMPLE

Introduction

Heterologous expression of certain proteins, e.g. cold-adapted proteins, represents today one of the biggest bottlenecks in the ongoing bioprospecting efforts to find new enzymes, e.g. from cold environments (for example the cold oceans that represents a largely untapped resource in this respect). In mesophilic expression hosts such as *Escherichia coli*, certain proteins such as cold-adapted enzymes typically form inactive aggregates. There is therefore a need to develop new cold-temperature expression systems, including identifying new host organisms and genetic tools. In this work we explored the use of the sub-Arctic bacterium *Aliivibrio wodanis* as a potential host for heterologous expression of cold-active enzymes. We have tested twelve bacterial strains (*Aliivibrio wodanis* strains), available vectors and promoters, reporter systems, used RNA-sequencing to identify the most highly expressed genes in *A. wodanis* (and thus their intrinsic promoters), explored a novel 5'-fusion to stimulate protein expression and solubility, and finally tested expression of a set of "difficult-to-express" enzymes originating from various bacteria and one Archaea. Our results show that cold-adapted enzymes can be expressed in soluble and active form in *A. wodanis*, also when expression fails in *E. coli* due to formation of inclusion bodies. Moreover, we identified a 60-bp/20-aa fragment from the 5'-end of the Awod_I1781 gene of *A. wodanis* that stimulates expression of the Green Fluorescent Protein and improves expression of cold-active enzymes when used as a 5'-fusion. These results support that *A. wodanis* and associated genetic tools are well suited for low-temperature expression and represents a useful host cell for the expression of proteins, for example cold-adapted proteins that can be difficult to express in mesophiles.

Results and Discussion

Selection of Strains and Genetic Tools

Table 1 shows the twelve *A. wodanis* strains that were selected from our in-house strain collection for further characterization to identify promising expression host candidates. Strains were tested for growth rate, resistance against some commonly used antibiotics (in biotechnological applications), and conjugation efficiency (uptake and stability of plasmids).

Preliminary tests showed that *A. wodanis* does not grow at temperatures above 20° C., and has an optimal growth rate from approximately 12-18° C., and all tested strains showed very similar growth profiles. FIG. 1A shows growth in standard culture flasks for one representative strain (03/09/160). *A. wodanis* grows considerably faster at 12° C. than at 4° C., which can be expected, with doubling times of approximately 150 min and 25 hours, respectively. Moreover, *A. wodanis* uses three and six days to reach maximum optical densities, at 12° C. and 4° C., respectively. At 12° C. the bacterium reaches $OD_{600\ nm}=7$ in standard LB medium supplemented with 2.5% NaCl.

Next, we tested for resistance to antibiotics, four of which are commonly used in biotechnological applications, namely carbenicillin, kanamycin, tetracycline and chloramphenicol. Resistance of *A. wodanis* strains to ampicillin, nitrofurantoin, tetracyclines, cefoxitin and sulfamethoxazole have been reported. The twelve strains used in this study were sensitive to chlorampenichol and tetracycline, of intermediate sensitivity to kanamycin and showed resistance to carbenicillin (see Table 1).

To test the ability of *A. wodanis* to take up plasmids, each strain was conjugated with the plasmid pTM214 (Miyashiro et al., 2011). In *E. coli* the mCherry fluorescent protein is constitutively expressed from pTM214, but in *A. wodanis* mCherry expression from pTM214 requires the addition of IPTG to the growth medium. It is straightforward to discriminate between *E. coli* and *A. wodanis* cells after conjugation. This is because only *A. wodanis* grows well under the culture conditions used (12° C. for 3 days in LB agar with 2.5% NaCl and 2 μg/ml chlorampenichol). *E. coli* does not grow under these conditions. Thus, only *A. wodanis* colonies carrying the pTM214 plasmid grow under these conditions. Also, as the growth medium (agar plates) does not contain IPTG, *A. wodanis* colonies are identifiable by their lack of mCherry expression. As mentioned above, in *A. wodanis* mCherry expression from pTM214 requires the addition of IPTG to the growth medium (unlike *E. coli* which express mCherry from pTM214 constitutively). FIG. 1B shows that six of the twelve *A. wodanis* strains (i.e., strains 02/09/382, 01/09/401, 88/09/441, 04/60/17347, 03/09/160 and K7F1 150913) readily receive and accept the foreign plasmid (pTM214) through conjugation. The six recipient strains were next tested for their ability to receive and integrate the integrative plasmid pNQ705 (Milton et al., 1996). A 250 bp DNA region homologous to the *A. wodanis* ainS gene was first inserted into pNQ705 to promote genomic integration. The test was done in three experimental replicates (for each strain), and regarded as positive if at least one integration into the bacterial host genome was found. FIG. 1B shows that integration was found for strains 02/09/382, 88/09/441, 04/60/17347, 03/09/160 and K7F1 150913, i.e., five of six tested strains.

Next, we used the plasmid pVSV208 to determine the capacity of strains to express a reporter protein, i.e., the red fluorescent protein (RFP), under antibiotic (chloramphenicol) pressure. Only strains that received the pTM214 plasmid was tested (see above). First, expression was monitored by examining the morphology (color) of colonies using a fluorescent microscope. Bright red colonies of strains 01/09/401 and 03/09/160 indicated strong RFP expression. For strain 88/09/441, we observed great variation, from bright red to white color, thus indicating uneven expression levels between individual colonies. Colonies of strains 02/09/382, 04/60/17347 and K7F1 150913 were less bright. Second, RFP expression was monitored in liquid cultures by measuring fluorescence (588 nm) in the supernatant of lysed cell cultures. FIG. 1C shows that the relative fluorescence values are in good agreement with the colony morphologies (colours) described above. Again, strains 01/09/401, 88/09/441 and 03/09/160 produced highest fluorescence intensities.

In summary, based on the results described above strains 01/09/401 and 03/09/160 were selected as candidate expression hosts for cold-temperature protein expression. Both of these strains grow well at low temperature to relatively high optical densities, they can receive plasmids via conjugation, and they can stably express the RFP reporter system. Strain 03/09/160 has additionally been shown to be capable of integrating plasmids efficiently into the genome.

Expression of Green Fluorescent Protein Reporter System at Low Temperature

Two *A. wodanis* strains (01/09/401 and 03/09/160) were next tested for their ability to support expression of a His-tagged green fluorescent protein (GFP) from a strong lac promoter ($P_{lac}$). To do this we constructed the plasmid pPSY001, which was based on a His-ZZ-GFP fragment amplified from a pETZZ1a vector (Merck), and cloned into a pVSV105 (Dunn et al., 2006) backbone (FIG. 2A) (see Materials and Methods for cloning details). In a pre-experiment, cultures of *A. wodanis* 03/09/160 containing pTM214 were induced by adding 0.1 mM IPTG to monitor expression over time. IPTG induces expression from the $P_{trc}$ promoter of the pTM214 plasmid. By measuring mCherry expression we found that expression is strongly elevated after 48 hours (FIG. 8). In a similar experiment we also tested induction of gfp from pTM214_His-GFP, and compared to expression levels of gfp from pPSY001 (FIG. 9). This experiment shows that $P_{lac}$ in pPSY001 is not dependent of IPTG induction (it is constitutively active in *A. wodanis*), and it supports considerably stronger expression than the inducible $P_{trc}$ in pTM214.

Strains 01/09/401 and 03/09/160 carrying the pPSY001 plasmid were grown in 15 mL cultures in 50 ml Falcon tubes at 4° C. and 12° C. at 200 rpm, and left for six (4° C.) and two (12° C.) days. GFP expression was first confirmed by collecting 1 mL samples and by measuring fluorescence (485-538 nm) in the supernatant of lysed and pelleted cells. His-tagged GFP from the remaining culture was affinity purified, and separated on a SDS-PAGE. FIG. 2B shows the coomassie stained SDS-polyacrylamide gel with bands identified by mass spectrometry as GFP. From the gel, we conclude that expression levels are essentially same in strains 01/09/401 and 03/09/160. Apparently, the amount of GFP is also very similar at 4° C./six days and 12° C./two days, which shows a potential to produce proteins at temperatures approaching freezing.

Expression, Purification and Activity of Cold-Adapted Enzymes from the *Aliivibrio* Genus Having shown expression of three reporter systems (mCherry, RFP and GFP) we next wanted to test "difficultto-express" cold-adapted enzymes in *A. wodanis*. Test-cases were selected from terminated projects (due to unsuccessful or poor expression in *E. coli*) at the Norwegian Structure Biology Center (NorStruct). As test-cases we first selected two enzymes, i.e., Exonuclease I (AsExoI) and DNA Polymerase 11 (AsPoIII), both from *Aliivibrio salmonicida* (in the present study the AsExoI and AsPoIII enzymes are His-tagged). The rational was that expression had previously failed in *E. coli* due to formation of inclusion bodies, and that they originate from a close relative of *A. wodanis* (which improves chances of successful expression).

The pTM214 vector with a weaker, but inducible (by IPTG) promoter ($P_{trc}$), was chosen for this experiment to reduce chances of cell toxicity due to strong constitutive expression from pPSY001. Insertion of the two enzyme genes into the vector was done using Fast cloning (Li et al., 2011) (see materials and methods for details). The final plasmid constructs were named pTM214_AsExoI and pTM214_AsPoIII (Table 4), and transferred into *A. wodanis* by conjugation. Expression was done in strains K7F1 150913, 02/09/382, 01/09/401, 88/09/441, 04/60/17347 and 03/09/160 to verify that strains expressing highest amounts of RFP expression (FIG. 1C) also perform best when expressing cold-adapted enzymes. Expression was done in 15 mL LB supplemented with 2.5% NaCl, 2 µg/ml chloramphenicol and 100 mM IPTG for 3 days at 12° C. After three days of expression, samples of whole cell extracts and soluble proteins were separated by SDS-PAGE. FIG. 3 shows that protein bands of AsExoI are visible for strains 01/09/401, 88/09/441 and 03/09/160, which is in agreement with RFP expression. Note that soluble (Sol) samples in FIG. 3 represent affinity purified material, the AsExoI is His-tagged and was purified as described in the method section herein. Based on this result and the additional characterizations described above, strain 03/09/160 was chosen as the "standard" expression strain for the remaining part of this study.

FIG. 4 shows expression, purification and activity of the enzymes AsExoI and AsPoIII. They were both expressed using strain 03/09/160, affinity purified on an IMAC column, and visualized by SDS-PAGE. Bands representing both proteins are clearly visible, and specific fluorescence molecular beacon-based (contained fluorophore and quencher) assays showed dose-dependent exonuclease and DNA polymerase activities, respectively (see Materials and methods for assay details), thus demonstrating that the proteins are expressed in active form at low temperature.

Next, we directly compared the performance of *A. wodanis* to that of *E. coli*, when expressing the cold-active enzyme AsExoI. pTM214_AsExoI was expressed (i) as described above in *A. wodanis* 03/09/160 at 12° C. for 3 days, and (ii) in *E. coli* at 37° C. overnight. FIG. 5 shows that AsExoI is expressed in high quantities in *E. coli*, and forms a distinct strong band on the SDS-PAGE gel in the cell whole extract. However, the protein is lost from the soluble protein fraction, thus supporting that the protein forms unproductive inclusion bodies in *E. coli*. In contrast, AsExoI is expressed in lower quantities in *A. wodanis*, but is readily affinity purified from the soluble protein fraction and produced a distinct band on the gel.

In summary, based on expression of the exonuclease AsExoI, originating from *A. salmonicida*, we selected strain 03/09/160 as our standard *A. wodanis* strain for expression. The two enzymes AsExoI and AsPoIII are readily expressed in *A. wodanis* 03/09/160 in active form. AsExoI is expressed as inclusion bodies in *E. coli* at 37° C.

A 60 bp/20-Aa Fragment Originating from a Highly Expressed Gene (Awod_I1781) Elevates Expression of a Gfp Fusion In an attempt to increase the protein production in *A. wodanis* we adapted a strategy, in which the 5'-end of a highly expressed gene is used as a fusion partner, and added to the 5'-coding region of the target gene. Another strategy that we took into consideration was that the addition of a strong RNA stem-loop to the mRNA 5'-end can enhance expression. To find the most highly expressed genes, we cultivated *A. wodanis* 03/09/160 under our standard growth conditions, harvested cells at $OD_{600\ nm}$=2 (exponential phase), and used RNA-sequencing. After cultivation, total RNA was extracted, rRNA-depleted, quantified and quality controlled, and finally subjected to cDNA library preparation and sequencing using the Illumina MiSeq technology (v3 chemistry, 2×75-bp, 25 mill reads, 3.75 Gb total output). A Galaxy analysis pipeline of EDGE-pro v1.0.1 and DESeq was used to align reads onto a complete *A. wodanis* 03/09/160 genome (derived from PacBio sequencing in this work), and estimate mean expression levels across biological replicates.

Table 2 shows a list of the top ten most highly expressed genes in *A. wodanis* 03/09/160. Interestingly, the level of expression of gene Awod_I1781 is 2.2× higher than that of the second most highly expressed gene (Awod_I1528), and 3.1× higher than that of number three on the list (Awod_I1596). A 300-bp region upstream of Awod_I1781 (i.e., the promoter) was cloned into the pTM214 vector in front of gfp (the plasmid was named pTM214_P1781_GFP) to verify that the promoter can support strong expression in *A. wodanis* (FIG. 6A).

The above-mentioned 300 bp region upstream of Awod_I1781 has the following nucleotide sequence (SEQ ID NO:3) (5' to 3'):

```
tttactgataaaatggtcatttattgtgtgaaatcacttttttgtggca cagaccccttttttaaataaaagcccctaagtttaattgactttcatct gacaatagtatgaaattcacactgctatcactacttgaataacattgttc tgacatagcgtttatggcatgaaatgttggacggtggttaagtttgtttt gttatatgttaaggtttcttacatagacagactacgtgaagttggctaca agtcgatttgtataaaagattttataaatatatatttggagataaaaata
```

Further analysis of Awod_I1781 (the most highly expressed gene) revealed that the first 60-bp of the 5'-coding region can potentially form a strong RNA secondary structure consisting of three base-paired regions, and two terminal loops (FIG. 6B). This 60-bp/20-aa sequence was next cloned into pTM214 in front of (i.e. 5' to) a gfp/C-terminal His-tag, to monitor any stimulating effect on protein expression (from $P_{lac}$. This construct was named pTM214_5'1781GFP-His. FIG. 6D shows a comparison of *A. wodanis* cells expressing GFP from pTM214_His-GFP and pTM214_5'1781 GFP-His. The addition of the 1781 5'-fusion (i.e. the 60-bp/20-aa sequence/tag) results in a moderate increase in fluorescence, both from uninduced and induced cells.

In summary, we used RNA-sequencing to find the most highly expressed genes in *A. wodanis* 03/09/160. A 60-bp sequence from the 5'-coding region of Awod_I1781 (by far the most highly expressed gene) was used as a 5'-fusion to stimulate expression of GFP. There was a stimulating effect on expression, which proved particularly effective when coupled to cold-adapted enzymes during low-temperature expression (see below).

Expression of Cold-Adapted Enzymes from Non-*Aliivibrio* Microbial Sources

The following four (non-*Aliivibrio*) enzymes were next selected for test-expression: (i) Exonuclease I (MvExoI) from *Moritella viscosa* (Gammaproteobacteria; Alteromonadales; Moritellaceae), (ii) ligase 1 (CsLig1) from *Cenarchaeum symbiosum* (Archaea; TACK group; Thaumarchaeota; Cenarchaeales; Cenarchaeaceae), (iii) ligase 6 (CpLig6) from *Colwellia psychrerythraea* (Gammaproteobacteria; Alteromonadales; Colwelliaceae) and (iv) alkoholdehydrogenase (AdhStrep) from *Streptomyces* (Actinobacteria; Streptomycetales; Streptomycetaceae).

The respective four genes were first cloned into the pTM214 vector, but downstream protein expression experiments did not produce any detectable bands after SDS-PAGE (Data not shown). Therefore, the same enzyme genes were next cloned into pTM214 behind the 60-nt/20-aa fusion from gene Awod_I1781, and conjugated into *A. wodanis* 03/09/160. Expression was performed as described earlier. FIG. 7 shows that bands corresponding to all four proteins are clearly visible on gels, when samples of fractions collected after affinity purification of the His-tagged enzymes were run on SDS-polyacrylamide gels. Identity of bands was verified by mass spectrometry. Finally, activity of MvExoI was tested using the same assay as described herein for AsExoI. The enzyme responds in a dose-dependent manner, and is indeed expressed and purified in active form (FIG. 10). This suggests that the 20-aa fusion moiety (i.e. the 20-aa tag) does not interfere with the enzyme activity.

To test if the 60-nt/20-aa fusion can enhance expression in *E. coli* at low temperature (i.e., 15° C.), the 20-aa tag-MvExoI fusion (in pTM214) was expressed in *E. coli* strain DH5αλpir. Cultures of *E. coli* carrying the MvExoI fusion plasmid (or control plasmids) were grown in LB (w/34 µg/ml chloramphenicol) to $OD_{600\ nm}$=0.7-1 at 37° C. Cultures were next transferred to 15° C. for expression over night. FIG. 11 shows the resulting SDS-PAGE of soluble proteins. Similar to the results from *A. wodanis* (see FIG. 7), expression of MvExoI is significantly enhanced by the presence of the 20-aa fusion moiety. A band identified as MvExoI is clearly visible for the sample containing the 20-aa fusion moiety-MvExoI fusion construct, whereas a faint band corresponding to a background band is visible in control samples (i.e., *E. coli* with no vector, and two contructs with fusion-free MvExoI).

To summarize, four enzymes originating from non-*A. wodanis* organisms, including organisms very distantly related to *A. wodanis* (i.e., CsLig1 from Archaea) were expressed and purified. The activity of Exonuclease I from *M. viscosa* was tested and found to be active. Interestingly, the addition of a 60-nt/20-aa fusion, significantly increased the expression from not visible on gels to readily visible, both in *A. wodanis* and in *E. coli*. Adapting to a stronger promoter system like T7 may increase expression/protein production. So far, the biggest benefit with the *A. wodanis* system is apparently the increase in successful protein folding of cold-adapted enzymes by expressing proteins at low temperature.

A 25-Aa Peptide Originating from AwodI1781 Enhances Export of sfGFP

FIG. 12A shows an SDS-PAGE of 5× concentrated total proteins from spent media after 48 hours of growth (to $OD_{600}$~2) of *A. wodanis* 03/09/160 in a medium without high molecular weight proteins (5 g yeast extract, 25 g NaCl, 10 g casamini acids). A single band corresponding to a protein originating from AwodI1781 is readily visible [identified by Tandem mass spectrometry (MS-MS)]. This result shows that the highly expressed gene AwodI1781 is responsible of producing a highly expressed protein that is exported out of the cell. This is corroborated by Signal P (Petersen et al., 2011) that predicts the presence of a 25-aa signal peptide in the N-terminus of the corresponding protein. This signal peptide has the amino acid sequence of SEQ ID NO:4. SEQ ID NO:4 corresponds to SEQ ID NO:1 but has an additional 5 amino acids at the C-terminal end as compared to SEQ ID NO:1.

To test if the AwodI1781 signal sequence (signal peptide) can be used to translocate recombinantly expressed proteins into the periplasm, or growth medium, a plasmid was constructed such that the 25-aa peptide (SEQ ID NO:4) was placed in front of the super folder GFP (sfGFP). This plasmid thus encoded a fusion protein, with the 25-aa peptide (SEQ ID NO:4) located N-terminally with respect to the sfGFP. When translocated to the periplasmic space, sfGFP is fluorescent (Aronson et al., 2011). The resulting construct (named pTM214_174 ss_sfGFP) was conjugated into *A. wodanis* 03/09/160. A control construct (pTM214_sfGFP), which encodes sfGFP without the N-terminal 25-aa peptide was used in parallel experiments as a control. After 48 hours of growth the fluorescence was determined in i) growth media with cells (also referred to herein as "Whole Culture") (FIG. 12B), ii) in the growth media (no cells) (FIG. 12C), and finally iii) in the periplasm (FIG. 12D). *A. wodanis* 03/09/160 without vector was used as the control/blank. Both sfGFP and the 25-aa-sfGFP fusion were detected in the growth media and periplasm. Interestingly, the 25-aa peptide significantly enhances the translocation/secretion of sfGFP (FIG. 12E). E.g., the relative fluorescence units (RFU) measurements are approx. 2× when sfGFP is expressed as a fusion protein with the 25-aa peptide. It has previously been reported that sfGFP itself can be used as a carrier protein in *E. coli* for secretion of recombinant fusion proteins, the authors describe how the beta-barrel shape and negative charges of the molecule is causing the translocation of the molecule (Zhang et al., 2017). This can explain the relatively high levels of secretion of sfGFP, even without the 25-aa signal peptide.

In summary, the first 25-aa originating from AwodI1781 enhance translocation of sfGFP into its surroundings, when used as an N-terminal fusion peptide. Secretion of recombinantly expressed proteins can have huge advantages, such as improved folding and post-translational modifications, easier downstream purification and processing, and compatibility with continuous culturing.

CONCLUDING REMARKS

We have in this work used the sub-Arctic bacterium *A. wodanis* as an expression host for "difficult-to-express" enzymes. Basic characterization of twelve strains suggests that several strains are useful and that strain 03/09/160 is particularly suitable for expression, and by using RNA-sequencing we revealed that a 60-nt/20-aa sequence of the most highly expressed gene can be used as a 5'-fusion to enhance expression of the downstream fusion partner. Three reporter systems and six enzymes were expressed at low temperature, the activity of two of the enzymes was confirmed by molecular beacon-based assays.

We have also found that a 60-nt/20-aa sequence of the most highly expressed gene in *A. wodanis* can be used as a 5'-fusion to enhance expression of the downstream fusion partner in a non-*Aliivibrio* species, *E. coli*.

We have also found that a 75 nucleotide (nt)/25 amino acid (aa) sequence of the most highly expressed gene in *A. wodanis* can be used as a 5'-fusion to enhance expression and secretion of a protein from bacterial cells.

The global market for specialty enzymes is continuously growing, driven e.g., by the demand in the pharmaceutical industry, development of novel high-value enzymes, advancements in the biotechnology industry, the continued need for cost-efficient manufacturing process, and calls for greener technologies. One major driver is an increasing demand for new enzymes that work efficiently at low temperatures, due to the growing need for cleaner and greener technology to preserve the environment. This work contributes to the development of useful biotechnology tools to unlock further potential in developments in protein expression systems, e.g. for the expression of cold-adapted enzymes, and possibly other unstable products, e.g., immunoglobulin fragments.

Materials and Methods
Bacterial Strains and Growth Conditions

Twelve *A. wodanis* strains used in this study are listed in Table 1. Bacteria were revived from −80° C. by transferring frozen cells onto Blood agar or Marine agar plates, and placing them at 12° C. for 24-48 hours. After reviving, the cells were grown in LB (Lysogeny Broth) supplemented with 2.5% NaCl liquid cultures (LB +2.5% NaCl) for one week at 12° C., or two weeks at 4° C. Growth temperature was 12° C. (standard), except for one experiment where expression of AsExoI was tested at 4 and 12° C., and during conjugative transfer of plasmids from *E. coli* cc118 λpir to *A. wodanis* where bacteria were grown in standard LB at 37° C. Plasmid-carrying *A. wodanis* strains were always freshly made by conjugation before experiments (not revived from −80° C.).

Antibiotic Resistance Test

Antibiotic susceptibility testing was done by streaking *A. wodanis* cells onto LB plates supplemented with 2.5% NaCl and one of the following antibiotics: Chloramphenicol (2 μg/mL, Tetracycline (10 μg/mL), Carbenicillin (100 or 200 μg/mL) or Kanamycin (50 or 100 μg/mL). *A. wodanis* was regarded as susceptible (score=0) if no growth was detected, as intermediate susceptible (score=0.5) if poor growth was detected, or as resistant (score=1) if good growth was detected. The tested concentrations of antibiotics were similar to the recommended working concentrations for *E. coli*, except Chloramphenicol that was tested at 2 μg/mL (instead of 25 μg/mL). If the test scored as "resistant", then the test was redone using 2× of the recommended concentration. All *A. wodanis* strains were streaked onto same agar plate and grown at 12° C. for 2 days.

Conjugation and Plasmid Uptake Test

The capacity of *A. wodanis* to receive conjugative plasmids was tested using a tri-parental mating approach. *E. coli* CC118 λpir (pEVS104) (Stabb and Ruby, 2002) as helper strain and *E. coli* CC118 λpir (pTM214) (Miyashiro et al., 2011) was used as donor. *E. coli* strains were grown to $OD_{600}$ 0.5-0.7 in LB medium with kanamycin (50 μg/mL) and chloramphenicol (20 μg/mL), respectively, at 37° C. "The recipient" *A. wodanis* was grown to $OD_{600}$=1-2 in 3 mL LB supplemented with 2.5% NaCl at 12° C. One mL of each bacteria were next pelleted and resuspended in LB medium to original volume. After a second centrifugation and resuspension, 500 μL of donor, helper and recipient bacteria were mixed and pelleted by centrifugation. The supernatant was removed and the pellet was resuspended in a small volume of residual LB medium (approx. 20 μL). The bacterial mix was spotted on an LB agar plate with 1% NaCl and incubated at 16° C. Conjugates with replicating vectors (in this case pTM214) were incubated for 24 hours, whereas those with integrating vectors (pNQ705) were incubated for 48 hours. The plasmids pTM214 and pNQ705 each carry a chloramphenicol resistance gene. After incubation, bacteria were resuspended in LB with 2.5% NaCl, spread on LB agar with 2.5% NaCl, containing 2 μg/mL chloramphenicol and incubated at 12° C. for 3 days. *E. coli* do not grow under these conditions. The number of colonies on agar plates were finally counted to assess the efficiency of DNA uptake. Plasmids were routinely transferred into *A. wodanis* as described above for pTM214 or pNQ705.

Cloning

The pPSY001 plasmid was constructed by first PCR-amplifying a region from the pETZZ-1A vector containing the promoter and His-ZZ-GFP using the oligonucleotides 1F_T7term (ATTAGGTACCCGCCGCGCTTAAT (SEQ ID NO: 43)) and 2R_T7LacO (TAATGCATGCGAAAT-TAATACGACT (SEQ ID NO:44)). The PCR product was treated with restriction enzymes KpnI and SphI, and ligated into pVSV105 pretreated with KpnI and SphI. The ligation mix was incubated at RT for 1 hour and transformed into *E. coli* CC118 λpir.

For test expression, genes of interest were PCR-amplified using primer pairs and a gateway plasmid (pET151/TEV/D-TOPO or pENTR/TEV/TOPO) containing the target gene as the template. Amplified DNA was inserted into vector (pTM214) using Fast cloning technique, according to protocol (Li et al., 2011). Primers and the resulting plasmids are shown in Table 3 and Table 4. Table 4 indicates that pTM214 contains a mCherry gene. When pTM214 was used as a vector for other genes, the mCherry gene was not present (i.e. it was replaced by the other gene). Non-*Aliivibrio* test cases were expressed with or without a 5' fusion partner (DNA sequence: 5'-ATGAGTAAGC AAATGAAGTT TGGACTTCTT CCAGCAGCGA TCGCTGGTGC ATTACTGAGC-3' (SEQ ID NO:2)) originating from *A. wodanis* 03/09/160 gene Awod_I1781. The polynucleotide sequence of SEQ ID NO:2 encodes the amino acid sequence of SEQ ID NO:1.

Super Folder GFP (sfGFP) Constructs

Superfolder GFP (sfGFP) (Pedelacq et al., 2006) was ordered as a synthetic construct including N-terminal TEV-site (for later fusion-proteins) and C-terminal His-tag (GeneArt Strings from Thermo Fisher), and cloned into vector pTM214 using FastCloning. The resultant plasmid is named pTM214_sfGFP.

Another plasmid (pTM214_174 ss_sfGFP) was also constructed which is analogous to pTM214_sfGFP, but has a 25 amino acid peptide (SEQ ID NO:4) fused N-terminally with respect to the sfGFP (i.e. the sfGFP is encoded as a fusion protein, with the 25 amino acid peptide of SEQ ID NO:4 located at the N-terminal end of the sfGFP). The 25 amino acid peptide of SEQ ID NO:4 is encoded by the nucleotide sequence of SEQ ID NO:5. Plasmid pTM214_174 ss_sfGFP was also generated using FastCloning.

Recombinant Expression and Purification of his-GFP

*A. wodanis* 03/09/160, containing pPSY001, was grown in 15 ml cultures (LB with 2.5% NaCl and 2 μg/mL chloramphenicol) at 4° C. and 12° C. GFP was expressed for six days at 4° C. and two days at 12° C. One mL of culture was pelleted and lysed in 100 μL BugBuster (MerckMillipore) according to the manufacturer's protocol, incubated at room temperature for 30 minutes and finally pelleted. 50 μL of supernatant was used to measure GFP fluorescence in a Spectramax Gemini (Molecular Devices) spectrophotometer at wavelength 485-538 nm.

Similarly, GFP was expressed from the pTM214-His-GFP vector by adding different concentrations of IPTG in range from 0.05-0.5 mM. Culture was grown in LB+2.5% NaCl, for 6 days at 12° C.

Recombinant Expression and Purification of Test Cases

Test-case proteins were expressed in *A. wodanis* from their respective plasmids (see Table 4) by growing the bacterium in 1 L LB supplemented with 2.5% NaCl, 2 µg/ml chloramphenicol and 100 mM IPTG for 3 days at 12° C. Cells were then spun down (6,000 rpm, 30 min, 12° C.) and lysed in 30 mL lysis buffer (50 mM Tris pH 8.0, 750 mM NaCl, and 5% (v/v) glycerol) supplemented with 1× Complete protease inhibitor cocktail (Roche) and 1 U/µL HL/SAN DNase (ArcticZymes). The cells were disrupted using a cell disruptor (Constant Systems, Ltd.) at 1.38 kbar in four cycles. The lysate was cleared by centrifugation at 20,000×g for 30 min at 4° C. Affinity purification of test proteins was carried out on a 5 mL HisTrap HP column (GE Healthcare) equilibrated with buffer A (50 mM Tris pH 8.0, 750 mM NaCl, 5% (v/v) glycerol and 10 mM imidazole) using an ÅKTA purifier (GE Healthcare). The bound protein was eluted across a gradient of 0-100% buffer B (50 mM Tris pH 8.0, 750 mM NaCl, 5% (v/v) glycerol and 500 mM imidazole). The purity of the protein was evaluated by SDS-PAGE and the identity of proteins was verified using a Tandem mass spectrometry (MS-MS) service at the Tromsø University Proteomics Platform (TUPP).

*Moritella viscosa* exonucleaseI (MvExoI) was expressed in *E. coli* strain DH5αλpir. Briefly, overnight cultures of *E. coli* harboring vector were diluted 1:100 in LB medium containing 34 µg/ml chloramphenicol and grown to an OD600 of 0.7-1 at 37° C. Cultures were then transferred to 15° C. and further incubated over-night. Cultures were pelleted, followed by sonication. Soluble proteins were analyzed on SDS-PAGE. The presence of MvExoI was verified by mass spectrometry.

Enzyme Activity Assays

The two enzyme activity assays used in this work are both based on so-called "molecular beacons". Each "molecular beacon" consists of a hairpin shaped DNA oligonucleotide with an internally quenched fluorophore (in this case FAM). TAMRA was used as the FAM quencher. Enzyme activity of affinity purified AsExoI and MvExoI were tested in 50 µL reactions containing the following: 0.2 µM ssDNA "molecular beacon" substrate (5'-FAM-CGCCATCGGAGGTTC-TAMRA-3' (SEQ ID NO:45)), 50 mM Tris pH 8.5, 30 mM MgCl$_2$, 1 mM DTT, 0.2 mg/ml BSA, 2% glycerol and 8.5 nM enzyme (Exonuclease I). The reaction was carried out in a black 96-well fluorescence assay plate (Corning®), and increase in FAM fluorescence (excitation at 485 nm, emission at 518 nm) was measured as relative fluorescence units (RFU) at appropriate time intervals for 40 min.

Activity assay for AsPoIII is based on a molecular beacon probe (5"-GGCCCGT$^{Dabcyl}$AGGAGGAAAGGA-CATCTTCTAGCAT$^{FAM}$ACGGGCCGTCAAGTT CATG GCCAGTCAAGTCGTCAGAAATTTCGCACCAC-3' (SEQ ID NO:46)) (modified from Summerer, 2008). The molecular beacon probe consists of a 23mer loop that is connected by a GC-rich 8mer stem region (the 8-mer stem region consists of two 8 nucleotide sequences-sequences are indicated in italics) and a 43mer extension. The fluorophores Dabcyl and FAM are attached to the indicated "T" nucleotides. Due to the loop formation the fluorophores Dabcyl and FAM are in close proximity and thus quenched. Upon extension by the DNA polymerase I of the primer (5"-GTGGTGCGAAATTTCTGAC-3' (SEQ ID NO:47)) that is annealed to the molecular beacon template the stem is opened and the increase in distance of the two fluorophores is measured by the restoration of FAM fluorescence (excitation 485 nm, emission 518 nm). Assay was monitored in 50 µL reactions containing 0.2 µM substrate (molecular beacon) mixed with 0.2 mM dNTP in 1× reaction buffer (250 mM Tris-HCl, pH 8.5, 250 mM, KCl, 25 mM MgCl$_2$) and 1×DB (1 mg/ml BSA, 5 mM DTT, 10% glycerol). The mixture was first incubated at 25° C. for 5 min, and the reaction was started by adding the purified enzyme. Increase in fluorescence was measured (excitation 485 nm, emission 518 nm) for 15 min with 10 sec intervals (total of 91 reads). All measurements were done in Corning black 96-well plate (Sigma Aldrich, CLS3991-25EA).

Isolation of Proteins in Growth Media for SDS-PAGE

*A. wodanis* 03/09/160 was grown in a media with 5 g yeast extract, 25 g NaCl and 10 g casamino acids. This media does not contain any high molecular weight protein when analysed on SDS-PAGE. The strain was grown for 48 h reaching OD$^{600}$=2. The culture was spun down and the supernatant was sterile filtered through a 0.45 µM filter. The spent growth media was then up-concentrated 5 times using a spin filter with 3K cut-off, to a protein concentration of 6.3 mg/ml.

The concentrated growth media was analyzed on SDS-PAGE and the protein was identified Tandem mass spectrometry (MS-MS) service at the Tromsø University Proteomics Platform (TUPP).

Isolation of Periplasmic Proteins

A culture of *A. wodanis* was centrifuged and the pellet was resuspended in a volume corresponding 1/10 of the original volume in periplasmic lysis buffer (0.2M Tris-HCl pH 8.0, 200 g/l sucrose and 0.1M EDTA). The suspension was incubated on ice for 20 minutes followed by centrifugation. The supernatant contained periplasmic proteins (a second step with MgCl$_2$ resulted in complete lysis of the cells).

Quantification of sfGFP in Growth Media and Periplasm

*A. wodanis* 03/09/160 with or without vector containing sfGFP was grown in standard conditions in presence for IPTG for 48 h. The fluorescence was determined using a Spektramax photometer (ex 485 nm, em 525 nm) in the following samples: 100 µl whole culture (media with cells), 100 µl supernatant, and 50 µl of the periplasmic fraction (prepared as above).

RNA Sequencing, Genome Sequencing and Bioinformatics Analyses

To find the most highly expressed genes *A. wodanis* 03/09/160 was first grown at standard growth conditions (LB supplemented with 2.5% NaCl) and harvested at OD$_{600\ nm}$=2 (exponential phase). After cultivation, total RNA was purified from cell pellets using the Masterpure complete DNA & RNA purification kit (Epicentre) following the manufacturer's protocol. The RNA quality was then determined using a Bioanalyzer and a Prokaryote Total RNA Pico Chip (Agilent Technologies). 5 µg total RNA was then used in Ribo-Zero rRNA Removal Kit (bacteria) (Epicentre) according to manufacturer instructions to remove ribosomal (r) RNA. rRNA-depleted RNA samples were ethanol precipitated, and analyzed on a Bioanalyzer using mRNA Pico Chips (Agilent Technologies). RNA-sequencing libraries were generated from rRNA-depleted RNA samples using the ScriptSeq Complete library prep kit (Illumina) in combination with library size selection using a Pippin Prep cassette (Sage Science). The size selected cDNA library was sequenced with MiSeq Reagent Kit v3 with 2×75 bp read length over 150 cycles, generating 25 mill reads and 3.75 Gb.

Reads were quality checked using FastQC. Further analysis of the RNA-Seq data was performed using a Galaxy pipeline consisting of EDGE-pro v1.0.1 (Estimated Degree of Gene Expression in Prokaryotes) and DESeq, to align the reads to the *A. wodanis* 03/09/160 genome, and estimate gene expression value as "baseMean" (mean expression level across all replicates).

Genome Sequencing

Total DNA was isolated from *A. wodanis* 03/09/160 grown at standard conditions to stationary phase using Genomic-tip 100/g (Qiagen) according to the manufacturer protocol.

The final DNA concentration and quality were measured using a Nanodrop 2000c (Thermo Scientific) instrument, and the integrity of high molecular weight DNA was examined on a 1% agarose gel. Genomic DNA was sequenced at the Norwegian Sequencing Centre (NSC) using PacBio technology platform. Libraries were constructed using PacBio 20 kb library preparation protocol. Size selection of the final library was performed using BluePippin with a 7 kb cut-off. Libraries were sequenced on Pacific Biosciences RS II instrument using P6-C4 chemistry with 360 min movie time. PacBio reads were assembled using HGAP v3 (Chin et al., 2013), and Minimus2 (Sommer et al., 2007) was used to circularize contigs. RS_Resequencing.1 software (SMRT Analysis version v2.3.0) was used to map reads back to assembled and circularized sequence in order to correct sequence after circularization.

REFERENCES

1. T. Miyashiro et al., The N-acetyl-D-glucosamine repressor NagC of *Vibrio fischeri* facilitates colonization of Euprymna scolopes. *Mol Microbiol* 82, 894-903 (2011).
2. D. L. Milton, R. O'Toole, P. Horstedt, H. Wolf-Watz, Flagellin A is essential for the virulence of *Vibrio anguillarum*. *J Bacteriol* 178, 1310-1319 (1996).
3. A. K. Dunn, D. S. Millikan, D. M. Adin, J. L. Bose, E. V. Stabb, New rfp- and pES213-derived tools for analyzing symbiotic *Vibrio fischeri* reveal patterns of infection and lux expression in situ. *Applied and environmental microbiology* 72, 802-810 (2006).
4. C. Li et al., FastCloning: a highly simplified, purification-free, sequence- and ligation-independent PCR cloning method. *BMC biotechnology* 11, 92 (2011).
5. E. V. Stabb, E. G. Ruby, in *Methods in enzymology*. (Elsevier, 2002), vol. 358, pp. 413-426.
6. T. Miyashiro et al., The N-acetyl-d-glucosamine repressor NagC of *Vibrio fischeri* facilitates colonization of Euprymna scolopes. *Molecular microbiology* 82, 894-903 (2011).
7. C.-S. Chin et al., Nonhybrid, finished microbial genome assemblies from long-read SMRT sequencing data. *Nature methods* 10, 563-569 (2013).
8. D. D. Sommer, A. L. Delcher, S. L. Salzberg, M. Pop, Minimus: a fast, lightweight genome assembler. *BMC bioinformatics* 8, 64 (2007).
9. Summerer D, (2008) DNA polymerase profiling. Methods Mol Biol. 429:225-35.
10. Petersen T N, Brunak S, von Heijne G, Nielsen H: SignalP 4.0: discriminating signal peptides from transmembrane regions. Nature methods 2011, 8:785.
11. Aronson D E, Costantini L M, Snapp E L: Superfolder GFP is fluorescent in oxidizing environments when targeted via the Sec translocon. Traffic 2011, 12.
12. Zhang Z, Tang R, Zhu D, Wang W, Yi L, Ma L: Non-peptide guided auto-secretion of recombinant proteins by super-folder green fluorescent protein in *Escherichia coli*. Sci Rep 2017, 7:6990.
13. Pedelacq J D, Cabantous S, Tran T, Terwilliger T C, Waldo G S: Engineering and characterization of a super-folder green fluorescent protein. Nat Biotechnol 2006, 24.

TABLE 1

Properties associated with *A. wodanis* strains used in this study

| Strain | Origin[1] | GenBank[2] | Antibiotics resistance[3] | | | | | |
|---|---|---|---|---|---|---|---|---|
| | | | CHL 2 µg/mL | TET 10 µg/mL | CAR 100 µg/mL | CAR 200 µg/mL | KAN 50 µg/mL | KAN 100 µg/mL |
| 06/09/139 | S. salar | GCA_000953695.1 | NA | NA | NA | NA | NA | NA |
| 89/09/5532 (1) | S. salar | JQ361718 | 0 | 0 | 1 | 1 | 1 | 0.5 |
| 90/09/325 (5) | S. salar | JQ361719 | 0 | 0 | 1 | 1 | 1 | 0.5 |
| 02/09/569 (7) | S. salar | JQ361720 | 0 | 0 | 1 | 1 | 1 | 0.5 |
| 02/09/382 (8) | S. salar | JQ361721 | 0 | 0 | 1 | 1 | 1 | 0.5 |
| 01/09/401 (11) | S. salar | JQ361722 | 0 | 0 | 1 | 1 | 1 | 0.5 |
| 88/09/441 (12) (T) | S. salar | JQ361723 | 0 | 0 | 0.5 | 0.5 | 1 | 0.5 |
| 06/09/170 (27) | S. salar | JQ361727 | 0 | 0 | 1 | 1 | 0.5 | 0.5 |
| 06/09/178 (29) | O. mykiss | JQ361731 | 0 | 0 | 1 | 1 | 1 | 0.5 |
| 04/60/17347 (35) | G. morhua | JQ361730 | 0 | 0 | 1 | 1 | 1 | 0.5 |
| 03/09/160 (37) | S. salar | JQ361729 | 0 | 0 | 1 | 1 | 1 | 0.5 |
| K7F1 150913 | S. salar | — | 0 | 0 | 1 | 1 | 1 | 0.5 |

[1] S. salar = Salmo salar (Atlantic salmon); O. mykiss = Oncorhynchus mykiss (Rainbow trout); G. morhua = Gadus morhua (Atlantic cod);

[2] GenBank accession numbers. The accession number for strain 06/09/139 refers to the genome assembly. The "JQ" Accession numbers are the accession numbers for rRNA genes.

[3] CHL = chloramphenicol; TET = Tetracycline; CAR = Carbenicillin; KAN = Kanamycin. 0 = Susceptible, 0.5 = Intermediate Susceptible; 1 = Resistant. Abbreviations for antibiotics follow that of the *American Society for Microbiology*. NA = Not analysed.

TABLE 2

Top-ten most highly expressed genes in *A. wodanis* 03/09/160.

| Gene nr. | Product | Base mean |
|---|---|---|
| Awod_I1781 | Unknown | 212918.07 |
| Awod_I1528 | Phosphoenolpyruvate carboxykinase [ATP] - Phosphoenolpyruvate carboxylase | 97425.05 |
| Awod_I1596 | ATP synthase subunit beta - ATP synthase F1sector subunit beta - F-ATPase subunit beta | 69249.87 |
| Awod_I831 | 30S ribosomal protein S1 | 51427.88 |
| Awod_I1398 | 50S ribosomal protein L16 | 45942.99 |
| Awod_I1369 | Immunogenic protein | 42958.71 |
| Awod_I1598 | ATP synthase subunit alpha - ATP synthase F1sector subunit alpha - F-ATPase subunit alpha | 40648.19 |
| Awod_I1381 | DNA-directed RNA polymerase subunit alpha - RNApolymerase subunit alpha - Transcriptase subunit alpha | 37931.23 |
| Awod_I2484 | Alanine dehydrogenase | 33312.94 |
| Awod_I1407 | Elongation factor Tu | 30288.95 |

TABLE 3

Oligonucleotides used in this study

| No.[1] | Name | Sequence (5'-3') |
|---|---|---|
| O1 | pTM214_2R | GTCGACCTGCAGGCATGC |
| O2 | pTM14_2F | GGTGAAGGGATCAATTCCCT |
| O3 | pTM214_1F | CATGCTTAATTTCTCCTCTTTAATTAGATCC |
| O4 | A.s_exoI_F | GGAGAAATTAAGCATGATGCATCATCACCATCACCATGGT |
| O5 | A.s exoI_ R | ATGCCTGCAGGTCGACTCATGATACTAACTGTTGTACGTA |
| O6 | A.s_polII_F | GGAGAAATTAAGCATGATGCATCATCACCATCACCATGGT |
| O7 | A.s_polII_ R | ATGCCTGCAGGTCGACTTAGAATAGACCTAATTGAGAAGC |
| O8 | GFP_F | AATTGATCCCTTCACCATGGGCAAAGTGAGCAAGGGCGAG |
| O9 | GFP_R | ATGCCTGCAGGTCGACCTTGTACAGCTCGTCCATGCCGAG |
| O10 | v_pTM214_changeP_F | GATCTCTGCAGTACCTGTGA |
| O11 | v_pTM214_changeP_R | ATGCATCATCACCATCACCATG |
| O12 | i_1781p_F | AGGTACTGCAGAGATCTTTACTGATAAAATGGTCATTTAT |
| O13 | i_1781p_R | GATGGTGATGATGCATTATTTTTATCTCCAAATATATATT |
| O14 | V_5_1781_F | GCTGCTGGAAGAAGTcCAAACTTCATTTGCTTACTCATGCTTAATTTCTCCTCTTTAAT |
| O15 | V_5_1781_R | GACTTCTTCCAGCAGCGATCGCTGGTGCATTACTGAGCTTTCAGGGAATTGATCCCTTCC |
| O16 | His_tag_F | ATGGTGATGGTGATGATGCTTGTACAGCTCGTCCATGCC |
| O17 | His_tag_R | CATCATCACCATCACCATTAACGACCTGCAGGCATGCAAGCTT |
| O18 | v_5his_F | GCTCAGTAATGCACCAGCGATCGC |
| O19 | v_5his_R | CATCATCACCATCACCATTAAGTC |
| O20 | i_5his_L6_F | TGGTGCATTACTGAGCCAGCAGACCACCCAGAAAACACAG |
| O21 | i_5his_L6_R | GGTGATGGTGATGATGTTAGCCGCTTGCTTTAATACGCCA |
| O22 | i_5his_strepADH_F | TGGTGCATTACTGAGCGGTCGTGCAGTTGTGTTTGAAGAA |
| O23 | t_5his_strepADH_R | GGTGATGGTGATGATGTGCACCATCAGGATGCGGACGACG |
| O24 | i_5his_MvExo_F | TGGTGCATTACTGAGCGATAACAATTCGAACAAAGAGCA |
| O25 | i_5his_MvExo_R | GGTGATGGTGATGATGTGCGCCAATTATTTTTTGACCATA |
| O26 | i_5his_Halo_F | TGGTGCATTACTGAGCGGTGATAGCACCATGCGTGCAGCA |
| O27 | I_5his_Halo_R | GGTGATGGTGATGATGGGCCATATCCAGAACAATACGACC |
| O28 | i_5his_L1_F | TGGTGCATTACTGAGCCAGTTTAGCGTTCTGGCAGGTAGC |
| O29 | i_5his_L1_R | GGTGATGGTGATGATGAACACCAGGCTGACCATCCGGCAC |

TABLE 3-continued

Oligonucleotides used in this study

| No.[1] | Name | Sequence (5'-3') |
|---|---|---|
| O30 | M.v_exoI_F | AATTGATCCCTTCACCATGGATAACAATTCGAACAAAACA |
| O31 | M.v_exoI_R | ATGCCTGCAGGTCGACTTATGCGCCAATTATTTTTTGACC |

[1]oligonucleotide number

The oligonucleotide numbers in Table 3 correspond to the following SEQ ID NOs: O1=SEQ ID NO:6; O2=SEQ ID NO:7; O3=SEQ ID NO:8; O4=SEQ ID NO:9; O5=SEQ ID NO:10; O6=SEQ ID NO:11; O7=SEQ ID NO:12; O8=SEQ ID NO:13; O9=SEQ ID NO:14; O10=SEQ ID NO:15; O11=SEQ ID NO:16; O12=SEQ ID NO:17; O13=SEQ ID NO:18; O14=SEQ ID NO:19; O15=SEQ ID NO:20; O16=SEQ ID NO:21; O17=SEQ ID NO:22; O18=SEQ ID NO:23; O19=SEQ ID NO:24; O20=SEQ ID NO:25; O21=SEQ ID NO:26; O22=SEQ ID NO:27; O23=SEQ ID NO:28; O24=SEQ ID NO:29; O25=SEQ ID NO:30; O26=SEQ ID NO:31; O27=SEQ ID NO:32; O28=SEQ ID NO:33; O29=SEQ ID NO:34; O30=SEQ ID NO:35; O31=SEQ ID NO:36.

TABLE 4

Plasmids used in this study

| Plasmid namd | Vector No.[1] | Relevant description | Plasmid backbone | Vector oligos [2] | Insert oligos [3] | Ref. [4] |
|---|---|---|---|---|---|---|
| pTM214 | V1 | Carries $P^{trc}$ followed by mCherry gene | | | | [1] |
| pNQ705 | V2 | Suicide vector. Carries $Cm^r$, pir for replicaiton. | | | | [2] |
| pVSV208 | V3 | Carries $Cm^r$, rfp | | | | [3] |
| pTM214_His-GFP | V4 | pTM214 carries N-term His-tag gfp | V5 | O1 + O2 | O8 + O9 | This work |
| pTM214_AsExoI | V5 | pTM214 carries ExonucleaseI from *Aliivibrio salmonicida* | V1 | O1 + O3 | O4 + O5 | This work |
| pTM214_AsPolII | V6 | pTM214 carries DNA PolII from *Aliivibrio salmonicida* | V1 | O1 + O3 | O6 + O7 | This work |
| pTM214_P1781_GFP | V7 | pTM214 carries 300 bp Awod_I1781 promoter/gfp | V4 | O1 + O11 | O12 + O13 | This work |
| pTM214_5'1781GFP-His | V8 | pTM214 carries 20-aa fusion/ gfp/C-term His-tag. | V4 | O14 + O17 | O15 + O16 | This work |
| pTM214_5'1781_CsLig1 | V9 | pTM214 carries 20-aa fusion/ Ligase1 from *Cenarchaeum symbiosum*/ C-term His-tag | V8 | O18 + O19 | O28 + O29 | This work |
| pTM214_5'1781_CpLig6 | V10 | pTM214 carries 20-aa fusion/ Ligase6 from *Colwellia psychrerythraea*/ C-term His-tag | V8 | O18 + O19 | O20 + O21 | This work |
| pTM214_5'1781_MvExoI | V11 | pTM214 carries 20-aa fusion/ ExonucleaseI from *Moritella viscosa*/ C-term His-tag | V8 | O18 + O19 | O24 + O25 | This work |
| pTM214_5'1781_AdhStrep | V12 | pTM214 carries 20-aa fusion/ alkoholdehydrogenase from *Streptomyces*/ C-term His-tag | V8 | O18 + O19 | O26 + O27 | This work |
| pPSY001 | V13 | pVSV105 carries His-ZZ-gfp | | | | This work |
| pTM214_MvExoI | V14 | pTM214 carries N-term His/ ExonucleaseI from *Moritella viscosa*/ C-term His-tag | V4 | O1 + O2 | O30 + O31 | This work |
| pTM214_P1781_MvExoI | V15 | pTM214 carries 300 bp Awod_I1781 promoter/ N-term His/ExonucleaseI from *Moritella viscosa* | V7 | O1 + O2 | O30 + O32 | This work |

[1]Vector number.
[2] Oligonucleotides used for amplification of vector backbone during Fast cloning. Oligonucleotides are listed in Table 3.
[3] Oligonucleotides used for amplification of insert (target gene) during Fast cloning. Oligonucleotides are listed in Table 3.
[4] References. [1] Miyashiro et al. 2011, [2] Milton et al. 1992, [3] Dunn et al. 2006.

The invention claimed is:

1. A nucleic acid molecule encoding a fusion protein comprising
   (i) a fusion moiety comprising the amino acid sequence of SEQ ID NO:1 or an amino acid sequence that is at least 80% identical to SEQ ID NO:1; and
   (ii) a protein.

2. A nucleic acid molecule encoding a fusion protein, said nucleic acid molecule comprising
   (i) a polynucleotide comprising the polynucleotide sequence of SEQ ID NO:2 or SEQ ID NO:5, or a polynucleotide sequence that is at least 80% identical to SEQ ID NO:2 or SEQ ID NO:5; and
   (ii) a polynucleotide encoding a protein.

3. A method of producing a protein, said method comprising culturing a host cell comprising a heterologous nucleic acid molecule encoding said protein under conditions suitable for the expression of the encoded protein, wherein said protein is a fusion protein comprising
   (i) a fusion moiety comprising the amino acid sequence of SEQ ID NO:1 or SEQ ID NO:4 or an amino acid sequence that is at least 80% identical to SEQ ID NO:1 or SEQ ID NO:4, and
   (ii) a protein.

4. The method of claim 3, said method further comprising, subsequent to culturing the host cell, a step of isolating the protein from the host cell or from the growth medium or supernatant.

5. The method of claim 3, wherein said host cell is an *Aliivibrio wodanis* host cell.

6. A method of producing a protein, said method comprising culturing an *Aliivibrio wodanis* host cell comprising a heterologous nucleic acid molecule encoding said protein under conditions suitable for the expression of the encoded protein, wherein said protein is a fusion protein comprising
   (i) a fusion moiety comprising the amino acid sequence of SEQ ID NO:1 or an amino acid sequence that is at least 80% identical to SEQ ID NO:1; and
   (ii) a protein.

7. The method of claim 6, wherein said *Aliivibrio wodanis* is an *Aliivibrio wodanis* strain selected from the group consisting of:
   (i) the *Aliivibrio wodanis* strain deposited under accession number ECACC 18050101;
   (ii) the *Aliivibrio wodanis* strain deposited under accession number ECACC 18050102; and
   (iii) an *Aliivibrio wodanis* strain having all the identifying characteristics of one or both of strains (i) and (ii).

8. The method of claim 6, wherein the culturing is done at a temperature of 4° C. to 18° C.

9. The method of claim 6, said method (i) further comprising, prior to culturing the *Aliivibrio wodanis*, a step of introducing said heterologous nucleic acid molecule encoding said protein into the *Aliivibrio wodanis* host cell or (ii) further comprising, subsequent to culturing the *Aliivibrio wodanis*, a step of isolating the protein from the *Aliivibrio wodanis* or from the growth medium or supernatant.

10. An *Aliivibrio wodanis* strain selected from the group consisting of:
    (i) the *Aliivibrio wodanis* strain deposited under accession number ECACC 18050101;
    (ii) the *Aliivibrio wodanis* strain deposited under accession number ECACC 18050102; and
    (iii) an *Aliivibrio wodanis* strain having all the identifying characteristics of one or both of strains (i) and (ii),
       wherein the *Aliivibrio wodanis* strain comprises a heterologous nucleic acid molecule encoding a protein.

11. The method of claim 6, said method (i) further comprising, prior to culturing the *Aliivibrio wodanis*, a step of introducing said heterologous nucleic acid molecule encoding said protein into the *Aliivibrio wodanis* host cell and (ii) further comprising, subsequent to culturing the *Aliivibrio wodanis*, a step of isolating the protein from the *Aliivibrio wodanis* or from the growth medium or supernatant.

12. The method of claim 4 further comprising the step of formulating the protein into a composition including at least one additional component.

13. The method of claim 9 further comprising the step of formulating the protein into a composition including at least one additional component.

14. The method of claim 11 further comprising the step of formulating the protein into a composition including at least one additional component.

* * * * *